United States Patent
Lee et al.

(10) Patent No.: US 9,521,960 B2
(45) Date of Patent: Dec. 20, 2016

(54) SYSTEMS AND METHODS PROVIDING EN MASS COLLECTION AND CENTRALIZED PROCESSING OF PHYSIOLOGICAL RESPONSES FROM VIEWERS

(75) Inventors: Hans C. Lee, Carmel, CA (US);
Timmie T. Hong, San Diego, CA (US);
Juan C. Munoz, San Francisco, CA (US)

(73) Assignee: The Nielsen Company (US), LLC, New York, NY (US)

(*) Notice: Subject to any disclaimer, the term of this patent is extended or adjusted under 35 U.S.C. 154(b) by 1611 days.

(21) Appl. No.: 12/263,331

(22) Filed: Oct. 31, 2008

(65) Prior Publication Data
US 2009/0131764 A1    May 21, 2009

Related U.S. Application Data

(60) Provisional application No. 60/984,260, filed on Oct. 31, 2007, provisional application No. 60/984,268, filed on Oct. 31, 2007.

(51) Int. Cl.
*A61B 5/00* (2006.01)
*G06Q 30/00* (2012.01)
(Continued)

(52) U.S. Cl.
CPC .............. *A61B 5/0484* (2013.01); *A61B 5/16* (2013.01); *A61B 5/165* (2013.01); *A61B 5/6814* (2013.01);
(Continued)

(58) Field of Classification Search
CPC ....... G06F 3/01–3/012; A61B 5/6801–5/6803; G06Q 30/0241–30/0277
(Continued)

(56) References Cited

U.S. PATENT DOCUMENTS

| | | |
|---|---|---|
| 4,145,122 A | 3/1979 | Rinard et al. |
| 4,610,259 A | 9/1986 | Cohen et al. |

(Continued)

FOREIGN PATENT DOCUMENTS

| | | |
|---|---|---|
| GB | 2221759 | 2/1990 |
| KR | 10-2000-0072489 | 12/2000 |

(Continued)

OTHER PUBLICATIONS

"Electromagnetic Interference" http://www.siemon.com/us/white_papers/02-03-22-emi.asp, accessed on Dec. 28, 2012.*

(Continued)

*Primary Examiner* — Gary Jackson
*Assistant Examiner* — Shirley Jian
(74) *Attorney, Agent, or Firm* — Hanley, Flight & Zimmerman, LLC

(57) ABSTRACT

Embodiments described herein enable "in situ" sensing, which collects and analyzes physiological responses from a large group of viewers/audiences who watch a same media instance together at a single venue. Each of the group of viewers is fitted with physiological sensors with communication capabilities to communicate with a signal collection device at or near the venue. The signal collection device collects the physiological data of the viewers from the sensors, and transmits the physiological data to a processing module at another location via a network for storage and further analysis.

66 Claims, 24 Drawing Sheets

(51) Int. Cl.

| | |
|---|---|
| *A61B 5/0484* | (2006.01) |
| *A61B 5/16* | (2006.01) |
| *H04N 7/16* | (2011.01) |
| *H04N 21/258* | (2011.01) |
| *H04N 21/422* | (2011.01) |
| *H04N 21/442* | (2011.01) |
| *H04N 21/475* | (2011.01) |
| *G06Q 30/02* | (2012.01) |
| *A61B 5/0205* | (2006.01) |
| *H04H 60/33* | (2008.01) |

(52) U.S. Cl.
CPC .......... *H04N 7/16* (2013.01); *H04N 21/25866* (2013.01); *H04N 21/42201* (2013.01); *H04N 21/44218* (2013.01); *H04N 21/4758* (2013.01); *A61B 5/0006* (2013.01); *A61B 5/0205* (2013.01); *G06Q 30/0204* (2013.01); *H04H 60/33* (2013.01)

(58) Field of Classification Search
USPC .............................................. 705/14.4–14.73
See application file for complete search history.

(56) References Cited

U.S. PATENT DOCUMENTS

| | | | |
|---|---|---|---|
| 4,626,904 A | 12/1986 | Lurie | |
| 4,686,999 A | 8/1987 | Snyder et al. | |
| 4,695,879 A | 9/1987 | Weinblatt | |
| 4,755,045 A | 7/1988 | Borah et al. | |
| 4,846,190 A | 7/1989 | John | |
| 4,931,934 A | 6/1990 | Snyder | |
| 4,955,388 A | 9/1990 | Silberstein | |
| 4,973,149 A | 11/1990 | Hutchinson | |
| 4,974,602 A | 12/1990 | Abraham-Fuchs et al. | |
| 5,226,177 A | 7/1993 | Nickerson | |
| 5,243,517 A | 9/1993 | Schmidt et al. | |
| 5,331,544 A | 7/1994 | Lu et al. | |
| 5,345,281 A | 9/1994 | Taboada et al. | |
| 5,363,858 A | 11/1994 | Farwell | |
| 5,392,788 A | 2/1995 | Hudspeth | |
| 5,406,957 A | 4/1995 | Tansey | |
| 5,410,609 A | 4/1995 | Kado et al. | |
| 5,447,166 A | 9/1995 | Gevins | |
| 5,450,855 A | 9/1995 | Rosenfeld | |
| 5,513,649 A | 5/1996 | Gevins et al. | |
| 5,537,618 A | 7/1996 | Boulton et al. | |
| 5,550,928 A | 8/1996 | Lu et al. | |
| 5,579,774 A | 12/1996 | Miller et al. | |
| 5,601,090 A | 2/1997 | Musha | |
| 5,622,168 A * | 4/1997 | Keusch et al. ................ | 600/391 |
| 5,676,138 A | 10/1997 | Zawilinski | |
| 5,687,322 A | 11/1997 | Deaton et al. | |
| 5,692,906 A | 12/1997 | Corder | |
| 5,720,619 A | 2/1998 | Fisslinger | |
| 5,724,987 A | 3/1998 | Gevins et al. | |
| 5,736,986 A | 4/1998 | Sever, Jr. | |
| 5,740,812 A | 4/1998 | Cowan | |
| 5,762,611 A | 6/1998 | Lewis et al. | |
| 5,774,591 A | 6/1998 | Black et al. | |
| 5,802,208 A | 9/1998 | Podilchuk et al. | |
| 5,802,220 A | 9/1998 | Black et al. | |
| 5,812,642 A | 9/1998 | Leroy | |
| 5,892,566 A | 4/1999 | Bullwinkel | |
| 5,983,129 A * | 11/1999 | Cowan et al. ................ | 600/544 |
| 5,983,214 A | 11/1999 | Lang et al. | |
| 5,995,868 A | 11/1999 | Dorfmeister et al. | |
| 6,001,065 A | 12/1999 | DeVito | |
| 6,032,129 A | 2/2000 | Greef et al. | |
| 6,088,040 A | 7/2000 | Oda et al. | |
| 6,099,319 A | 8/2000 | Zaltman et al. | |
| 6,170,018 B1 | 1/2001 | Voll et al. | |
| 6,171,239 B1 | 1/2001 | Humphrey | |
| 6,212,502 B1 | 4/2001 | Ball et al. | |
| 6,228,038 B1 | 5/2001 | Claessens | |
| 6,236,885 B1 | 5/2001 | Hunter et al. | |
| 6,254,536 B1 | 7/2001 | DeVito | |
| 6,286,005 B1 | 9/2001 | Cannon | |
| 6,292,688 B1 | 9/2001 | Patton | |
| 6,299,308 B1 | 10/2001 | Voronka et al. | |
| 6,309,342 B1 | 10/2001 | Blazey et al. | |
| 6,315,569 B1 | 11/2001 | Zaltman | |
| 6,322,368 B1 | 11/2001 | Young et al. | |
| 6,422,999 B1 | 7/2002 | Hill | |
| 6,435,878 B1 | 8/2002 | Reynolds et al. | |
| 6,453,194 B1 | 9/2002 | Hill | |
| 6,487,444 B2 | 11/2002 | Mimura | |
| 6,577,329 B1 | 6/2003 | Flicker et al. | |
| 6,585,521 B1 | 7/2003 | Obrador | |
| 6,609,024 B1 | 8/2003 | Ryu et al. | |
| 6,623,428 B2 | 9/2003 | Miller et al. | |
| 6,626,676 B2 | 9/2003 | Freer | |
| 6,648,822 B2 | 11/2003 | Hamamoto et al. | |
| 6,652,283 B1 | 11/2003 | Van Schaack et al. | |
| 6,656,116 B2 | 12/2003 | Kim et al. | |
| 6,678,866 B1 | 1/2004 | Sugimoto et al. | |
| 6,688,890 B2 | 2/2004 | von Buegner | |
| 6,712,468 B1 | 3/2004 | Edwards | |
| 6,792,304 B1 | 9/2004 | Silberstein | |
| 6,839,682 B1 | 1/2005 | Blume | |
| 6,842,877 B2 | 1/2005 | Robarts et al. | |
| 6,904,408 B1 | 6/2005 | McCarthy et al. | |
| 6,909,451 B1 | 6/2005 | Latypov et al. | |
| 6,978,115 B2 | 12/2005 | Whitehurst et al. | |
| 7,010,497 B1 | 3/2006 | Nyhan et al. | |
| 7,035,685 B2 | 4/2006 | Ryu et al. | |
| 7,043,056 B2 | 5/2006 | Edwards et al. | |
| 7,047,550 B2 | 5/2006 | Yasukawa et al. | |
| 7,050,753 B2 | 5/2006 | Knutson | |
| 7,113,916 B1 | 9/2006 | Hill | |
| 7,120,880 B1 | 10/2006 | Dryer et al. | |
| 7,150,715 B2 | 12/2006 | Collura et al. | |
| 7,246,081 B2 | 7/2007 | Hill | |
| 7,340,060 B2 | 3/2008 | Tomkins et al. | |
| D565,735 S | 4/2008 | Washbon | |
| 7,383,200 B1 | 6/2008 | Walker et al. | |
| 7,394,385 B2 * | 7/2008 | Franco et al. .............. | 340/573.1 |
| 7,483,844 B2 | 1/2009 | Takakura et al. | |
| 7,519,860 B2 | 4/2009 | Hatonen et al. | |
| 7,623,823 B2 | 11/2009 | Zito et al. | |
| 7,630,757 B2 | 12/2009 | Dorfmeister et al. | |
| 7,636,456 B2 | 12/2009 | Collins et al. | |
| 7,658,327 B2 | 2/2010 | Tuchman et al. | |
| 7,689,272 B2 | 3/2010 | Farwell | |
| 7,698,238 B2 | 4/2010 | Barletta et al. | |
| 7,729,755 B2 | 6/2010 | Laken | |
| 7,774,052 B2 * | 8/2010 | Burton et al. ................ | 600/544 |
| 7,840,250 B2 | 11/2010 | Tucker | |
| 7,895,625 B1 | 2/2011 | Bryan et al. | |
| 7,917,366 B1 | 3/2011 | Levanon et al. | |
| 7,930,199 B1 | 4/2011 | Hill | |
| 7,966,012 B2 * | 6/2011 | Parker ........................ | 455/426.1 |
| 7,984,468 B2 | 7/2011 | Westberg | |
| 8,014,847 B2 | 9/2011 | Shastri et al. | |
| 8,027,518 B2 | 9/2011 | Baker et al. | |
| 8,055,722 B2 | 11/2011 | Hille | |
| 8,069,125 B2 | 11/2011 | Jung et al. | |
| 8,082,215 B2 | 12/2011 | Jung et al. | |
| 8,086,563 B2 | 12/2011 | Jung et al. | |
| 8,099,315 B2 | 1/2012 | Amento et al. | |
| 8,126,220 B2 * | 2/2012 | Greig ........................... | 382/118 |
| 8,151,292 B2 | 4/2012 | Lee et al. | |
| 8,151,298 B2 | 4/2012 | Begeja et al. | |
| 8,196,168 B1 | 6/2012 | Bryan et al. | |
| 8,235,725 B1 | 8/2012 | Hill | |
| 8,255,267 B2 | 8/2012 | Breiter | |
| 8,300,526 B2 | 10/2012 | Saito et al. | |
| 8,327,395 B2 | 12/2012 | Lee et al. | |
| 8,332,883 B2 | 12/2012 | Lee et al. | |
| 8,381,244 B2 | 2/2013 | King et al. | |
| 8,473,345 B2 | 6/2013 | Pradeep et al. | |
| 8,484,081 B2 | 7/2013 | Pradeep et al. | |
| 8,494,610 B2 | 7/2013 | Pradeep et al. | |

(56) References Cited

U.S. PATENT DOCUMENTS

| | | |
|---|---|---|
| 8,494,905 B2 | 7/2013 | Pradeep et al. |
| 8,533,042 B2 | 9/2013 | Pradeep et al. |
| 8,635,105 B2 | 1/2014 | Pradeep et al. |
| 8,744,237 B2 * | 6/2014 | Baldwin et al. ............ 386/239 |
| 8,788,372 B2 | 7/2014 | Kettner et al. |
| 9,021,515 B2 | 4/2015 | Lee et al. |
| 9,336,535 B2 * | 5/2016 | Pradeep ............... A61B 5/0476 |
| 2001/0016874 A1 | 8/2001 | Ono et al. |
| 2001/0020236 A1 | 9/2001 | Cannon |
| 2001/0029468 A1 | 10/2001 | Yamaguchi et al. |
| 2001/0032140 A1 | 10/2001 | Hoffman |
| 2001/0040591 A1 | 11/2001 | Abbott et al. |
| 2001/0056225 A1 | 12/2001 | DeVito |
| 2002/0056087 A1 | 5/2002 | Berezowski et al. |
| 2002/0056124 A1 | 5/2002 | Hay |
| 2002/0065826 A1 | 5/2002 | Bell et al. |
| 2002/0072952 A1 | 6/2002 | Hamzy et al. |
| 2002/0103429 A1 | 8/2002 | deCharms |
| 2002/0111796 A1 | 8/2002 | Nemoto |
| 2002/0143627 A1 | 10/2002 | Barsade et al. |
| 2002/0154833 A1 | 10/2002 | Koch et al. |
| 2002/0182574 A1 | 12/2002 | Freer |
| 2002/0188217 A1 | 12/2002 | Farwell |
| 2003/0003433 A1 | 1/2003 | Carpenter et al. |
| 2003/0036955 A1 | 2/2003 | Tanaka et al. |
| 2003/0037333 A1 | 2/2003 | Ghashghai et al. |
| 2003/0063780 A1 | 4/2003 | Gutta et al. |
| 2003/0065524 A1 | 4/2003 | Giacchetti et al. |
| 2003/0076369 A1 | 4/2003 | Resner |
| 2003/0081834 A1 | 5/2003 | Philomin et al. |
| 2003/0093784 A1 | 5/2003 | Dimitrova et al. |
| 2003/0126593 A1 | 7/2003 | Mault |
| 2003/0131351 A1 | 7/2003 | Shapira |
| 2003/0153841 A1 | 8/2003 | Kilborn et al. |
| 2003/0165270 A1 | 9/2003 | Endrikhovski et al. |
| 2003/0172374 A1 | 9/2003 | Vinson et al. |
| 2003/0208754 A1 | 11/2003 | Sridhar et al. |
| 2004/0001616 A1 | 1/2004 | Gutta et al. |
| 2004/0018476 A1 | 1/2004 | Ladue |
| 2004/0039268 A1 | 2/2004 | Barbour et al. |
| 2004/0072133 A1 | 4/2004 | Kullok et al. |
| 2004/0101212 A1 | 5/2004 | Fedorovskaya et al. |
| 2004/0117831 A1 | 6/2004 | Ellis et al. |
| 2004/0187167 A1 | 9/2004 | Maguire et al. |
| 2004/0193068 A1 | 9/2004 | Burton et al. |
| 2004/0208496 A1 | 10/2004 | Pilu |
| 2004/0230989 A1 | 11/2004 | Macey et al. |
| 2004/0267141 A1 | 12/2004 | Amano et al. |
| 2005/0010087 A1 | 1/2005 | Banet |
| 2005/0010637 A1 | 1/2005 | Dempski et al. |
| 2005/0043646 A1 | 2/2005 | Viirre et al. |
| 2005/0043774 A1 | 2/2005 | Devlin et al. |
| 2005/0045189 A1 | 3/2005 | Jay |
| 2005/0066307 A1 | 3/2005 | Patel et al. |
| 2005/0071865 A1 | 3/2005 | Martins |
| 2005/0079474 A1 | 4/2005 | Lowe |
| 2005/0097594 A1 | 5/2005 | O'Donnell et al. |
| 2005/0113656 A1 | 5/2005 | Chance |
| 2005/0132401 A1 | 6/2005 | Boccon-Gibod et al. |
| 2005/0149964 A1 | 7/2005 | Thomas et al. |
| 2005/0154290 A1 | 7/2005 | Langleben |
| 2005/0172311 A1 | 8/2005 | Hjelt et al. |
| 2005/0177058 A1 | 8/2005 | Sobell |
| 2005/0216243 A1 | 9/2005 | Graham et al. |
| 2005/0223237 A1 | 10/2005 | Barletta et al. |
| 2005/0261980 A1 | 11/2005 | Hadi |
| 2005/0262542 A1 | 11/2005 | DeWeese et al. |
| 2005/0267798 A1 | 12/2005 | Panara |
| 2005/0288954 A1 | 12/2005 | McCarthy et al. |
| 2005/0289582 A1 | 12/2005 | Tavares et al. |
| 2006/0009702 A1 * | 1/2006 | Iwaki et al. ................ 600/520 |
| 2006/0010470 A1 | 1/2006 | Kurosaki et al. |
| 2006/0031882 A1 | 2/2006 | Swix et al. |
| 2006/0149337 A1 | 7/2006 | John |
| 2006/0176289 A1 | 8/2006 | Horn |
| 2006/0190822 A1 | 8/2006 | Basson et al. |
| 2006/0190966 A1 | 8/2006 | McKissick et al. |
| 2006/0218046 A1 | 9/2006 | Carfi et al. |
| 2006/0256133 A1 | 11/2006 | Rosenberg |
| 2006/0257834 A1 | 11/2006 | Lee et al. |
| 2006/0258926 A1 | 11/2006 | Ali et al. |
| 2006/0259371 A1 | 11/2006 | Perrier et al. |
| 2006/0259922 A1 | 11/2006 | Sandgren et al. |
| 2006/0277102 A1 | 12/2006 | Agliozzo |
| 2006/0293921 A1 | 12/2006 | McCarthy et al. |
| 2007/0016096 A1 | 1/2007 | McNabb |
| 2007/0050256 A1 | 3/2007 | Walker et al. |
| 2007/0053513 A1 | 3/2007 | Hoffberg |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066914 A1 | 3/2007 | Le et al. |
| 2007/0066916 A1 * | 3/2007 | Lemos ........................ 600/558 |
| 2007/0067305 A1 | 3/2007 | Ives |
| 2007/0101360 A1 | 5/2007 | Gutta et al. |
| 2007/0112460 A1 | 5/2007 | Kiselik |
| 2007/0116037 A1 | 5/2007 | Moore |
| 2007/0136753 A1 | 6/2007 | Bovenschulte |
| 2007/0150916 A1 | 6/2007 | Begole et al. |
| 2007/0162505 A1 | 7/2007 | Cecchi et al. |
| 2007/0168461 A1 | 7/2007 | Moore |
| 2007/0173733 A1 | 7/2007 | Le et al. |
| 2007/0179396 A1 | 8/2007 | Le et al. |
| 2007/0184420 A1 | 8/2007 | Mathan et al. |
| 2007/0192168 A1 | 8/2007 | Van Luchene |
| 2007/0192785 A1 | 8/2007 | Pellinat et al. |
| 2007/0209047 A1 | 9/2007 | Hallberg et al. |
| 2007/0214471 A1 * | 9/2007 | Rosenberg ...................... 725/24 |
| 2007/0225585 A1 | 9/2007 | Washbon et al. |
| 2007/0235716 A1 | 10/2007 | Delic et al. |
| 2007/0238945 A1 | 10/2007 | Delic et al. |
| 2007/0240180 A1 | 10/2007 | Shanks et al. |
| 2007/0250846 A1 | 10/2007 | Swix et al. |
| 2007/0265507 A1 | 11/2007 | De Lemos |
| 2007/0282566 A1 | 12/2007 | Whitlow et al. |
| 2008/0065468 A1 * | 3/2008 | Berg et al. ...................... 705/10 |
| 2008/0091512 A1 | 4/2008 | Marci et al. |
| 2008/0144882 A1 | 6/2008 | Leinbach et al. |
| 2008/0147488 A1 | 6/2008 | Tunick et al. |
| 2008/0159365 A1 | 7/2008 | Dubocanin et al. |
| 2008/0162182 A1 | 7/2008 | Cazares et al. |
| 2008/0177197 A1 * | 7/2008 | Lee et al. ...................... 600/545 |
| 2008/0195471 A1 | 8/2008 | Dube et al. |
| 2008/0211768 A1 | 9/2008 | Breen et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 * | 9/2008 | Lee et al. ......................... 725/10 |
| 2008/0275830 A1 * | 11/2008 | Greig .............................. 706/21 |
| 2008/0306398 A1 | 12/2008 | Uchiyama et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0062629 A1 | 3/2009 | Pradeep et al. |
| 2009/0062679 A1 | 3/2009 | Tan et al. |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0070798 A1 | 3/2009 | Lee et al. |
| 2009/0082643 A1 | 3/2009 | Pradeep et al. |
| 2009/0082692 A1 | 3/2009 | Hale et al. |
| 2009/0083129 A1 | 3/2009 | Pradeep et al. |

(56) References Cited

U.S. PATENT DOCUMENTS

| | | | |
|---|---|---|---|
| 2009/0088610 | A1 | 4/2009 | Lee et al. |
| 2009/0094286 | A1 | 4/2009 | Lee et al. |
| 2009/0094627 | A1 | 4/2009 | Lee et al. |
| 2009/0094628 | A1 | 4/2009 | Lee et al. |
| 2009/0094629 | A1 | 4/2009 | Lee et al. |
| 2009/0105576 | A1 | 4/2009 | Do et al. |
| 2009/0112077 | A1 | 4/2009 | Nguyen et al. |
| 2009/0112117 | A1 | 4/2009 | Rewari |
| 2009/0132441 | A1 | 5/2009 | Muller et al. |
| 2009/0133047 | A1 | 5/2009 | Lee et al. |
| 2009/0150919 | A1 | 6/2009 | Lee et al. |
| 2009/0153328 | A1 | 6/2009 | Otani et al. |
| 2009/0156925 | A1 | 6/2009 | Jin et al. |
| 2009/0164132 | A1 | 6/2009 | Jung et al. |
| 2009/0214060 | A1 | 8/2009 | Chuang et al. |
| 2009/0221928 | A1 | 9/2009 | Einav et al. |
| 2009/0222330 | A1 | 9/2009 | Leinbach |
| 2009/0253996 | A1* | 10/2009 | Lee et al. .................. 600/544 |
| 2009/0271294 | A1 | 10/2009 | Hadi |
| 2009/0300672 | A1 | 12/2009 | Van Gulik |
| 2009/0318773 | A1 | 12/2009 | Jung et al. |
| 2009/0327068 | A1 | 12/2009 | Pradeep et al. |
| 2009/0328089 | A1 | 12/2009 | Pradeep et al. |
| 2010/0004977 | A1 | 1/2010 | Marci et al. |
| 2010/0094702 | A1 | 4/2010 | Silberstein |
| 2010/0180029 | A1 | 7/2010 | Fourman |
| 2011/0153423 | A1 | 6/2011 | Elvekrog et al. |
| 2012/0321271 | A1* | 12/2012 | Baldwin et al. .............. 386/201 |
| 2013/0185140 | A1 | 7/2013 | Pradeep et al. |
| 2013/0185141 | A1 | 7/2013 | Pradeep et al. |
| 2013/0185142 | A1 | 7/2013 | Pradeep et al. |
| 2013/0185145 | A1 | 7/2013 | Pradeep et al. |
| 2013/0304540 | A1 | 11/2013 | Pradeep et al. |
| 2013/0332259 | A1 | 12/2013 | Pradeep et al. |
| 2014/0164095 | A1* | 6/2014 | Pradeep ............... A61B 5/0476 705/14.41 |

FOREIGN PATENT DOCUMENTS

| | | |
|---|---|---|
| KR | 10-2001-0104579 | 11/2001 |
| KR | 200422399 | 7/2006 |
| WO | 2005-160805 | 12/2003 |
| WO | 2008-030831 | 3/2008 |
| WO | 2008-064431 | 6/2008 |
| WO | 2008-121651 | 10/2008 |
| WO | 2008-137579 | 11/2008 |
| WO | 2008-137581 | 11/2008 |
| WO | 2008-141340 | 11/2008 |
| WO | 2008-154410 | 12/2008 |
| WO | 2009-018374 | 2/2009 |
| WO | 2006-305334 | 11/2009 |

OTHER PUBLICATIONS

Ho et al. WO 2008/030831 A2.*
First Office Action, issued by the State Intellectual Property Office of P.R. China in connection with Patent Application No. 200880123640.4, on Feb. 29, 2012, 8 pages.
Notice of Allowance, issued by the United States Patent and Trademark Office in connection with U.S. Appl. No. 12/244,752, on May 29, 2012, 17 pages.
Notice of Allowance, issued by the United States Patent and Trademark Office in connection with U.S. Appl. No. 12/244,751, on Jun. 12, 2012, 18 pages.
Notice of Allowance, issued by the United States Patent and Trademark Office in connection with U.S. Appl. No. 12/244,752, on Jul. 26, 2012, 7 pages.
Notice of Allowance, issued by the United States Patent and Trademark Office in connection with U.S. Appl. No. 12/244,752, on Sep. 7, 2012, 16 pages.
Form PCT/ISA/220, PCT/US07/15019, "PCT Notification of Transmittal of the International Search Report and the Written Opinion of the International Searching Authority, or the Declaration," 1 pg.
Form PCT/ISA/210, PCT/US07/15019, "PCT International Search Report," 2 pgs.
Form PCT/ISA/237, PCT/US07/15019, "PCT Written Opinion of the International Searching Authority," 5 pgs.
Form PCT/IB/326, PCT/US07/015019, "Notification Concerning Transmittal of International Preliminary Report on Patentability."
Form PCT/IB/373, PCT/US07/15019, "International Preliminary Report on Patentability."
Form PCT/ISA/220, PCT/US07/14955, "PCT Notification of Transmittal of the International Search Report and the Written Opinion of the International Searching Authority, or the Declaration," 1 pg.
Form PCT/ISA/210, PCT/US07/14955, "PCT International Search Report," 2 pgs.
Form PCT/ISA/237, PCT/US07/14955, "PCT Written Opinion of the International Searching Authority," 6 pgs.
Form PCT/IB/326, PCT/US07/14955, "Notification Concerning Transmittal of International Preliminary Report on Patentability." 1 page.
Form PCT/IB/373, PCT/US07/14955, "International Preliminary Report on Patentability." 1 page.
Form PCT/ISA/220, PCT/US07/16796, "PCT Notification of Transmittal of the International Search Report and the Written Opinion of the International Searching Authority, or the Declaration," 1 pg.
Form PCT/ISA/210, PCT/US07/16796, "PCT International Search Report," 2 pgs.
Form PCT/ISA/237, PCT/US07/16796, "PCT Written Opinion of the International Searching Authority," 6 pgs.
Form PCT/IB/326, PCT/US07/16796, "Notification Concerning Transmittal of International Preliminary Report on Patentability." 1 page.
Form PCT/IB/373, PCT/US07/16796, "International Preliminary Report on Patentability." 1 page.
Form PCT/ISA/220, PCT/US06/31569, "PCT Notification of Transmittal of the International Search Report and the Written Opinion of the International Searching Authority, or the Declaration," 1 pg.
Form PCT/ISA/210, PCT/US06/31569, "PCT International Search Report," 3 pgs.
Form PCT/ISA/237, PCT/US06/31569, "PCT Written Opinion of the International Searching Authority," 6 pgs.
Form PCT/IB/326, PCT/US06/31569, "Notification Concerning Transmittal of International Preliminary Report on Patentability." 1 page.
Form PCT/IB/373, PCT/US06/31569, "International Preliminary Report on Patentability." 1 page.
Form PCT/ISA/220, PCT/US07/20714, "PCT Notification of Transmittal of the International Search Report and the Written Opinion of the International Searching Authority, or the Declaration," 1 pg.
Form PCT/ISA/210, PCT/US07/20714, "PCT International Search Report," 2 pgs.
Form PCT/ISA/237, PCT/US07/20714, "PCT Written Opinion of the International Searching Authority," 6 pgs.
Form PCT/IB/326, PCT/US07/20714, "Notification Concerning Transmittal of International Preliminary Report on Patentability." 1 page.
Form PCT/IB/373, PCT/US07/20714, "International Preliminary Report on Patentability." 1 page.
Form PCT/ISA/220, PCT/US07/17764, "PCT Notification of Transmittal of the International Search Report and the Written Opinion of the International Searching Authority, or the Declaration," 1 pg.
Form PCT/ISA/210, PCT/US07/17764, "PCT International Search Report," 2 pgs.
Form PCT/ISA/237, PCT/US07/17764, "PCT Written Opinion of the International Searching Authority," 7 pgs.
Form PCT/IB/326, PCT/US07/17764, "Notification Concerning Transmittal of International Preliminary Report on Patentability." 1 page.
Form PCT/IB/373, PCT/US07/17764, "International Preliminary Report on Patentability." 1 page.
Form PCT/ISA/220, PCT/US07/20713, "PCT Notification of Transmittal of the International Search Report and the Written Opinion of the International Searching Authority, or the Declaration," 1 pg.
Form PCT/ISA/210, PCT/US07/20713, "PCT International Search Report," 2 pgs.

(56) References Cited

OTHER PUBLICATIONS

Form PCT/ISA/237, PCT/US07/20713, "PCT Written Opinion of the International Searching Authority," 5 pgs.
Form PCT/IB/326, PCT/US07/20713, "Notification Concerning Transmittal of International Preliminary Report on Patentability." 1 page.
Form PCT/IB/373, PCT/US07/20713, "International Preliminary Report on Patentability." 1 page.
Form PCT/ISA/220, PCT/US08/09110, "PCT Notification of Transmittal of the International Search Report and the Written Opinion of the International Searching Authority, or the Declaration," 1 pg.
Form PCT/ISA/210, PCT/US08/09110, "PCT International Search Report," 3 pgs.
Form PCT/ISA/237, PCT/US08/09110, "PCT Written Opinion of the International Searching Authority," 4 pgs.
Form PCT/ISA/220, PCT/US08/75640, "PCT Notification of Transmittal of the International Search Report and the Written Opinion of the International Searching Authority, or the Declaration," 1 pg.
Form PCT/ISA/210, PCT/US08/75640, "PCT International Search Report," 2 pgs.
Form PCT/ISA/237, PCT/US08/75640, "PCT Written Opinion of the International Searching Authority," 3 pgs.
Form PCT/ISA/220, PCT/US08/78633, "PCT Notification of Transmittal of the International Search Report and the Written Opinion of the International Searching Authority, or the Declaration," 1 pg.
Form PCT/ISA/210, PCT/US08/78633, "PCT International Search Report," 2 pgs.
Form PCT/ISA/237, PCT/US08/78633, "PCT Written Opinion of the International Searching Authority," 6 pgs.
Form PCT/ISA/220, PCT/US08/82147, "PCT Notification of Transmittal of the International Search Report and the Written Opinion of the International Searching Authority, or the Declaration," 1 pg.
Form PCT/ISA/210, PCT/US08/82147, "PCT International Search Report," 2 pgs.
Form PCT/ISA/237, PCT/US08/82147, "PCT Written Opinion of the International Searching Authority," 13 pgs.
Form PCT/ISA/220, PCT/US08/82149, "PCT Notification of Transmittal of the International Search Report and the Written Opinion of the International Searching Authority, or the Declaration," 1 pg.
Form PCT/ISA/210, PCT/US08/82149, "PCT International Search Report," 2 pgs.
Form PCT/ISA/237, PCT/US08/82149, "PCT Written Opinion of the International Searching Authority," 14 pgs.
Form PCT/ISA/220, PCT/US08/75651, "PCT Notification of Transmittal of the International Search Report and the Written Opinion of the International Searching Authority, or the Declaration," 1 pg.
Form PCT/ISA/210, PCT/US08/75651, "PCT International Search Report," 2 pgs.
Form PCT/ISA/237, PCT/US08/75651, "PCT Written Opinion of the International Searching Authority," 9 pgs.
Form PCT/ISA/220, PCT/US08/85723, "PCT Notification of Transmittal of the International Search Report and the Written Opinion of the International Searching Authority, or the Declaration," 1 pg.
Form PCT/ISA/210, PCT/US08/85723, "PCT International Search Report," 2 pgs.
Form PCT/ISA/237, PCT/US08/85723, "PCT Written Opinion of the International Searching Authority," 7 pgs.
Form PCT/ISA/220, PCT/US08/85203, "PCT Notification of Transmittal of the International Search Report and the Written Opinion of the International Searching Authority, or the Declaration," 1 pg.
Form PCT/ISA/210, PCT/US08/85203, "PCT International Search Report," 2 pgs.
Form PCT/ISA/237, PCT/US08/85203, "PCT Written Opinion of the International Searching Authority," 6 pgs.
Form PCT/ISA/220, PCT/US08/75649, "PCT Notification of Transmittal of the International Search Report and the Written Opinion of the International Searching Authority, or the Declaration," 1 pg.
Form PCT/ISA/210, PCT/US08/75649, "PCT International Search Report," 3 pgs.
Form PCT/ISA/237, PCT/US08/75649, "PCT Written Opinion of the International Searching Authority," 5 pgs.
Technology Platform: SmartShirt + Eye-Tracking Innerscope Research, Mar. 2007.
Egner, Tobias; Emilie Strawson, and John H. Gruzelier, "EEG Signature and Phenomenology of Alpha/theta Neurofeedback Training Versus Mock Feedback." Applied Psychophysiology and Biofeedback. vol. 27, No. 4. Dec. 2002.
Clarke, Adam R. et al., EEG Analysis of Children with Attention-Deficit/Hyperactivity Disorder and Comorbid Reading Disabilities, Journal of Learning Disabilities, vol. 35, No. 3, (May-Jun. 2002), pp. 276-285.
Carter, R., "Mapping the Mind" 1998 p. 182 University of California Press, Berkley.
Harmony et al. (2004) Specific EEG frequencies signal general common cognitive processes as well as specific tasks processes in man. Int. Journal of Psychophysiology 53(3): 207-16.
Klimesch, W., Schimke, H., Schwaiger, J. (1994) Episodic and semantic memory: an analysis in the EEG theta and alpha band. Electroencephalography Clinical Neurophysiology.
Mizuhara, H.,Wang LQ, Kobayashi, K., Yamaguchi, Y., (2004) A long range cortical network emerging with theta oscillation in mental task. Neuroreport 15(8): 1233-1238.
Selden, G (1981) "Machines that Read Minds." Science Digest, October.
Willis, M. & Hodson, V.; Discover Your Child's Learning Style: Children Learn in Unique Ways-Here's the Key to Every Child's Learning Success, Prime Publishing. Roseville, CA.
Wise, A (1996) The High Performance Mind, Mastering Brainwaves for Insight, Healing and Creativity. G.P. Putnam's Son, New York. pp. 13-15; 20-22; 143-156.
Wise, A (1996) The High Performance Mind, Mastering Brainwaves for Insight, Healing and Creativity. G.P. Putnam's Son, New York. pp. 156-158; 165-170; 186-187, 189-192.
El-Bab, M. (2001) Cognitive event related potentials during a learning task. Doctoral Dissertation, Faculty of Medicine, University of Southampton, UK.
Gevins et al. (1997) High resolution EEG mapping of cortical activation related to a working memory, Cereb Cortex. 7: 374-385.
Hughes, J.R. & John, E.R. (1999) Conventional and Quantitative Electroencephalography in Psychiatry. Journal of Neuropsychiatry and Clinical Neurosciences. vol. 11(2): 190-208.
Government of Nefoundland and Labrador, "Budget 1996 Online," Who Responded graph, available at http://www.budget.gov.nl.ca/buget96/who.gif, 1996 (1 page).
Oxford English Dictionary, Definition of "Question," retrieved from oed.com on Nov. 21, 2011.
Office Action, issued by the United States Patent and Trademark Office in connection with U.S. Appl. No. 12/244,748, on Dec. 17, 2010, 18 pages.
Office Action, issued by the United States Patent and Trademark Office in connection with U.S. Appl. No. 12/244,751, on Feb. 7, 2011, 18 pages.
Office Action, issued by the United States Patent and Trademark Office in connection with U.S. Appl. No. 12/244,752, on Feb. 18, 2011, 14 pages.
Office Action, issued by the United States Patent and Trademark Office in connection with U.S. Appl. No. 12/326,016, on Mar. 21, 2011, 23 pages.
Office Action, issued by the United States Patent and Trademark Office in connection with U.S. Appl. No. 12/244,737, on May 16, 2011, 16 pages.
Notice of Allowance, issued by the United States Patent and Trademark Office in connection with U.S. Appl. No. 12/244,748, on Aug. 30, 2011, 8 pages.
Final Rejection, issued by the United States Patent and Trademark Office in connection with U.S. Appl. No. 12/244,751, on Sep. 7, 2011, 19 pages.
Office Action, issued by the United States Patent and Trademark Office in connection with U.S. Appl. No. 12/263,350, on Oct. 24, 2011, 17 pages.

(56) References Cited

OTHER PUBLICATIONS

Final Rejection, issued by the United States Patent and Trademark Office in connection with U.S. Appl. No. 12/244,752, on Nov. 23, 2011, 15 pages.
Final Rejection, issued by the United States Patent and Trademark Office in connection with U.S. Appl. No. 12/244,737, on Nov. 29, 2011, 12 pages.
Final Rejection, issued by the United States Patent and Trademark Office in connection with U.S. Appl. No. 12/326,016, on Nov. 30, 2011, 23 pages.
Lewis et al., "Market Researchers make Increasing use of Brain Imaging," ACNR, vol. 5, No. 3, pp. 36-37, (Jul./Aug. 2005), 2 pages.
Aaker et al., "Warmth in Advertising: Measurement, Impact, and Sequence Effects," Journal of Consumer Research, vol. 12, No. 4, pp. 365-381, (Mar. 1986), 17 pages.
Belch et al., "Psychophysiological and cognitive Response to Sex in Advertising," Advances in Consumer Research, vol. 9, pp. 424-427, (1982), 6 pages.
Ruchkin et al., "Modality-specific processing streams in verbal working memory: evidence from spatio-temporal patterns of brain activity," Cognitive Brain Research, vol. 6, pp. 95-113, Elsevier, (1997), 19 pages.
Page et al., "Cognitive Neuroscience, Marketing and Research," Congress 2006—Foresight—The Predictive Power of Research Conference Papers, ESOMAR Publications, (Sep. 17, 2006), 25 pages.
Braeutigam, "Neuroeconomics-From neural systems to economic behavior," Brain Research Bulletin, vol. 67, pp. 355-360, Elsevier, (2005), 6 pages.
Lee et al., "What is 'neuromarketing'? A discussion and agenda for future research," International Journal of Psychophysiology, vol. 63, pp. 199-204, Elsevier (2006), 6 pages.
Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.
Desmet, "Measuring Emotion: Development and Application of an Instrument to Measure Emotional Responses to Products," to be published in Funology: From Usability to Enjoyment, pp. 111-123, Kluwer Academic Publishers, (Blythe et al., eds., 2004), 13 pages.
Bagozzi et al., "The Role of Emotions in Marketing," Journal of the Academy of Marketing Science, vol. 27, No. 2, pp. 184-206, Academy of Marketing Science (1999), 23 pages.
Blakeslee, "If You Have a 'Buy Button' in Your Brain, What Pushes It?" The New York Times, www.nytimes.com, (Oct. 19, 2004), 3 pages.
Ziegenfuss, "Neuromarketing: Advertising Ethical & Medical Technology," The Brownstone Journal, vol. XII, Boston University, pp. 69-73, (May 2005), 5 pages.
Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.
Hazlett, et al., "Emotional Response to Television Commercials: Facial EMG vs. Self-Report," Journal of Advertising Research, (Apr. 1999), 17 pages.
Makeig, et al., "Mining event-related brain dynamics," TRENDS in Cognitive Sciences, vol. 8, No. 5, (May 2004), www.sciencedirect.com, 7 pages.
Hopf, et al., "Neural Sources of Focused Attention in Visual Search," Cerebral Cortex, 10:1233-1241, Oxford University Press, (Dec. 2000), 9 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.
Haq, "This Is Your Brain on Advertising," BusinessWeek, Market Research, (Oct. 8, 2007), 3 pages.

Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.
Gazzaley, et al., "Top-down Enhancements and Suppression of the Magnitude Speed of Neural Activity," Massachusetts Institute of Technology, Journal of Cognitive Neuroscience, No. 17:3, (2005), 11 pages.
Engel, et al., "Dynamic Predictions: Oscillations and Synchrony in Top-Down Processing," Macmilliam Magazines Ltd, vol. 2, (Oct. 2001) www.nature.com/reviews/neuro, 13 pages.
Fries, "A Mechanism for cognitive dynamics: neuronal communication through neuronal coherence," TRENDS in Cognitive Sciences vol. 9 No. 10 (Oct. 2005) www.sciencedirect.com, 7 pages.
Notice of Allowance, issued by the United States Patent and Trademark Office in connection with U.S. Appl. No. 13/659,592, on Dec. 24, 2014, 65 pages.
Beaver, John D., et al., "Individual Differences in Reward Drive Predict Neural Responses to Images of Food", J. of Neuroscience, (May 10, 2006), 5160-5166, 7 pages.
Cassanello, Carlos R., et al., "Neuronal Responses to Moving Targets in Monkey Frontal Eye Fields", J Neurophysiol (Sep. 2008), 1544-1556, 16 pages.
Darrow, Chester, "Psychological and psychophysiological significance of the electroencephalogram," Psychological Review (May 1947) 157-168, 12 pages.
Duchowski, "A Breadth-First Survey of Eye-tracking Applications," Beahavior Research Methods, Instruments, and Computers (Nov. 2002), 455-470, 16 pages.
Ekman, P , Friesen, W., Measuring Facial Movement, Environmental Psychology and Nonverbal Behavior, 1 (1) (Fall 1976), pp. 56-75, 20 pages.
Enghoff, Sigurd, Thesis: "Moving ICA and Time-Frequency Analysis in Event-Related EEG Studies of Selective Attention," Technical University of Denmark, (Dec. 1999), 54 pages.
Ekman, P , Friesen, W.V., *Facial Action Coding System: A Technique for Measurement of Facial Movement*, Consulting Psychologists Press, Palo Alto, Calif (1978).
Ekman, P , Friesen, W., *Unmasking the Face—A Guide to Recognizing Emotions from Facial Clues*, Prentice-Hall, Inc., Englewood Cliffs, N.J. (1979).
Ekman, P , Friesen, W., Ancoli, S., Facial Signs of Emotional Experience, J. Personality & Social Psychology, 39(6) (Dec. 1980), pp. 1125-1134, 10 pages.
Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.
Izard, C. E., *The Maximally Discriminative Facial Movement Coding System*, (Rev. ed.), Instructional Resources Center, University of Delaware, Newark, Del. (1983).
Izard, C., Dougherty, L., Hembree, E., *A System for Identifying Affect Expressions by Holistic Judgments (AFFEX)*, Instructional Resources Center, University of Delaware, Newark, Del. (1983).
Jaimes, A., Sebe, N., Multimodal Human-Computer Interaction: A Survey, Computer Vision and Image Understanding 108 (Oct.-Nov. 2007), pp. 116-134, 19 pages.
Jia, X., Nixon, M.S., Extending the Feature Set for Automatic Face Recognition, International Conference on Image Processing and Its Applications (Apr. 7-9, 1992), 6 pages.
Lisetti, C., Nasoz, F., Using Noninvasive Wearable Computers to Recognize Human Emotions from Physiological Signals, EURASIP J. Applied Signal Processing, 11 (Sep. 2004), pp. 1672-1687, 16 pages.
Mehta, A. et al., "Reconsidering Recall and Emotion in Advertising", Journal of Advertising Research, (Mar. 2006), 49-56, 9 pages.
Rothschild et al., "Predicting Memory for Components of TV Commercials from EEG," Journal of Consumer Research (Mar. 1990), p. 472-478, 8 pages.
Shandlen, Michael N. et al., "A Computational Analysis of the Relationship between Neuronal and Behavioral Responses to Visual Motion", The Journal of Neuroscience, (Feb. 15, 1996) 1486-1510, 25 pages.

(56) References Cited

OTHER PUBLICATIONS

Non-Final Office Action, issued by the United States Patent and Trademark Office in connection with U.S. Appl. No. 14/673,077, on Jan. 7, 2016, 76 pages.
Landau et al., "Different Effects of Voluntary and Involunatry Attention on EEG Activity in the Gamma Band," The Journal of Neuroscience 27(44), Oct. 31, 2007, pp. 11986-11990, 5 pages.
Final Office Action, issued by the United States Patent and Trademark Office in connection with U.S. Appl. No. 14/673,077, on Jun. 9, 2016, 53 pages.
M. Corbetta et al., "Control of Goal-Directed and Stimulus-Driven Attention in the Brain," Nature Reviews Neuroscience, vol. 3, pp. 201-15 (Mar. 2002), 15 pages.
Becker, S. "A Study of Web Usability for Older Adults Seeking Online Health Resources," ACM Transactions on Computer-Human Interaction, vol. 11, No. 4, pp. 387-406 (Dec. 2004), 20 pages.
Advisory Action, issued by the United States Patent and Trademark Office in connection with U.S. Appl. No. 14/673,077, on Aug. 30, 2016, 11 pages.
Notice of Allowance, issued by the United States Patent and Trademark Office in connection with U.S. Appl. No. 14/673,077, on Sep. 23, 2016, 55 pages.

\* cited by examiner

SYSTEMS AND METHODS PROVIDING EN MASS COLLECTION AND CENTRALIZED PROCESSING OF PHYSIOLOGICAL RESPONSES FROM VIEWERS

RELATED APPLICATION

This patent claims the benefit of U.S. Patent Application No. 60/984,260, filed Oct. 31, 2007.

This patent also claims the benefit of U.S. Patent Application No. 60/984,268, filed Oct. 31, 2007.

This patent is related to U.S. patent application Ser. Nos. 11/804,517, 11/804,555, 11/779,814, 11/500,678, 11/845,993, 11/835,634, 11/846,068, 12/180,510, 12/206,676, 12/206,700, 12/206,702, 12/244,737, 12/244,748, 12/244,751, 12/244,752, 12/263,350, 12/325,016, 13/252,910, 11/430,555, 11/681,265, 11/852,189, and 11/959,399.

TECHNICAL FIELD

This invention relates to the field of collection and analysis of physiological responses from viewers of media instances.

BACKGROUND

A key to making a high performing media instance is to make sure that every event in the media elicits the desired responses from viewers, not responses very different from what the creator of the media expected. Herein, the media instance can be but is not limited to, a video game, an advertisement clip, a movie, a computer application, a printed media (e.g., a magazine), a website, an online advertisement, a recorded video, a live performance of media, and other types of media.

Physiological data, which includes but is not limited to heart rate, brain waves, electroencephalogram (EEG) signals, blink rate, breathing, motion, muscle movement, galvanic skin response and any other response correlated with changes in emotion of a viewer of a media instance, can give a trace (e.g., a line drawn by a recording instrument) of the viewer's responses while he/she is watching the media instance. The physiological data can be measured by one or more physiological sensors, each of which can be but is not limited to, an electroencephalogram, an accelerometer, a blood oxygen sensor, a galvanometer, an electromygraph, skin temperature sensor, breathing sensor, and any other physiological sensor.

It is well established that physiological data in the human body of a viewer has been shown to correlate with the viewer's change in emotions. Thus, from the measured "low level" physiological data, "high level" (i.e., easier to understand, intuitive to look at) physiological responses from the viewers of the media instance can be created. An effective media instance that connects with its audience/viewers is able to elicit the desired emotional response. Here, the high level physiological responses include, but are not limited to, liking (valence)-positive/negative responses to events in the media instance, intent to purchase or recall, emotional engagement in the media instance, thinking—amount of thoughts and/or immersion in the experience of the media instance, adrenaline—anger, distraction, frustration, cognition, stress, and other emotional experiences to events in the media instance.

Collecting physiological responses to a media instance from the viewers typically requires bringing the viewers/testers to a testing facility, fitting them with multiple physiological sensors, and recording the physiological data from the viewers via various testing equipment while they are watching the media instance. One problem with such testing process is that only a small number of people can be tested for a specific media instance due to the limited capacity and/or availability of the testing facilities as well as the professionals required to administer the testing. The cost for such testing can also be quite expensive and the results may be less than accurate due to the limited scope of the testing. Furthermore, most conventional testing is performed in sterile and unrealistic environments that can lead to results that are less than ideal.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

DETAILED DESCRIPTION

Figure 1A:
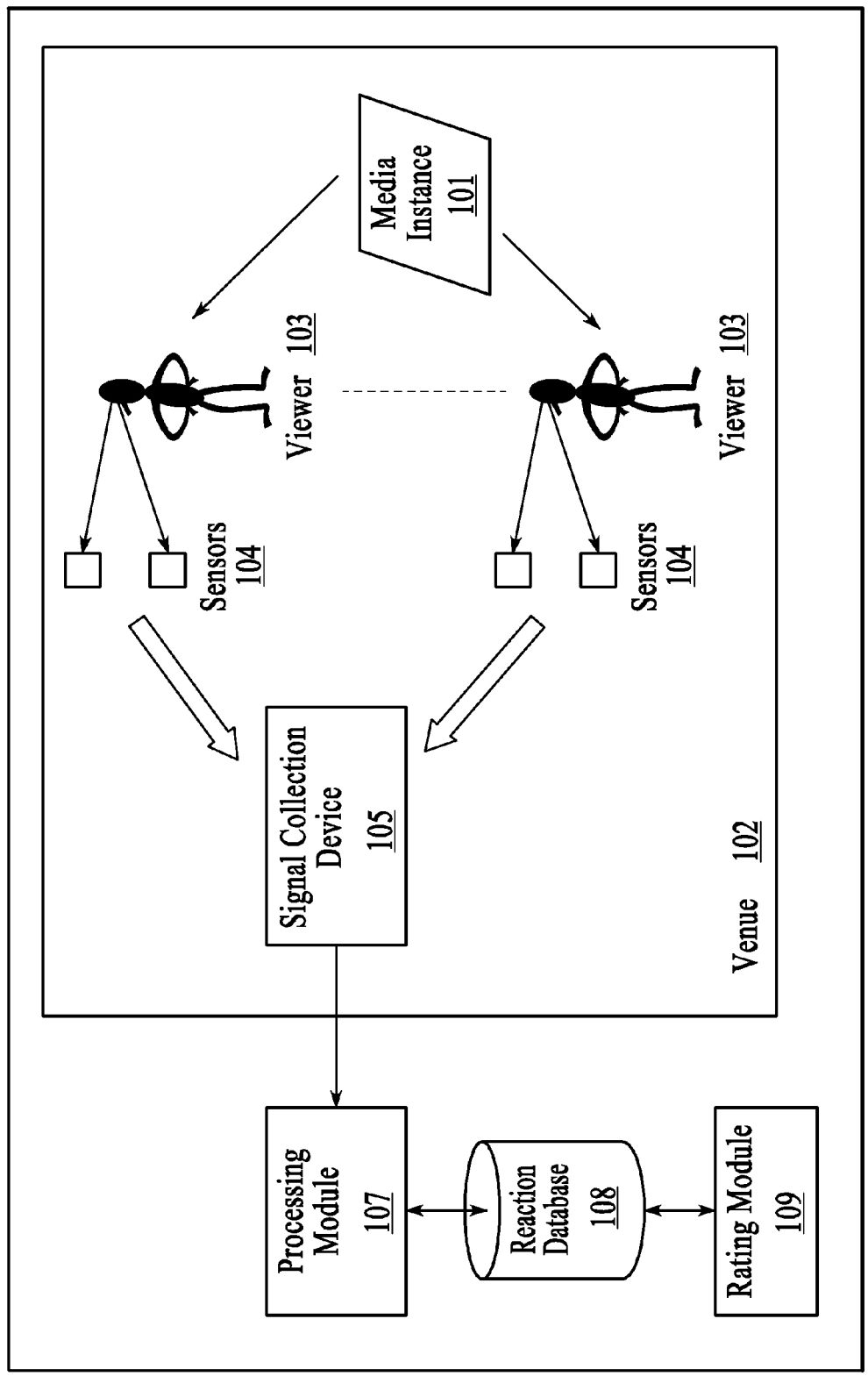
FIG. 1A is a block diagram of a system to support gathering of physiological responses from viewers in a group setting, under an embodiment.

Embodiments described herein enable "in situ" sensing, which collects and analyzes physiological responses from a large group of viewers/audiences who watch a same media instance together at a single venue. Each of the group of viewers is fitted with one or more physiological sensors with wireless transmission capabilities to communicate with a signal collection device at or near the venue. The signal collection device is operable to collect the physiological data of the viewers from the physiological sensors, and transmit the physiological data to a processing module at another location over a network for storage and further analysis. Such an "in situ" sensing approach achieves much more accurate physiological data and analysis of responses from the group of viewers than any other approach that senses each of the viewers one at a time, because the "in situ" approach inherently takes into account the impact of the dynamics of the group of viewers on each individual viewer's physiological responses for the analysis of the media instance.

Embodiments described herein also enable "in persona" sensing for large scale testing of a media instance via distributed collection and centralized processing of physiological data from each of multiple viewers in his/her own setting. Viewers may also be referred to herein as participants and/or users. The physiological data can first be collected from each of the viewers fitted with one or more physiological sensors locally at a location where he/she is watching the media instance. The data collected from the viewers at these distributed locations can then all be transmitted to a centralized location for processing, aggregation, storage, and analysis.

In the following description, numerous specific details are introduced to provide a thorough understanding of, and enabling description for, the embodiments described herein. One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

The invention is illustrated by way of example and not by way of limitation in the figures of the accompanying drawings in which like references indicate similar elements. It should be noted that references to "an" or "one" or "some" embodiment(s) in this disclosure are not necessarily to the same embodiment, and such references mean at least one.

Advertisers, media producers, educators and other relevant parties have long desired to have greater understanding of viewers' reactions to their media products from their targets, customers, clients and pupils in order to tailor their information or media instances to better suit the needs of end users and/or to increase the effectiveness of the media instance created. For a non-limiting example, while television (TV) producers may be more interested in knowing a viewer's responses when he/she is watching the TV program alone at home, movie producers would be most interested in a viewer's reactions to a movie while he/she are watching it in a theater together with other movie goers rather than in his/her home setting. The embodiments taught herein satisfy such needs of the movie producers, which may not be otherwise met by other types of "one at a time" approaches.

The embodiments described herein, generally, automatically distribute media or a media instance for testing to each venue or site using, for example, a network coupling or connection (e.g., internet, local area network, wide area network, etc.). The media is tested on all participants or viewers, regardless of location at or in one or more venues; the testing may be autonomous without an administrator or, in some cases, may use a human administrator. During testing, physiological data is collected from the participants using one or more sensors and a signal collection device. The data is synchronized and packaged for transmission (e.g., packetized, encrypted, compressed, filtered, etc.), and transmitted from the signal collection device to a processing device using a network coupling or connection (e.g., internet, local area network, wide area network, etc.). The processing device derives one or more physiological responses of the viewers based on the physiological data, aggregates and analyzes the derived responses to the media instance from the viewers, and stores the physiological data, the derived physiological responses and/or the analysis results of the aggregated responses. These operations are described in detail below.

FIG. 1A is a block diagram of a system to support gathering of physiological responses from viewers in a group setting, under an embodiment. Although this diagram depicts components as functionally separate, such depiction is merely for illustrative purposes. It will be apparent to those skilled in the art that the components portrayed in this figure can be arbitrarily combined or divided into separate software, firmware and/or hardware components. Furthermore, it will also be apparent to those skilled in the art that such components, regardless of how they are combined or divided, can execute on the same computing device or multiple computing devices, and wherein the multiple computing devices can be connected by one or more networks.

Referring to FIG. 1A, a plurality of viewers 103 may gather in large numbers at a single venue 102 to watch a media instance 101. Here, the venue can be but is not limited to, a cinema, a theater, an opera house, a hall, an auditorium, and any other place where a group of people can gather to watch the media instance. The media instance can be but is not limited to, a movie, a show, a live performance, an opera, and any type of presentation in front group of audiences gathered at the venue. The media instance can also include but is not limited to, a television program, an advertisement clip, a printed media (e.g., a magazine), a website, a video game, a computer application, and any type of media instance suitable for an individual viewing experience, an online advertisement, a recorded video, and other types of media; as it relates to product analysis, the media instance can include a product, product content, content, product information, and media relating to consumer interaction with products or other objects. Each of the viewers 103 wears one or more sensors 104 used to receive, measure and record physiological data from the viewer who is watching and/or interacting with the media instance. Each of the sensors can be one or more of an electroencephalogram, an accelerometer, a blood oxygen sensor, a galvanometer, an electromygraph, and any other physiological sensor. By sensing the exact changes in physiological parameters of a viewer instead of using other easily biased measures of response (e.g., surveys, interviews, etc.), both the physiological data that is recorded and the granularity of such physiological data representing the physiological responses can be recorded instantaneously, thereby providing a more accurate indicator of a viewer reactions to the media instance.

Once the physiological data is measured, the one or more sensors from each of the plurality of viewers may transmit the physiological data via wireless communication to a signal collection device 105 also located at or near the same venue. Here, the wireless communication covering the short range at the venue can be but is not limited to, Bluetooth, Wi-Fi, wireless LAN, radio frequency (RF) transmission, Zigbee, and any other form of short range wireless communication. Once accepting the physiological data from the one or more sensors attached to each of the viewers, the signal collection device pre-processes, processes, organizes, and/or packages the data into a form suitable for transmission, and then transmits the data to a processing module 107 for further processing, storage, and analysis. The processing module 107 can, for example, be located at a remote location that is remote to the venue.

The processing module 107 of an embodiment derives one or more physiological responses based on the physiological data from the viewers, analyzes the derived response in context of group dynamics of the viewers, and stores the physiological data, the derived physiological responses and/or the analysis results of the responses in a reaction database 108 together with the group dynamics of the viewers. Here, the group dynamics of the viewers can include but are not limited to, name, age, gender, race, income, residence, profession, hobbies, activities, purchasing habits, geographic location, education, political views, and other characteristics of the plurality of viewers. Optionally, a rating module 109 is operable to rate the media instance viewed in the group setting based on the physiological responses from the plurality of viewers.

Figure 1B:
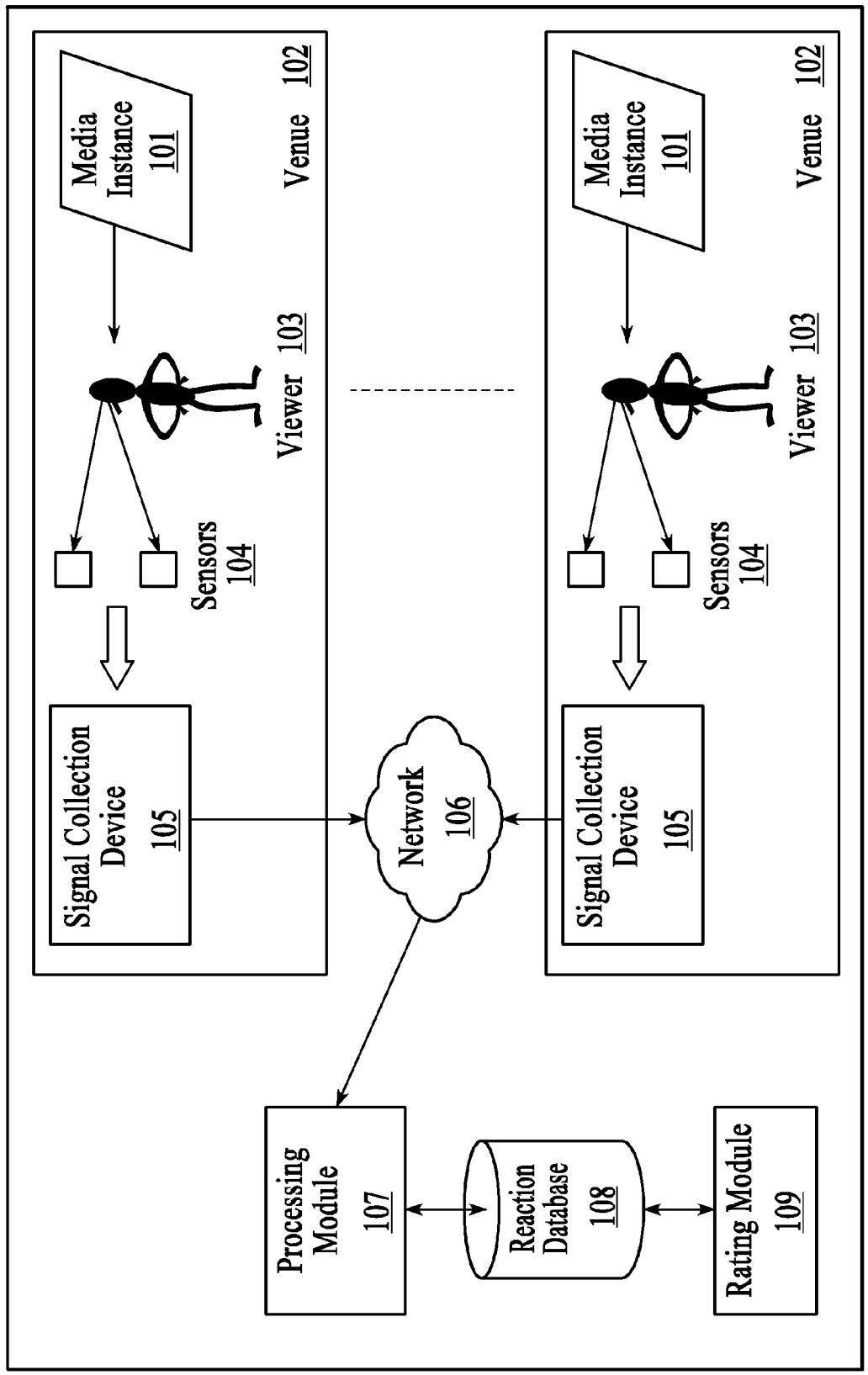
FIG. 1B is a block diagram of a system to support large scale media testing, under an embodiment.

FIG. 1B is a block diagram of a system to support large scale media testing, under an embodiment. Although this diagram depicts components as functionally separate, such depiction is merely for illustrative purposes. It will be apparent to those skilled in the art that the components portrayed in this figure can be arbitrarily combined or divided into separate software, firmware and/or hardware components. Furthermore, it will also be apparent to those skilled in the art that such components, regardless of how they are combined or divided, can execute on the same computing device or multiple computing devices, and wherein the multiple computing devices can be connected by one or more networks.

Referring to FIG. 1B, a plurality of viewers 103 may gather in large numbers at a number of venues 102 to watch a media instance 101. In this embodiment, each venue 102 can host a set of viewers 103 belonging to the plurality of viewers 103. The set of viewers 103 hosted at any venue 102 can include a single viewer such that each of a plurality of viewers 103 may watch the same media instance 101 individually and separately at a venue 102 of his/her own choosing. Here, the venue can be the scene or locale of viewing of the media instance, for example, a home or any other place where the viewer can watch the media instance in private (e.g., watching online using a personal computer, etc.), and a public place such as a sport bar where the viewer may watch TV commercials during game breaks, as described above.

As described above, each of the viewers 103 may wear one or more sensors 104 to receive, measure and record physiological data from the viewer who is watching and/or interacting with the media instance. Each of the one or more sensors can be one of an electroencephalogram, an accelerometer, a blood oxygen sensor, a heart sensor, a galvanometer, and an electromygraph, to name a few. While these sensors are provided as examples, the sensors 104 can include any other physiological sensor.

Once the physiological data is measured, the one or more sensors attached to the viewer may transmit the physiological data via communication with a signal collection device 105. The signal collection device 105 is located at or near the same venue in which the viewer 103 is watching the media instance, but is not so limited. Here, the wireless communication covering the short range at the venue can be but is not limited to, Bluetooth, Wi-Fi, wireless LAN, radio frequency (RF) transmission, and any other form of short range wireless communication, for example. Upon receiving or accepting the physiological data from the one or more sensors 104 attached to the viewer, the signal collection device 105 is operable to pre-process, organize, and/or package the data into a form suitable for transmission, and then transmit the data over a network 106 to a centralized processing module 107 for further processing, storage, and analysis at a location separate and maybe remote from the distributed venues 102 where the data are collected. Here, the network can be but is not limited to, internet, intranet, wide area network (WAN), local area network (LAN), wireless network, and mobile communication network. The identity of the viewer is protected in an embodiment by stripping viewer identification information (e.g., name, address, etc.) from the data.

The processing module 107 accepts the physiological data from each of the plurality of viewers at distributed venues, derives one or more physiological responses based on the physiological data, aggregates and analyzes the derived responses to the media instance from the viewers, and stores the physiological data, the derived physiological responses and/or the analysis results of the aggregated responses in a reaction database 108. Optionally, a rating module 109 is operable to rate the media instance based on the physiological responses from the plurality of viewers.

Figure 2A:
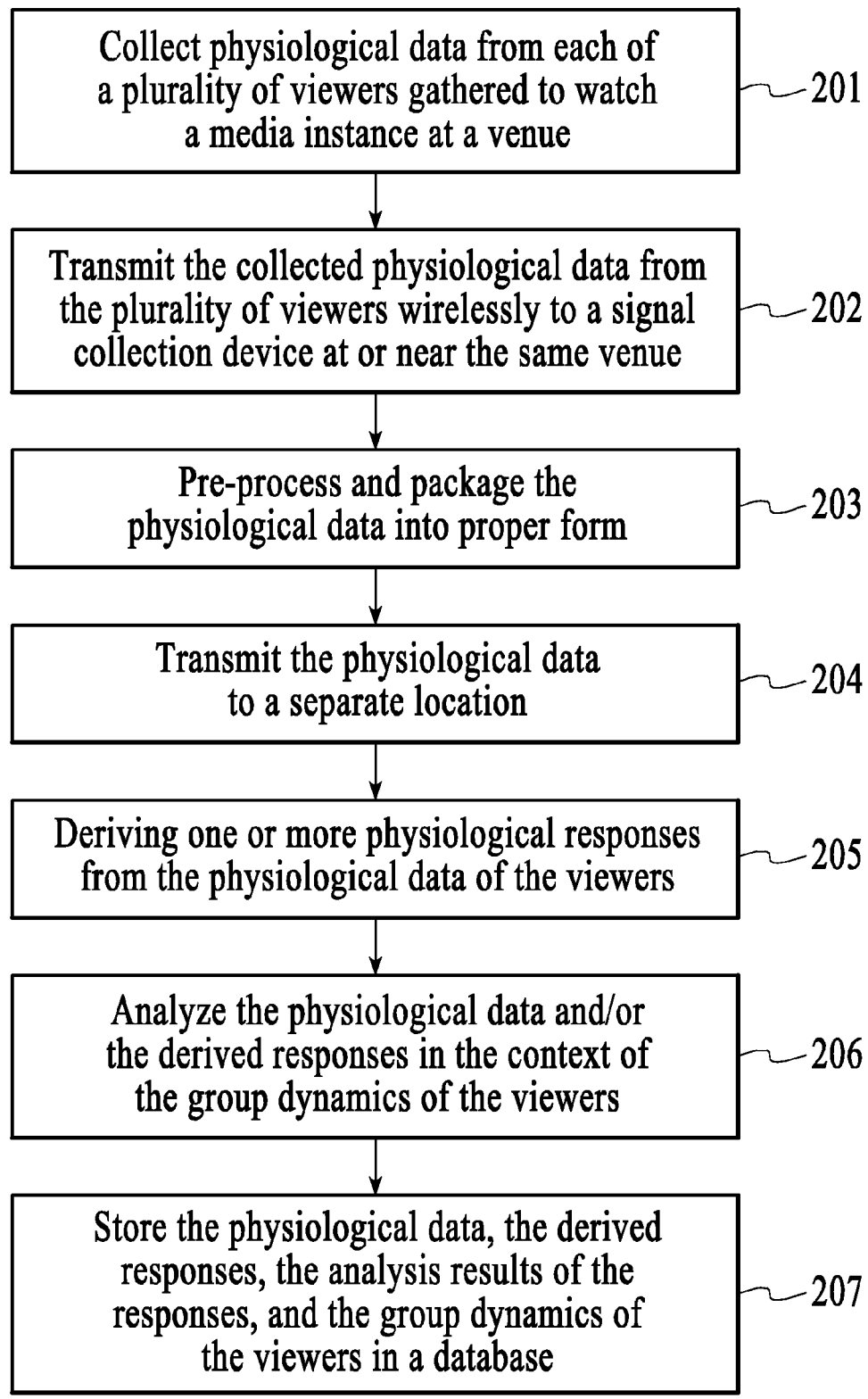
FIG. 2A is a flow chart of a process to support gathering physiological responses from viewers in a group setting, under an embodiment.

FIG. 2A is a flow chart of an exemplary process to support gathering physiological responses from viewers in a group setting, under an embodiment. Although this figure depicts functional steps in a particular order for purposes of illustration, the process is not limited to any particular order or arrangement of steps. One skilled in the art will appreciate that the various steps portrayed in this figure could be omitted, rearranged, combined and/or adapted in various ways.

Referring to FIG. 2A, physiological data from each of a plurality of viewers gathered to watch a media instance at a venue can be collected at 201. At 202, the collected physiological data from the plurality of viewers is transmitted wirelessly to a signal collection device at or near the same venue. The physiological data is then pre-processed, packaged in proper form at 203, and transmitted to a processing module at a separate location at 204. At 205, one or more physiological responses can be derived from the physiological data of the viewers, and the physiological data and/or the derived responses can be analyzed in the context of the group dynamics of the viewers at 206. Finally, the physiological data, the derived physiological responses, the analysis results of the responses, and the group dynamics of the viewers can be stored in a database at 207.

Figure 2B:
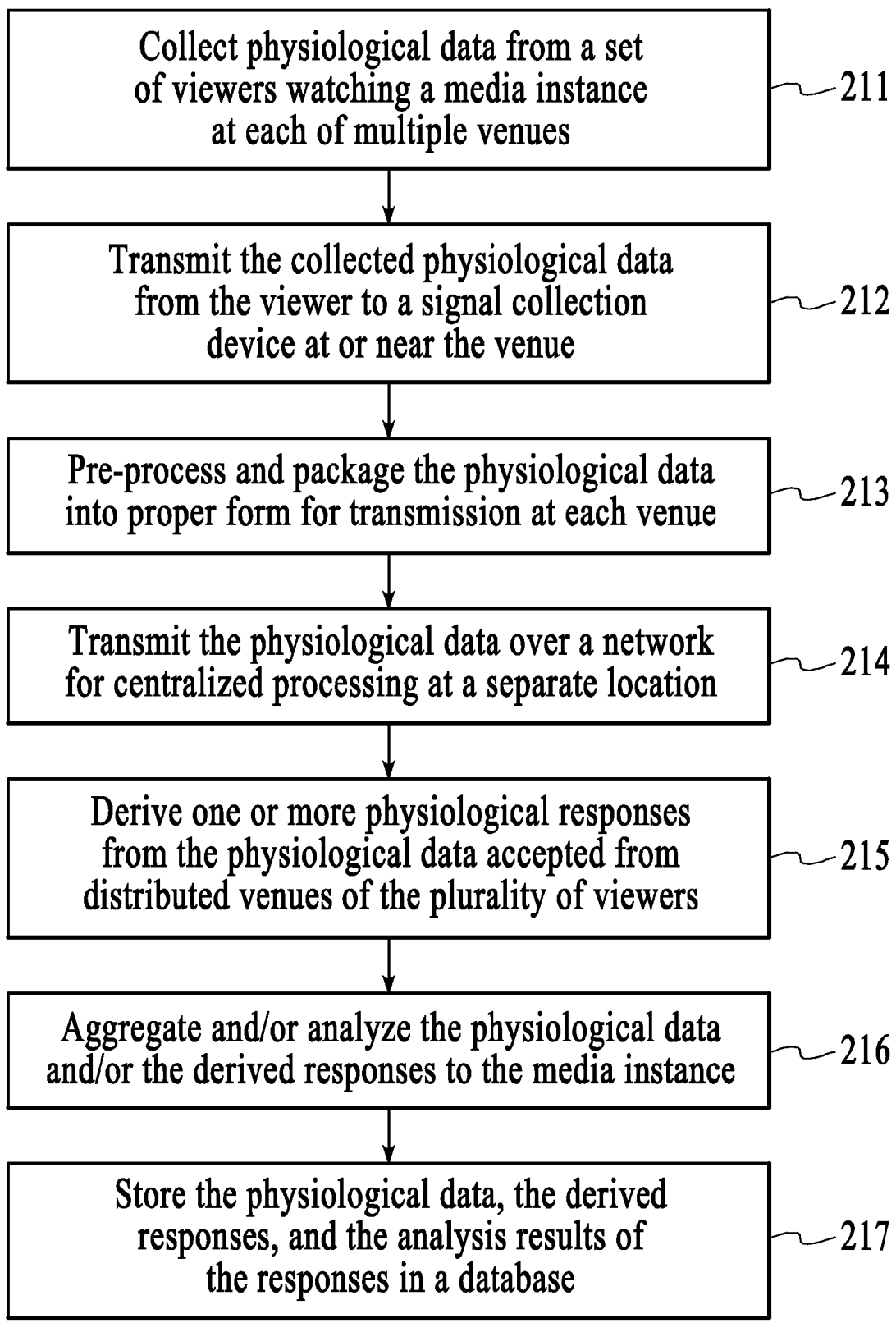
FIG. 2B is a flow chart illustrating an exemplary process to support large scale media testing, under an embodiment.

FIG. 2B is a flow chart of an exemplary process to support large scale media testing, under an embodiment. Although this figure depicts functional operations in a particular order for purposes of illustration, the process is not limited to any particular order or arrangement of operations. One skilled in the art will appreciate that the various operations portrayed in this figure could be omitted, rearranged, combined and/or adapted in various ways.

Referring to FIG. 2B, physiological data can be collected from a set of viewers watching a media instance at each of numerous venues at 211. At 212, the collected physiological data from the viewers at each venue is transmitted wirelessly to a signal collection device at or near the venue where the viewer is watching the media instance. The physiological data is then pre-processed, packaged in proper form for transmission at 213, and transmitted over a network for centralized processing at a separate location at 214. At 215, the physiological data from each of a plurality of viewers at distributed venues are accepted, and one or more physiological responses are derived from the physiological data. The physiological data and/or the derived responses to the media instance can then be aggregated and/or analyzed at 206. Finally, the physiological data, the derived physiological responses, and the analysis results of the responses can be stored in a database at 217.

The embodiments described herein enable self-administering testing such that a participant can test themselves in numerous ways with little or no outside human intervention or assistance. This self-administering testing is made possible through the use of the integrated sensor headset, described herein, along with a sensor headset tutorial and automatic data quality detection, in an embodiment.

The sensor headset, or headset, integrates sensors into a housing which can be placed on a portion of the human body (e.g., human head, hand, arm, leg, etc.) for measurement of physiological data, as described in detail herein. The device includes at least one sensor and a reference electrode connected to the housing. A processor coupled to the sensor and the reference electrode receives signals that represent electrical activity in tissue of a user. The device includes a wireless transmitter that transmits the output signal to a remote device. The device therefore processes the physiological data to create the output signal that correspond to a person's mental and emotional state (response).

Figure 3:
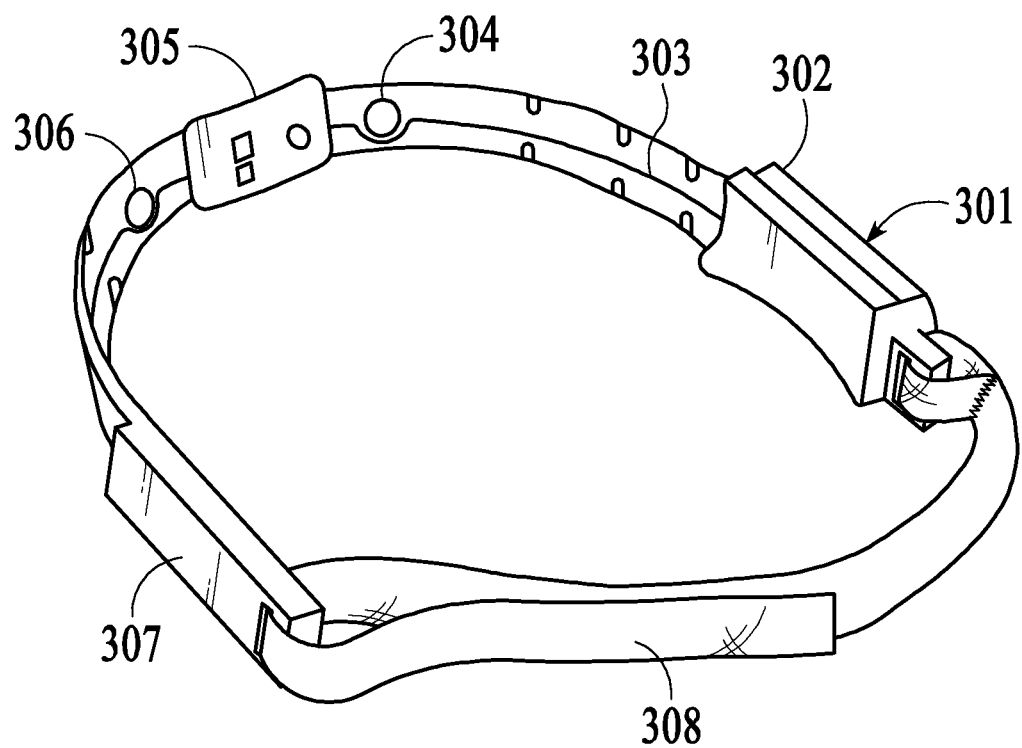
FIG. 3 shows an exemplary integrated headset that uses dry EEG electrodes and adopts wireless communication for data transmission, under an embodiment.

The integrated headset is shown in FIG. 3 and uses dry EEG electrodes and adopts wireless communication for data transmission. The integrated headset can be placed on the viewer's head for measurement of his/her physiological data while the viewer is watching the media instance. Referring to FIG. 3, the integrated headset may include at least one or more of the following components: a processing unit 301, a motion detection unit 302, a stabilizing component 303, a set of EEG electrodes, a heart rate sensor 305, power handling and transmission circuitry 307, and an adjustable strap 308. Note that although motion detection unit, EEG electrodes, and heart rate sensor are used here as non-limiting examples of sensors, other types of sensors can also be integrated into the headset, wherein these types of sensors can be but are not limited to, electroencephalograms, blood oxygen sensors, galvanometers, electromygraphs, skin temperature sensors, breathing sensors, and any other types of physiological sensors. The headset is described in detail below.

In some embodiments, the headset operates under the specifications for a suite of high level communication protocols, such as ZigBee. ZigBee uses small, low-power digital radios based on the IEEE 802.15.4 standard for wireless personal area network (WPAN). ZigBee is targeted at radio-frequency (RF) applications which require a low data rate, long battery life, and secure networking. ZigBee protocols are intended for use in embedded applications, such as the integrated headset, requiring low data rates and low power consumption.

In some embodiments, the integrated headsets on the viewers are operable to form a WPAN based on ZigBee, wherein such network is a general-purpose, inexpensive, self-organizing, mesh network that can be used for embedded sensing, data collection, etc. The resulting network among the integrated headsets uses relatively small amounts of power so each integrated headset might run for a year or two using the originally installed battery. Due to the limited wireless transmission range of each of the integrated headsets and the physical dimensions of the venue where a large number of viewers are gathering, not every integrated headset has the power to transmit data to the signal collection device directly due to the physical distance between them. Under the WPAN formed among the integrated headsets, an integrated headset far away from the signal collection device may first transmit the data to other integrated headsets nearby. The data will then be routed through the network to headsets that are physically close to the signal collection device, and finally transmitted to the signal collection device from those headsets.

In some embodiments, the signal collection device at the venue and the processing module at a separate location can communicate with each other over a network. Here, the network can be but is not limited to, internet, intranet, wide area network (WAN), local area network (LAN), wireless network, and mobile communication network. The signal collection device refers to any combination of software, firmware, hardware, or other component that is used to effectuate a purpose.

Data transmission from the headset can be handled wirelessly through a computer interface to which the headset links. No skin preparation or gels are needed on the tester to obtain an accurate measurement, and the headset can be removed from the tester easily and be instantly used by another person. No degradation of the headset occurs during use and the headset can be reused thousands of times, allowing measurement to be done on many participants in a short amount of time and at low cost.

To assist the user in fitting and wearing the headset, an embodiment automatically presents a tutorial to a participant. The tutorial describes how to a participant how to fit the headset to his/her head and how to wear the headset during the testing. The tutorial may also describe the presentation of feedback corresponding to the detected quality of data received from the participant, as described below. The tutorial can be automatically downloaded to a computer belonging to the participant, where the computer is to be used as a component of media instance viewing and/or for collection of physiological data during media instance viewing.

The tutorial of an embodiment, for example, is automatically downloaded to the participant's computer, and upon being received, automatically loads and configures or sets up the participant's computer for media instance viewing and/ or collection of physiological data during media instance viewing. The tutorial automatically steps through each of the things that a trained technician would do (if he/she were present) and checks the quality of the connections and placement while giving the user a very simple interface that makes them relax and be able to be in a natural environment. As an example, the tutorial instructs the participant to do one or more of the following during fitting of the headset and preparation for viewing of a media instance: check wireless signal strength from the headset, check contact of sensors, check participant's state to make sure their heart isn't racing too much and they are relaxed. If anything relating to the headset or the participant is discovered during the tutorial as not being appropriate for testing to begin, the tutorial instructs the participant in how to fix the deficiency.

Self-administering testing is further enabled through the user of automatic data quality detection. With reference to FIGS. 1A and 1B, the signal collection device 105 of an embodiment automatically detects data quality and provides to the participant, via a feedback display, one or more suggested remedies that correspond to any data anomaly detected in the participant's data. In providing feedback of data quality to a participant, the system automatically measures in realtime the quality of received data and provides feedback to the participant as to what actions to take if received data is less than optimal. The quality of the data is automatically determined using parameters of the data received from the sensors of the headset, and applying thresholds to these parameters.

As one example, the system can automatically detect a problem in a participant's data as indicated by the participant's blink rate exceeding a prespecified threshold. As another example, the system can automatically detect a problem in a participant's data as indicated by the participant's EEG, which is determined using the energy and size of the EEG, artifacts in the EEG. Further, the system can automatically detect problems in a participant's data using information of cardiac activity. In response to detected problems with a participant's data, the system automatically presents one or more remedies to the participant in response to the excessive blink rate. The suggested remedies presented can include any number and/or type of remedies that might reduce the blink rate to a nominal value. The participant is expected to follow the remedies and, in so doing, should eliminate the reception of any data that is less than optimal.

In addition to the automatic detection of problems with data received from a participant, the data can be use to determine if a potential participant is able or in appropriate condition to be tested. So, for example, if a participant's heart is racing or his/her eyes are blinking crazily and jittery, as indicated in the received data, the participant is not in a state to be tested and can be removed as a potential participant.

Figure 4:
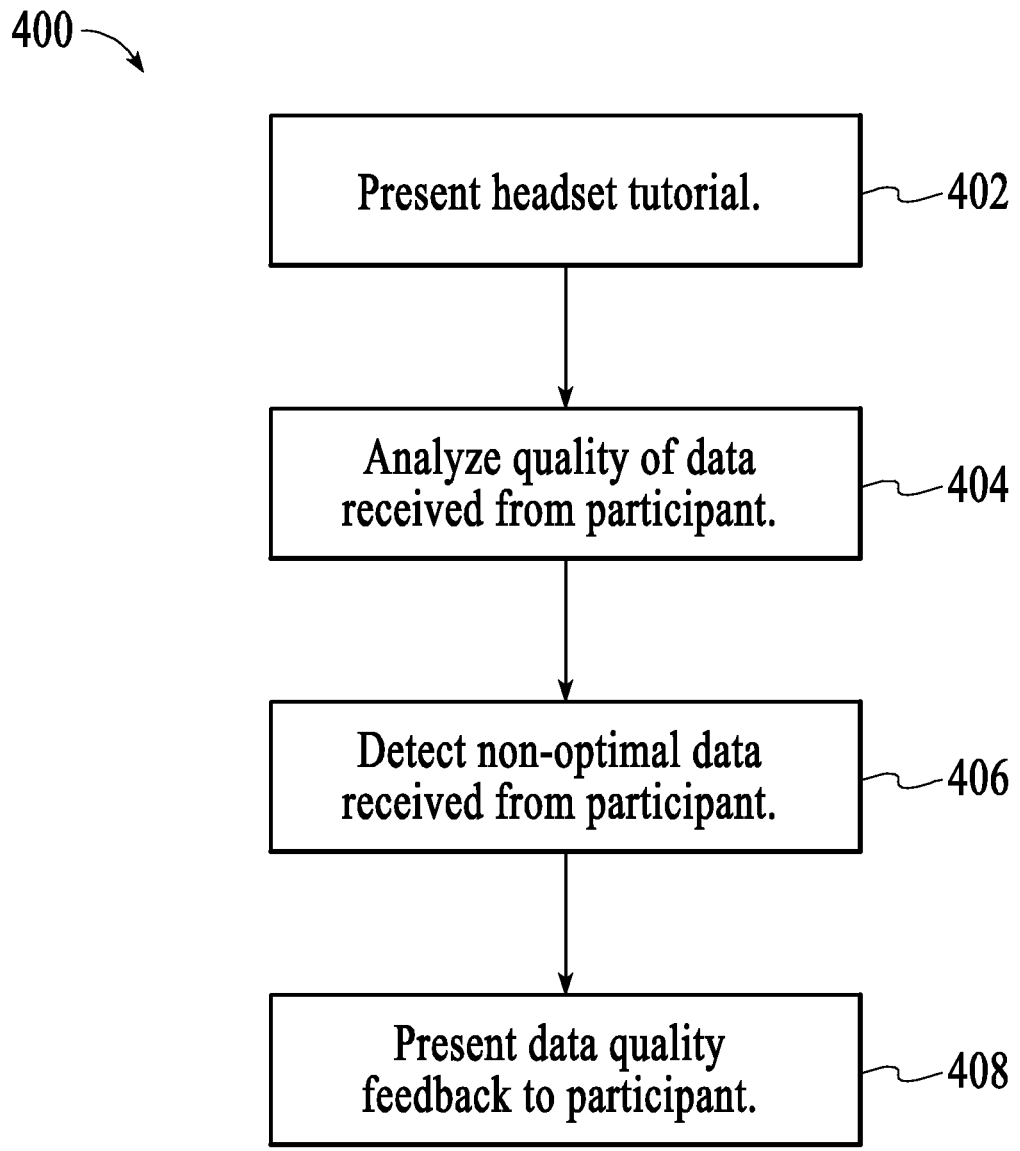
FIG. 4 is a flow diagram of self-administering testing, under an embodiment.

FIG. 4 is a flow diagram of self-administering testing 402, under an embodiment. The participant or user activates the system and, in response, is presented 402 with a headset tutorial that describes how to fit and wear the headset during testing. As the participant is viewing the media instance, data received from the participant is analyzed 404 for optimal quality. The reception of non-optimal data is detected 406 and, in response, data quality feedback is presented 408 to the participant. The data quality feedback includes one or more suggested remedies that correspond to the detected anomaly in the participant's data, as described above.

In some embodiments, the signal collection device can be a stand-alone data collection and transmitting device, such as a set-top box for a non-limiting example, with communication or network interfaces to communicate with both the sensors and the centralized processing module. Alternatively, the signal collection device can be embedded in or integrated with another piece of hardware, such as a TV, a monitor, or a DVD player that presents the media instance to the viewer for a non-limiting example. Here, the signal collection device refers to any combination of software, firmware, hardware, or other component that is used to effectuate a purpose.

In some embodiments, the signal collection device is operable to transmit only "meaningful" data to the centralized processing module in order to alleviate the burden on the network and/or the processing module by pre-processing the data collected from each viewer before transmission. In real application, it is inevitable that certain viewer(s) may not be paying attention to the media instance for its entire duration. For the purpose of evaluating the media instance, the data collected from a viewer during the time he/she was not looking or focusing on the screen/monitor displaying the media instance is irrelevant and should be removed. In an alternative embodiment, pre-processing can be performed by the processing module 107. In another alternative embodiment, pre-processing can be shared between the signal collection device 105 and the processing module 107.

Pre-processing of the data collected includes, but is not limited to, filtering out "noise" in the physiological data collected from each viewer. The "noise" includes data for any statistically non-pertinent period of time when he/she was not paying attention to the media instance, so that only statistically pertinent moments and/or moments related to events in the media instance are transmitted. The processing module may convert the physiological data from time domain to frequency domain via Fourier Transform or any other type of transform commonly used for digital signal processing known to one skilled in the art. Once transformed into frequency domain, part of the section in the data that corresponds to a viewer's talking, head orientation, nodding off, sleeping, or any other types of motion causing the viewer not to pay attention to the media instance can be identified via pattern recognition and other matching methods based on known models on human behaviors.

The system removes data that is less than optimal from the cumulative data set. Data removal includes removing all data of a user if the period for which the data is non-optimal exceeds a threshold, and also includes removing only non-optimal portions of data from the total data received from a participant. In removing non-optimal data, the system automatically removes artifacts for the various types of data collected (e.g., artifact removal for EEG data based on participant blinking, eye movement, physical movement, muscle noise, etc.). The artifacts used in assessing data quality in an embodiment are based on models known in the art.

In an embodiment, the signal collection device 105 automatically performs data quality analysis on incoming data from a sensor headset. The signal collection device 105 analyzes the incoming signal for artifacts in the sensor data (e.g., EEG sensors, heart sensors, etc.). The signal collection device 105 also uses the accelerometer data to measure movement of the participant, and determine any periods of time during which the participant has movement that exceeds a threshold. The data collected for a participant during a time period in which the participant was found to have "high" movement exceeding the threshold is segmented out or removed as being non-optimal data not suited for inclusion in the data set.

In an alternative embodiment, the processing module 107 automatically performs data quality analysis on incoming data from a sensor headset. The processing module 107 analyzes the incoming signal for artifacts in the sensor data (e.g., EEG sensors, heart sensors, etc.). The processing module 107 also uses the accelerometer data to measure movement of the participant, and determine any periods of time during which the participant has movement that exceeds a threshold. The data collected for a participant during a time period in which the participant was found to have "high" movement exceeding the threshold is segmented out or removed as being non-optimal data not suited for inclusion in the data set.

Pre-processing of the data collected includes, but is not limited to, synchronizing the data. The system of an embodiment synchronizes the data from each user to that of every other user to form the cumulative data. Additionally, the system synchronizes the cumulative data to the media instance with which it corresponds. The signal collection device 105 of the system synchronizes the time codes of all data being recorded, which then allows the cumulative data to be synchronized to the media instance (e.g., video) on playback. In so doing, the system synchronizes the time code of each portion or instance of data to every other portion or instance of data so it is all comparable. The system then synchronizes the cumulative data stream to the media instance.

In performing synchronization, the stimuli (e.g., media instance) are recorded to generate a full record of the stimuli. A tagging system aligns the key points in the stimuli and associates these key points in the stimuli with the corresponding points in time, or instances, in the recorded data. Using this technique, offsets are determined and applied as appropriate to data received from each participant.

In an alternative embodiment, participants can be prompted to take, as a synchronizing event, some action (e.g., blink ten times) that can be detected prior to or at the beginning of the media instance. The data corresponding to each participant is then synchronized or aligned using the evidence of the synchronizing event in the data.

Pre-processing of the data collected additionally includes, but is not limited to, compressing the physiological data collected from each viewer. Sometimes, a viewer's reaction to events in a media instance may go "flat" for a certain period of time without much variation. Under such a scenario, the processing module may skip the non-variant portion of the physiological data and transmit only the portion of the physiological data showing variations in the viewer's emotional reactions to the centralized processing module.

Pre-processing of the data collected further includes, but is not limited to, summarizing the physiological data collected from each viewer. When physiological data are collected from a large group of viewers, the bandwidth of the network and/or the processing power of the processing module in real time can become a problem. To this end, the processing module may summarize the viewer's reactions to the media instance in conclusive terms and transmit only such conclusions instead of the physiological data over the entire duration of the media instance.

In some embodiments, the processing module is operable to run on a computing device, a communication device, or any electronic devices that are capable of running a software component. For non-limiting examples, a computing device can be but is not limited to, a laptop PC, a desktop PC, and a server machine.

In some embodiments, the processing module is operable to interpolate the "good" data of time period(s) when the viewer is paying attention to "cover" the identified "noise" or non-variant data that has been filtered out during pre-processing. The interpolation can be done via incremental adjustment of data during the "good" period adjacent in time to the "noise" period. The physiological data from each viewer can be "smoothed" out over the entire duration of the media instance before being aggregated to derive the physiological responses of the viewers to evaluate the media instance.

In some embodiments, the reaction database stores pertinent data of the media instance the viewers were watching, in addition to their physiological data and/or derived physiological responses to the media instance. The pertinent data of each media instance that is being stored includes, but is not limited to, one or more of the actual media instance for testing (if applicable), events/moments break down of the media instance, and metadata of the media instance, which can include but is not limited to, production company, brand, product name, category (for non-limiting examples, alcoholic beverages, automobiles, etc), year produced, target demographic (for non-limiting examples, age, gender, income, etc) of the media instances.

In some embodiments, in addition to storing analysis results of the physiological responses to the media instance from the viewers, the reaction database may also include results of surveys asked for each of the plurality of viewers before, during and or after their viewing of the media instance.

In some embodiments, the rating module is operable to calculate a score for the media instance based on the physiological responses from the viewers. The score of the media instance is high if majority of the viewers respond positively to the media instance. On the other hand, the score of the media instance is low if majority of the viewers respond negatively to the media instance.

While physiological data is collected from participants using the system to support large scale media testing, described above, an embodiment enables remote and interactive access, navigation, and analysis of reactions from one or more viewers to a specific media instance. Here, the reactions include, but are not limited to, physiological responses, survey results, verbatim feedback, event-based metadata, and derived statistics for indicators of success and failure from the viewers. Upon collection of the physiological data from participating viewers, the reactions from the viewers are aggregated and stored in a database and are delivered to a user via a web-based graphical interface or application, such as a web browser.

Through the web-based graphical interface, or other network coupling, the user is able to remotely access and navigate the specific media instance, together with one or more of: the aggregated physiological responses that have been synchronized with the media instance, the survey results, and the verbatim feedbacks related to the specific media instance. Instead of being presented with static data (such as a snapshot) of the viewers' reactions to the media instance, the user is now able to interactively divide, dissect, parse, and analysis the reactions in any way he/she prefer. The embodiments described herein provide automation that enables those who are not experts in the field of physiological analysis to understand and use physiological data by enabling these non-experts to organize the data and organize and improve presentation or visualization of the data according to their specific needs. In this manner, the embodiments herein provide an automated process that enables non-experts to understand complex data, and to organize the complex data in such a way as to present conclusions as appropriate to the media instance.

Having multiple reactions from the viewers (e.g., physiological responses, survey results, verbatim feedback, events tagged with metadata, etc.) available in one place and at a user's fingertips, along with the automated methods for aggregating the data provided herein, allows the user to view the reactions to hundreds of media instances in one sitting by navigating through them. For each of the media instances, the integration of multiple reactions provides the user with more information than the sum of each of the reactions to the media instance. For a non-limiting example, if one survey says that an ad is bad, that is just information; but if independent surveys, verbatim feedbacks and physiological data across multiple viewers say the same, the reactions to the media instance become more trustworthy. By combining this before a user sees it, the correct result is presented to the user.

A number of processing and pre-processing applications are described above, but the components of embodiments described herein are not limited to the applications described above. For example, any application described above as processing, can be executed as pre-processing. Further, any application described above as pre-processing, can be executed as processing. Moreover, any application requiring processing can be shared between processing and pre-processing components or activities. Additionally, the signal processing and other processing described in the Related Applications can be executed as part of the processing and/or pre-processing described herein.

Upon collection of the physiological data, as described above, an embodiment enables remote and interactive access, navigation, and analysis of reactions from one or more viewers to a specific media instance. Here, the reactions include, but are not limited to, physiological responses, survey results, verbatim feedback, event-based metadata, and derived statistics for indicators of success and failure from the viewers. The reactions from the viewers are aggregated and stored in a database and are delivered to a user via a web-based graphical interface or application, such as a Web browser. Through the web-based graphical interface, the user is able to remotely access and navigate the specific media instance, together with one or more of: the aggregated physiological responses that have been synchronized with the media instance, the survey results, and the verbatim feedbacks related to the specific media instance. Instead of being presented with static data (such as a snapshot) of the viewers' reactions to the media instance, the user is now able to interactively divide, dissect, parse, and analysis the reactions in any way he/she prefer. The embodiments herein provides automation that enables those who are not experts in the field of physiological analysis to understand and use physiological data by enabling these non-experts to organize the data and organize and improve presentation or visualization of the data according to their specific needs. In this manner, the embodiments herein provide an automated process that enables non-experts to understand complex data, and to organize the complex data in such a way as to present conclusions as appropriate to the media instance.

Having multiple reactions from the viewers (e.g., physiological responses, survey results, verbatim feedback, events tagged with metadata, etc.) available in one place and at a user's fingertips, along with the automated methods for aggregating the data provided herein, allows the user to view the reactions to hundreds of media instances in one sitting by navigating through them. For each of the media instances, the integration of multiple reactions provides the user with more information than the sum of each of the reactions to the media instance. For a non-limiting example, if one survey says that an ad is bad, that is just information; but if independent surveys, verbatim feedbacks and physiological data across multiple viewers say the same, the reactions to the media instance become more trustworthy. By combining this before a user sees it, the correct result is presented to the user.

Figure 5:
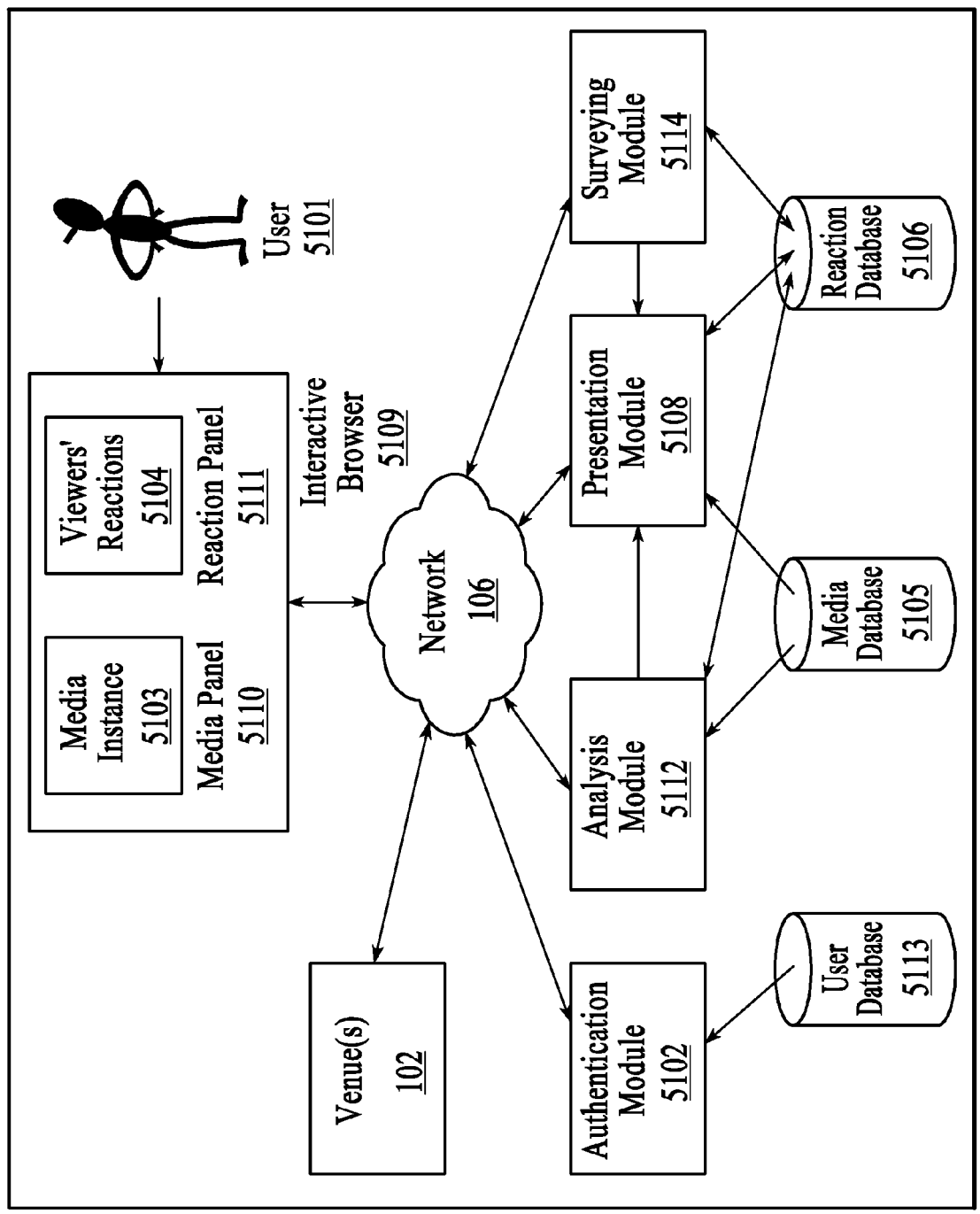
FIG. 5 is a system to support remote access and analysis of media and reactions from viewers, under an embodiment.

FIG. 5 is an illustration of an exemplary system to support automated remote access and analysis of media and reactions from viewers, under an embodiment. Although this diagram depicts components as functionally separate, such depiction is merely for illustrative purposes. It will be apparent to those skilled in the art that the components portrayed in this figure can be arbitrarily combined or divided into separate software, firmware and/or hardware components. Furthermore, it will also be apparent to those skilled in the art that such components, regardless of how they are combined or divided, can execute on the same computing device or multiple computing devices, and wherein the multiple computing devices can be connected by one or more networks.

Referring to FIG. 5, an authentication module 5102 is operable to authenticate identity of a user 5101 requesting access to a media instance 5103 together with one or more reactions 5104 from a plurality of viewers of the media instance remotely over a network 106. Here, the media instance and its pertinent data can be stored in a media database 5105, and the one or more reactions from the viewers can be stored in a reaction database 5106, respectively. The network 106 can be, but is not limited to, one or more of the internet, intranet, wide area network (WAN), local area network (LAN), wireless network, Bluetooth, and mobile communication networks. Once the user is authenticated, a presentation module 5108 is operable to retrieve and present the requested information (e.g., the media instance together with one or more reactions from the plurality of viewers) to the user via an interactive browser 5109. The interactive browser 5109 comprises at least two panels including a media panel 5110, which is operable to present, play, and pause the media instance, and a response panel 5111, which is operable to display the one or more reactions corresponding to the media instance, and provide the user with a plurality of features to interactively divide, dissect, parse, and analysis the reactions.

Figure 6:
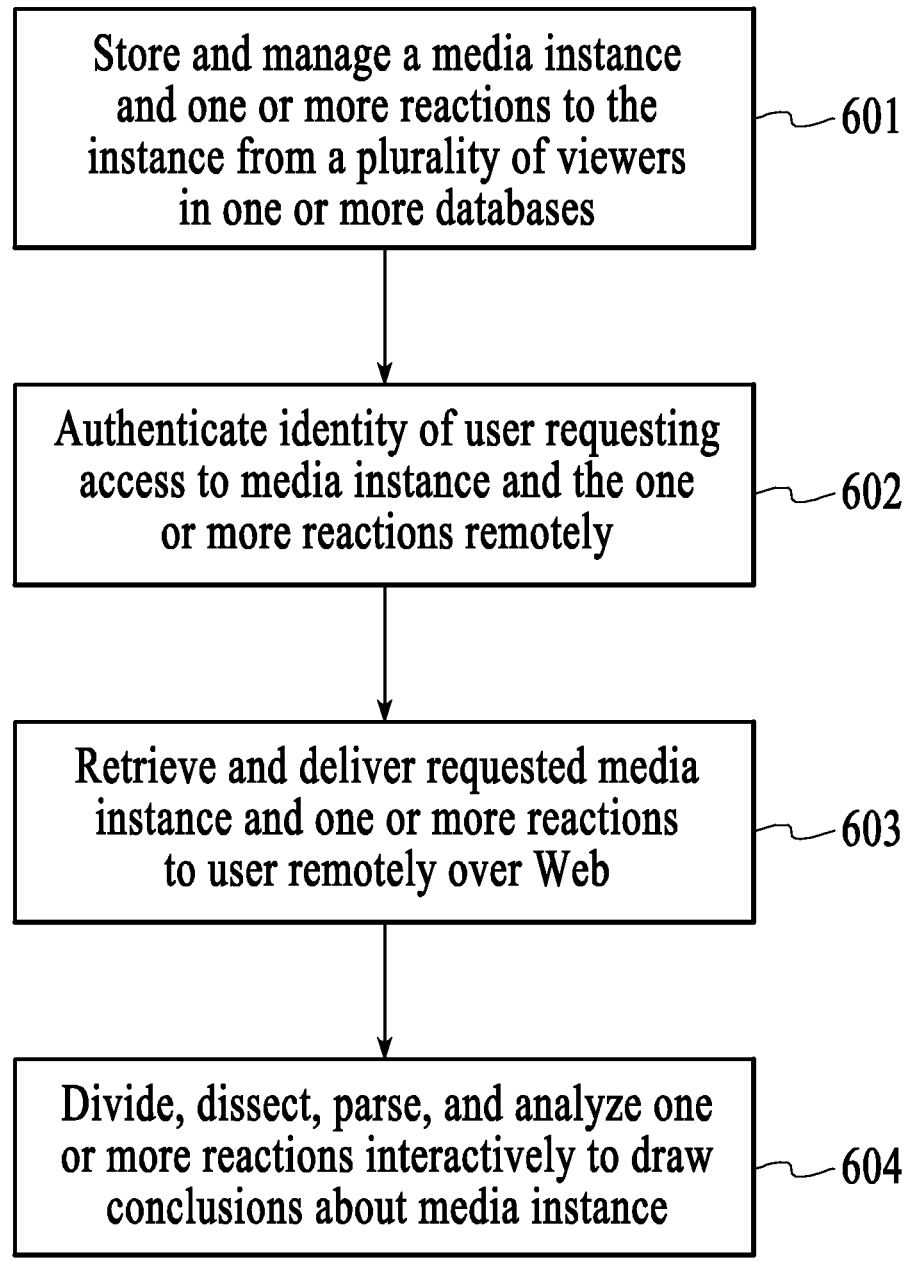
FIG. 6 is a flow chart for remote access and analysis of media and reactions from viewers, under an embodiment.

FIG. 6 is a flow chart illustrating an exemplary process to support remote access and analysis of media and reactions from viewers. Although this figure depicts functional operations in a particular order for purposes of illustration, the process is not limited to any particular order or arrangement of operations. One skilled in the art will appreciate that the various operations portrayed in this figure could be omitted, rearranged, combined and/or adapted in various ways.

Referring to FIG. 6, a media instance and one or more reactions to the instance from a plurality of viewers are stored and managed in one or more databases at 601. Data or information of the reactions to the media instance is obtained or gathered from each user via a sensor headset, as described herein and in the Related Applications. At 602, the identity of a user requesting access to the media instance and the one or more reactions remotely is authenticated. At 603, the requested media instance and the one or more reactions are retrieved and delivered to the user remotely over a network (e.g., the Web). At 604, the user may interactively aggregate, divide, dissect, parse, and analyze the one or more reactions to draw conclusions about the media instance.

In some embodiments, alternative forms of access to the one or more reactions from the viewers other than over the network may be adopted. For non-limiting examples, the reactions can be made available to the user on a local server on a computer or on a recordable media such as a DVD disc with all the information on the media.

In some embodiments, with reference to FIG. 5, an optional analysis module 5112 is operable to perform in-depth analysis on the viewers' reactions to a media instance as well as the media instance itself (e.g., dissecting the media instance into multiple scenes/events/sections). Such analysis provides the user with information on how the media instance created by the user is perceived by the viewers. In addition, the analysis module is also operable to categorize viewers' reactions into the plurality of categories.

In some embodiments, user database 5113 stores information of users who are allowed to access the media instances and the reactions from the viewers, and the specific media instances and the reactions each user is allowed to access. The access module 5106 may add or remove a user for access, and limit or expand the list of media instances and/or reactions the user can access and/or the analysis features the user can use by checking the user's login name and password. Such authorization/limitation on a user's access can be determined to based upon who the user is, e.g., different amounts of information for different types of users. For a non-limiting example, Company ABC can have access to certain ads and survey results of viewers' reactions to the ads, which Company XYZ can not or have only limited access to.

Figure 7:
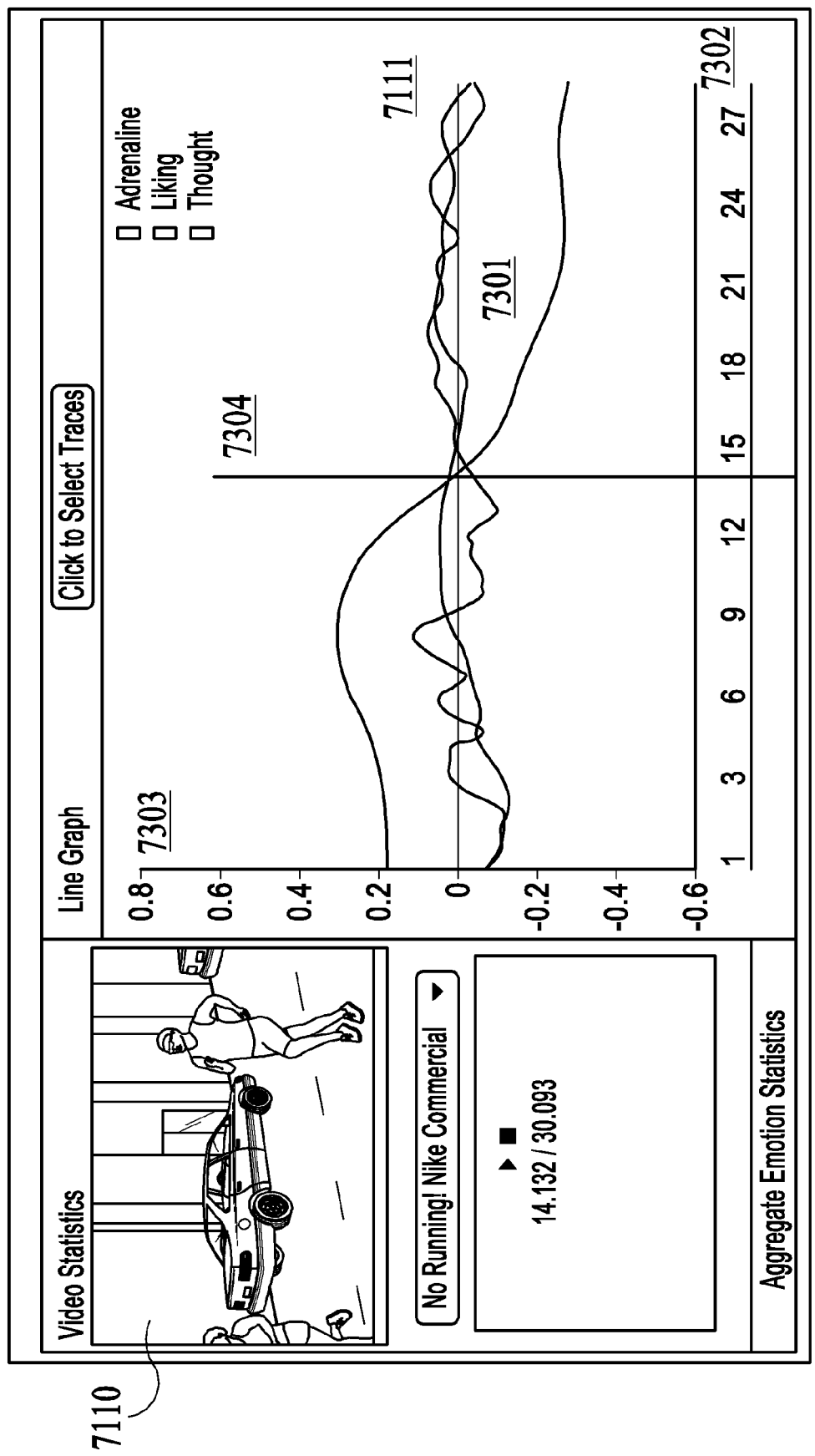
FIG. 7 shows one or more exemplary physiological responses aggregated from the viewers and presented in the response panel of the interactive browser, under an embodiment.

In some embodiments, one or more physiological responses aggregated from the viewers can be presented in the response panel 7111 as lines or traces 7301 in a two-dimensional graph or plot as shown in FIG. 7. Horizontal axis 7302 of the graph represents time, and vertical axis 7303 of the graph represents the amplitude (intensity) of the one or more physiological responses. Here, the one or more physiological responses are aggregated over the viewers via one or more of: max, min, average, deviation, or a higher ordered approximation of the intensity of the physiological responses from the viewers. The responses are synchronized with the media instance at each and every moment over the entire duration of the media instance, allowing the user to identify the second-by second changes in viewers' emotions and their causes. A cutting line 7304 marks the physiological responses from the viewers corresponding to the current scene (event, section, or moment in time) of the media instance. The cutting line moves in coordination with the media instance being played.

In some embodiments, change (trend) in amplitude of the aggregated responses is also a good measure of the quality of the media instance. If the media instance is able to change viewers emotions up and down in a strong manner (for a non-limiting example, mathematical deviation of the response is large), such strong change in amplitude corresponds to a good media instance that puts the viewers into different emotional states. In contrast, a poor performing media instance does not put the viewers into different emotional states. The amplitudes and the trend of the amplitudes of the responses are good measures of the quality of the media instance. Such information can be used by media designers to identify if the media instance is eliciting the desired response and which key events/scenes/sections of the media instance need to be changed in order to match the desired response. A good media instance should contain multiple moments/scenes/events that are intense and produce positive amplitude of response across viewers. A media instance that failed to create such responses may not achieve what the creators of the media instance have intended.

In some embodiments, other than providing a second by second view for the user to see how specific events in the media instance affect the viewers' emotions, the aggregated responses collected and calculated can also be used for the compilation of aggregate statistics, which are useful in ranking the overall affect of the media instance. Such statistics include but are not limited to Average Liking and Heart Rate Deviation.

Figure 8:
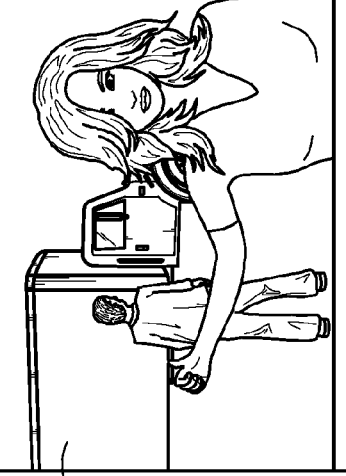
FIG. 8 shows exemplary verbatim comments and feedbacks collected from the viewers and presented in the response panel of the interactive browser, under an embodiment.

In some embodiments, the viewers of the media instance are free to write comments (e.g., what they like, what they dislike, etc.) on the media instance, and the verbatim (free flowing text) comments or feedbacks 501 from the viewers can be recorded and presented in a response panel 7111 as shown in FIG. 8. Such comments can be prompted, collected, and recorded from the viewers while they are watching the specific media instance and the most informative ones are put together and presented to the user. The user may then analyze, and digest keywords in the comments to obtain a more complete picture of the viewers' reactions. In addition, the user can search for specific keywords he/she is interested in about the media instance, and view only those comments containing the specified keywords.

In some embodiments, the viewers' comments about the media instance can be characterized as positive or negative in a plurality of categories/topics/aspects related to the product, wherein such categories include but are not limited to, product, event, logo, song, spokesperson, jokes, narrative, key events, storyline. These categories may not be predetermined, but instead be extracted from the analysis of their comments.

Figure 9:
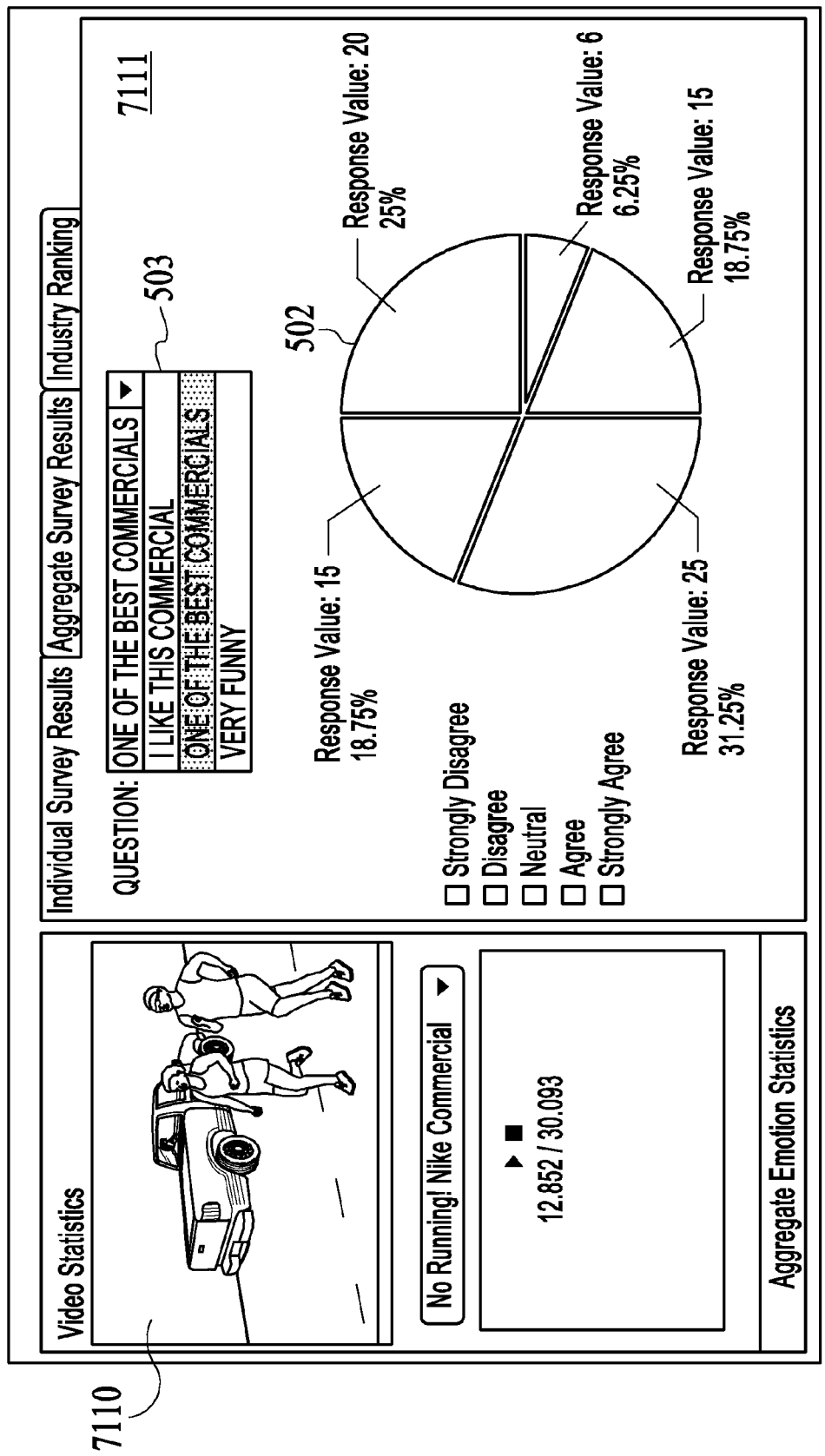
FIG. 9 shows exemplary answers to one or more survey questions collected from the viewers and presented as a pie chart in the response panel of the interactive browser, under an embodiment.

In some embodiments, answers to one or more survey questions 503 aggregated from the viewers can be rendered graphically, for example, by being presented in the response panel 7111 in a graphical format 502 as shown in FIG. 9. Alternatively, a graphical format can be used to display the response distribution of viewers asked to rate an advertisement. The graphical format can be but is not limited to, a bar graph, a pie chart, a histogram, or any other suitable graph type.

In some embodiments, the survey questions can be posed or presented to the viewers while they are watching the specific media instance and their answers to the questions are collected, recorded, summed up by pre-defined categories via a surveying module 5114 (FIG. 5). Once the survey results are made available to the user (creator of the media instance), the user may pick any of the questions, and be automatically presented with survey results corresponding to the question visually to the user. The user may then view and analyze how viewers respond to specific questions to obtain a more complete picture of the viewers' reactions.

In some embodiments, many different facets of the one or more reactions from the viewers described above can be blended into a few simple metrics that the user can use to see how it is currently positioned against the rest of their industry. For the user, knowing where it ranks in its industry in comparison to its competition is often the first step in getting to where it wants to be. For a non-limiting example, in addition to the individual survey results of a specific media instance, the surveying module may also provide the user with a comparison of survey results and statistics to multiple media instances. This automation allows the user not only to see the feedback that the viewers provided with respect to the specific media instance, but also to evaluate how the specific media instance compares to other media instances designed by the same user or its competitors. As an example, a graph displaying the percentages of viewers who "liked" or "really liked" a set of advertisements can help to determine if a new ad is in the top quartile with respect to other ads.

An embodiment provides a user not only with tools for accessing and obtaining a maximum amount of information out of reactions from a plurality of viewers to a specific media instance, but also with actionable insights on what changes the user can make to improve the media instance based on in-depth analysis of the viewers' reactions. Such analysis requires expert knowledge on the viewers' physiological behavior and large amounts of analysis time, which the user may not possess. Here, the reactions include but are not limited to, physiological responses, survey results, and verbatim feedbacks from the viewers, to name a few. The reactions from the viewers are aggregated and stored in a database and presented to the user via a graphical interface, as described above. The embodiment includes predefined methods for extracting information from the reactions and presenting that information so that the user is not required to be an expert in physiological data analysis to reach and understand conclusions supported by the information. Making in-depth analysis of reactions to media instances and actionable insights available to a user enables a user who is not an expert in analyzing physiological data to obtain critical information that can have significant commercial and socially positive impacts.

Figure 10:
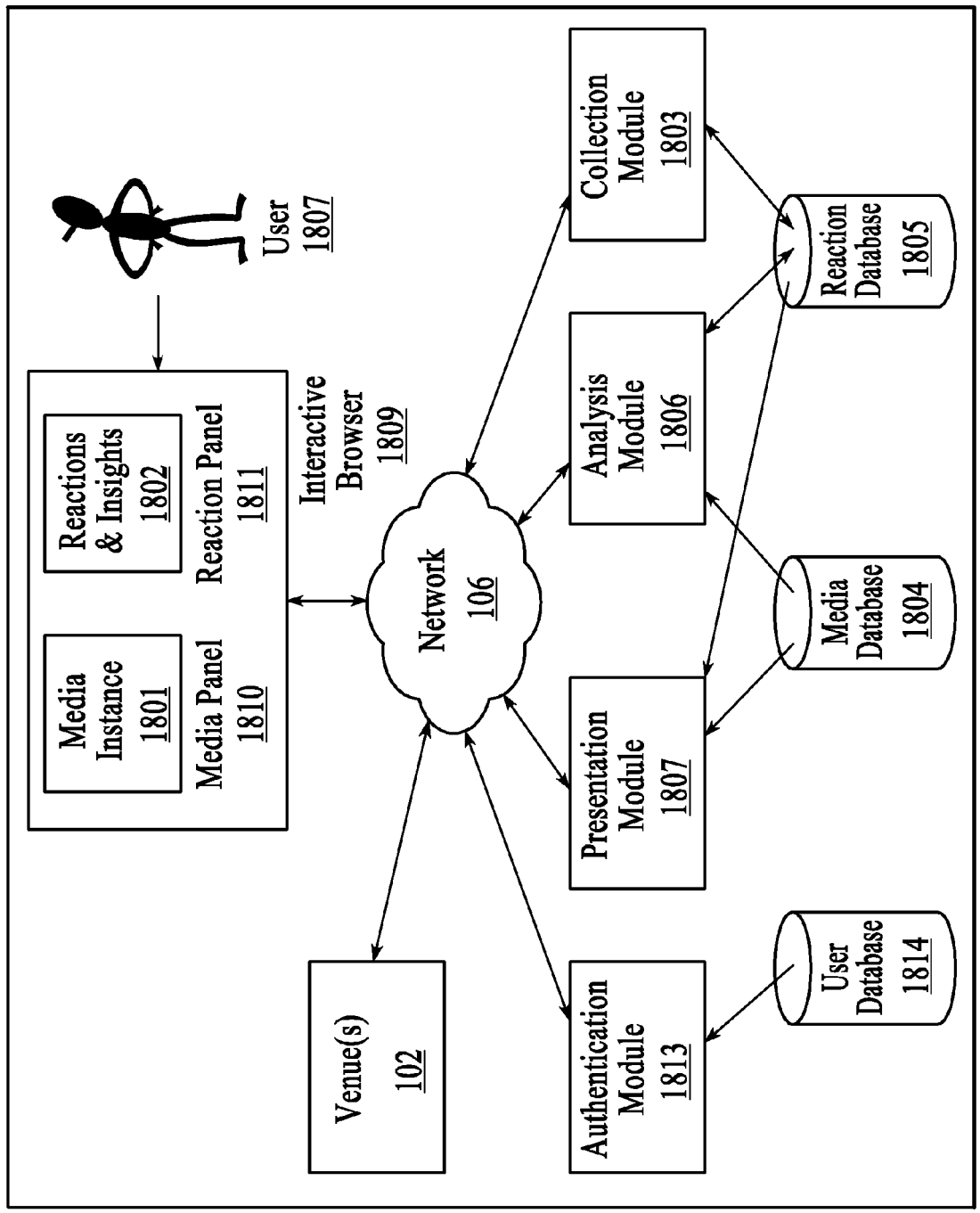
FIG. 10 is a system to support providing actionable insights based on in-depth analysis of reactions from viewers, under an embodiment.

FIG. 10 is an illustration of an exemplary system to support providing actionable insights based on in-depth analysis of reactions from viewers. Although this diagram depicts components as functionally separate, such depiction is merely for illustrative purposes. It will be apparent to those skilled in the art that the components portrayed in this figure can be arbitrarily combined or divided into separate software, firmware and/or hardware components. Furthermore, it will also be apparent to those skilled in the art that such components, regardless of how they are combined or divided, can execute on the same computing device or multiple computing devices, and wherein the multiple computing devices can be connected by one or more networks.

Referring to FIG. 10, a collection module 1803 is operable to collect, record, store and manage one or more reactions 1802 from a plurality of viewers of a media instance 1801. The viewers from whom reactions 1802 are collected can be in the same physical location or different physical locations. Additionally, the viewers can be viewing the media instance and the reactions collected at the same time, or at different times (e.g., viewer 1 is viewing the media instance at 9 AM while viewer 2 is viewing the media instance at 3 PM). Data or information of the reactions to the media instance is obtained or gathered from each user via a sensor headset. The sensor headset of an embodiment integrates sensors into a housing which can be placed on a human head for measurement of physiological data. The device includes at least one sensor and can include a reference electrode connected to the housing. A processor coupled to the sensor and the reference electrode receives signals that represent electrical activity in tissue of a user. The processor generates an output signal including data of a difference between an energy level in each of a first and second frequency band of the signals. The difference between energy levels is proportional to release level present time emotional state of the user. The headset includes a wireless transmitter that transmits the output signal to a remote device. The headset therefore processes the physiological data to create the output signal that correspond to a person's mental and emotional state (reactions or reaction data). An example of a sensor headset is described in U.S. patent application Ser. No. 12/206,676, filed Sep. 8, 2008, Ser. No. 11/804,517, filed May 17, 2007, and Ser. No. 11/681,265, filed Mar. 2, 2007.

The media instance and its pertinent data can be stored in a media database 1804, and the one or more reactions from the viewers can be stored in a reaction database 1805, respectively. An analysis module 1806 performs in-depth analysis on the viewers' reactions and provides actionable insights on the viewers' reactions to a user 1807 so that the user can draw its own conclusion on how the media instance can/should be improved. A presentation module 1808 is operable to retrieve and present the media instance 1801 together with the one or more reactions 1802 from the viewers of the media instance via an interactive browser 1809. Here, the interactive browser includes at least two panels: a media panel 1810, operable to present, play, and pause the media instance; and a reaction panel 1811, operable to display the one or more reactions corresponding to the media instance as well as the key insights provided by the analysis module 1806.

Figure 11:
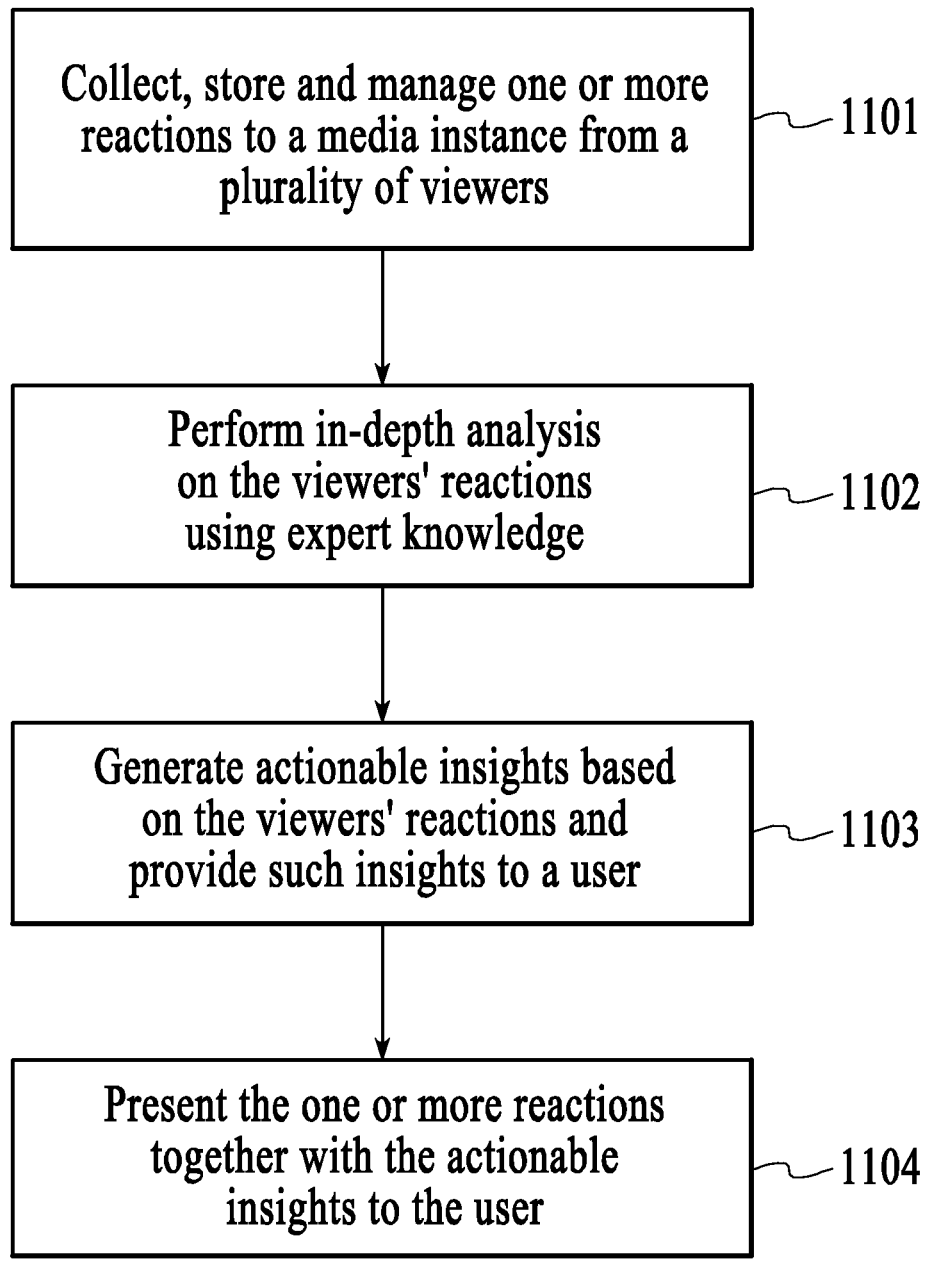
FIG. 11 is a flow chart for providing actionable insights based on in-depth analysis of reactions from viewers, under an embodiment.

FIG. 11 is a flow chart illustrating an exemplary automatic process to support providing actionable insights based on in-depth analysis of reactions from viewers. Although this figure depicts functional operations in a particular order for purposes of illustration, the process is not limited to any particular order or arrangement of operations. One skilled in the art will appreciate that the various operations portrayed in this figure could be omitted, rearranged, combined and/or adapted in various ways.

Referring to FIG. 11, one or more reactions to a media instance from a plurality of viewers are collected, stored and managed in one or more databases at 1101. At 1102, in-depth analysis is performed on the viewers' reactions using expert knowledge, and actionable insights are generated based on the viewers' reactions and provided to a user at 1103 so that the user can draw its own conclusion on the media instance can/should be improved. At 1104, the one or more reactions can be presented to the user together with the actionable insights to enable the user to draw its own conclusions about the media instance. The configuration used to present the reactions and actionable insights can be saved and tagged with corresponding information, allowing it to be recalled and used for similar analysis in the future.

In some embodiments, the analysis module is operable to provide insights or present data based in-depth analysis on the viewers' reactions to the media instance on at least one question. An example question is whether the media instance performs most effectively across all demographic groups or especially on a specific demographic group, e.g., older women? Another example question is whether certain elements of the media instance, such as loud noises, were very effective at engaging viewers in a positive, challenging way? Yet another example question is whether thought provoking elements in the media instance were much more engaging to viewers than product shots? Also, an example question includes whether certain characters, such as lead female characters, appearing in the media instance were effective for male viewers and/or across target audiences in the female demographic? Still another example question includes whether physiological responses to the media instance from the viewers were consistent with viewers identifying or associating positively with the characters in the media instance? A further question is whether the media instance was universal—performed well at connecting across gender, age, and income boundaries, or highly polarizing?

The analysis module therefore automates the analysis through use of one or more questions, as described above. The questions provide a context for analyzing and presenting the data or information received from viewers in response to the media instance. The analysis module is configured, using the received data, to answer some number of questions, where answers to the questions provide or correspond to the collected data. When a user desires results from the data for a particular media instance, the user selects a question to which they desire an answer for the media instance. In response to the question selection, the results of the analysis are presented in the form of an answer to the question, where the answer is derived or generated using the data collected and corresponding to the media instance. The results of the analysis can be presented using textual and/or graphical outputs or presentations. The results of the analysis can also be generated and presented using previous knowledge of how to represent the data to answer the question, the previous knowledge coming from similar data analyzed in the past. Furthermore, presentation of data of the media instance can be modified by the user through user or generation of other questions.

The analysis module performs the operations described above in conjunction with the presentation module, where the presentation module includes numerous different renderings for data. In operation, a rendering is specified or selected for a portion of data of a media instance, and the rendering is then tagged with one or more questions that apply to the data. This architecture allows users to modify how data is represented using a set of tools. The system remembers or stores information of how data was represented and the question or question type that was being answered. This information of prior system configurations allows the system, at a subsequent time, to self-configure to answer the same or similar questions for the same media instance or for different media instances. Users thus continually improve the ability of the system to answer questions and improve the quality of data provided in the answers.

Figure 12:
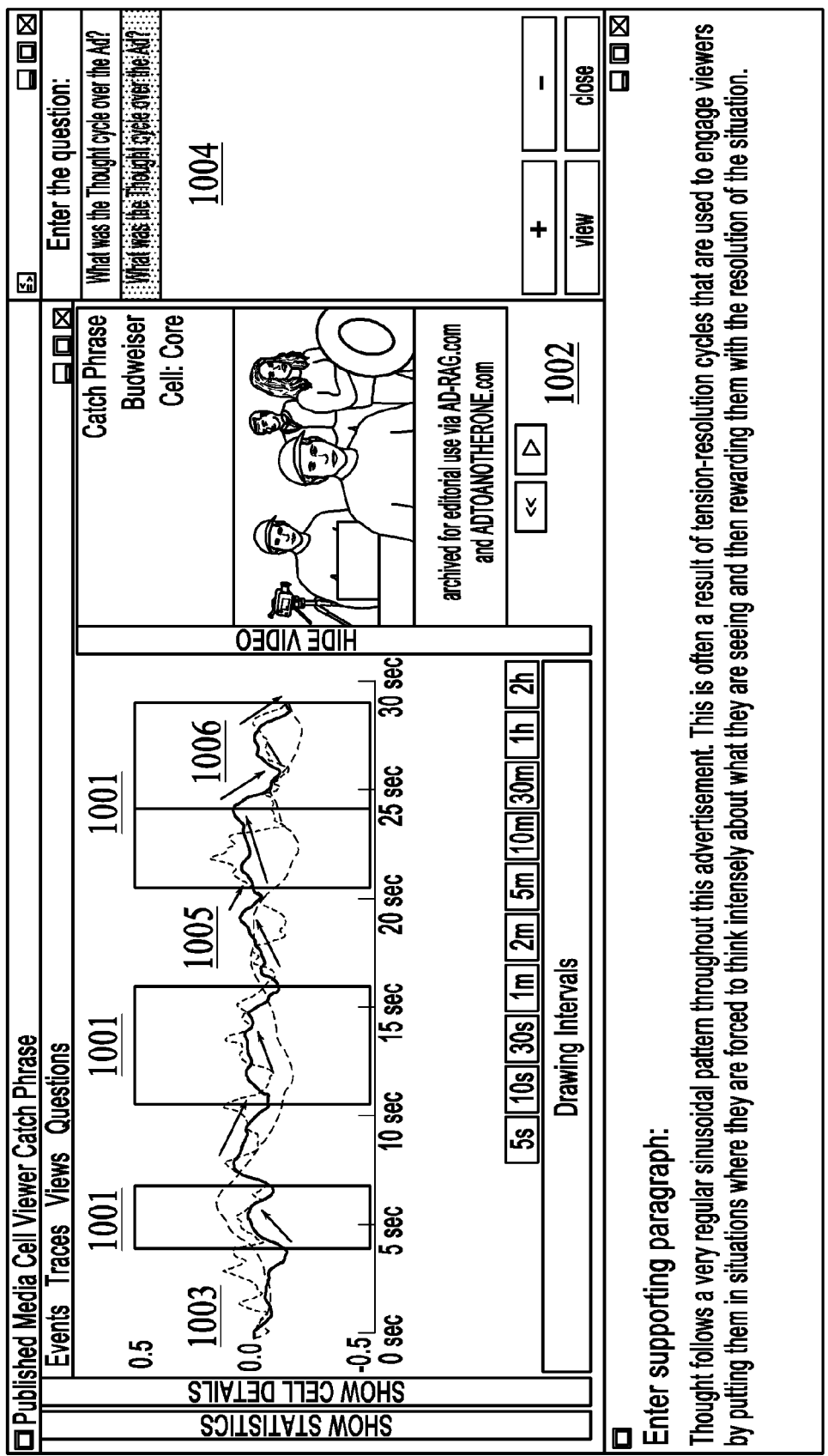
FIG. 12 shows exemplary highlights and arrows representing trends in the physiological responses from the viewers as well as verbal explanation of such markings, under an embodiment.

In some embodiments, with reference to FIG. 12, the presentation module is operable to enable the user to pick a certain section 1001 of the reactions to the media instance 1002, such as the physiological responses 1003 from the viewers shown in the reaction panel 101 via, for a non-limiting example, "shading". The analysis module 1006 may then perform the analysis requested on the shaded section of media instance and/or physiological responses automatically to illustrate the responses in a way that a lay person can take advantage of expert knowledge in parsing the viewers' reaction. The analyzed results can then be presented to the user in real time and can be shared with other people.

In some embodiments, the analysis module is operable to analyze the shaded section of the media instance and/or responses by being preprogrammed either by an analyst or the user themselves. Usually, a user is most often interested in a certain number of attributes of the viewers' responses.

The analysis module provides the user with insights, conclusions, and findings that they can review from the bottom up. Although the analysis result provides inside and in-depth analysis of the data as well as various possible interpretations of the shaded section of the media instance, which often leaves a conclusion evident, such analysis, however, is no substitute for reaching conclusion by the user. Instead the user is left to draw his/her own conclusion about the section based on the analysis provided.

In some embodiments, a user may pick a section and choose one of the questions/tasks/requests 1004 that he/she is interested in from a prepared list. The prepared list of questions may include but is not limited to any number of questions. Some example questions follow along with a response evoked in the analysis module.

An example question is "Where were there intense responses to the media instance?" In response the analysis module may calculate the intensity of the responses automatically by looking for high coherence areas of responses.

Another example question is "Does the media instance end on a happy note?" or "Does the audience think the event (e.g., joke) is funny?" In response the analysis module may check if the physiological data shows that viewer acceptance or approval is higher in the end than at the beginning of the media instance.

Yet another example question is "Where do people engage in the spot?" In response to this question the analysis module may check if there is a coherent change in viewers' emotions.

Still another example question is "What is the response to the brand moment?" In response the analysis module may check if thought goes up, but acceptance or approval goes down during the shaded section of the media.

An additional example question is "Which audience does the product introduction work on best?" In response the analysis module analyzes the responses from various segments of the viewers, which include but are not limited to, males, females, gamers, republicans, engagement relative to an industry, etc.

In some embodiments, the presentation module (FIG. 10, 1807) is operable to present the analysis results in response to the questions raised together with the viewers' reactions to the user graphically on the interactive browser. For non-limiting examples, line highlights 1005 and arrows 1006 representing trends in the physiological responses from the viewers can be utilized as shown in FIG. 12, where highlights mark one or more specific physiological responses to be analyzed and the up/down arrows indicate rise/fall in the corresponding responses. In addition, other graphic markings can also be used, which can be but are not limited to, text boxes, viewing data from multiple groups at once (comparing men to women) and any graphic tools that are commonly used to mark anything important. For another non-limiting example, a star, dot and/or other graphic element may be used to mark the point where there is the first coherent change and a circle may be used to mark the one with the strongest response.

In some embodiments, verbal explanation 1007 of the analysis results in response to the questions raised can be provided to the user together with graphical markings shown in FIG. 12. Such verbal explanation describes the graphical markings (e.g., why an arrow rises, details about the arrow, etc.). For the non-limiting example of an advertisement video clip shown in FIG. 12, verbal explanation 1007 states that "Thought follows a very regular sinusoidal pattern throughout this advertisement. This is often a result of tension-resolution cycles that are used to engage viewers by putting them in situations where they are forced to think intensely about what they are seeing and then rewarding them with the resolution of the situation." For another non-limiting example of a joke about a man hit by a thrown rock, the verbal explanation may resemble something like: "The falling of the man after being hit by a rock creates the initial coherent, positive response in liking. This shows that the actual rock throw is not funny, but the arc that the person's body takes is. After the body hits the ground, the response reverts to neutral and there are no further changes in emotions during this section."

In some embodiments, with reference to FIG. 10, an optional authentication module 1813 is operable to authenticate identity of the user requesting access to the media instance and the verbatim reactions remotely over a network 1812. Here, the network can be but is not limited to, internet, intranet, wide area network (WAN), local area network (LAN), wireless network, Bluetooth, and mobile communication network.

In some embodiments, optional user database 1814 stores information of users who are allowed to access the media instances and the verbatim reactions from the viewers, and the specific media instances and the reactions each user is allowed to access. The access module 1810 may add or remove a user for access, and limit or expand the list of media instances and/or reactions the user can access and/or the analysis features the user can use by checking the user's login name and password. Such authorization/limitation on a user's access can be determined to based upon who the user is, e.g., different amounts of information for different types of users. For a non-limiting example, Company ABC can have access to certain ads and feedbacks from viewers' reactions to the ads, to which Company XYZ can not have access or can have only limited access.

An embodiment synchronizes a specific media instance with physiological responses to the media instance from a plurality of viewers continuously over the entire time duration of the media instance. Once the media instance and the physiological responses are synchronized, an interactive browser enables a user to navigate through the media instance (or the physiological responses) in one panel while presenting the corresponding physiological responses (or the section of the media instance) at the same point in time in another panel.

The interactive browser allows the user to select a section/scene from the media instance, correlate, present, and compare the viewers' physiological responses to the particular section. Alternatively, the user may monitor the viewers' physiological responses continuously as the media instance is being displayed. Being able to see the continuous (instead of static snapshot of) changes in physiological responses and the media instance side by side and compare aggregated physiological responses from the viewers to a specific event of the media instance in an interactive way enables the user to obtain better understanding of the true reaction from the viewers to whatever stimuli being presented to them.

Figure 13:
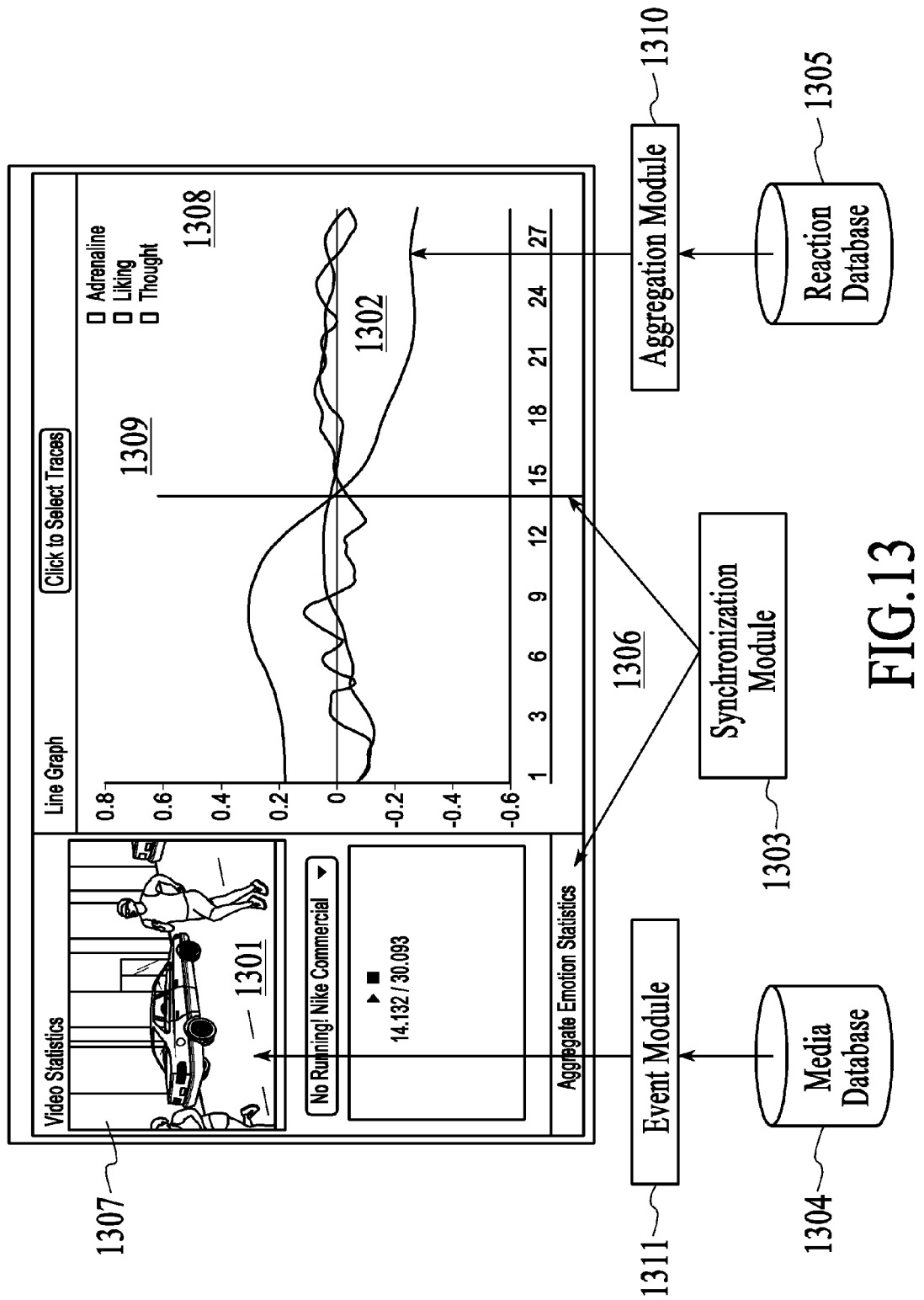
FIG. 13 is a system to support synchronization of media with physiological responses from viewers, under an embodiment.

FIG. 13 is an illustration of an exemplary system to support synchronization of media with physiological responses from viewers of the media. Although this diagram depicts components as functionally separate, such depiction is merely for illustrative purposes. It will be apparent to those skilled in the art that the components portrayed in this figure can be arbitrarily combined or divided into separate software, firmware and/or hardware components. Furthermore, it will also be apparent to those skilled in the art that such components, regardless of how they are combined or divided, can execute on the same computing device or multiple computing devices, and wherein the multiple computing devices can be connected by one or more networks.

Referring to FIG. 13, a synchronization module 1303 is operable to synchronize and correlate a media instance 1301 with one or more physiological responses 1302 aggregated from one or more viewers of the media instance continuously at each and every moment over the entire duration of the media instance. Here, the media instance and its pertinent data can be stored in a media database 1304, and the one or more physiological responses aggregated from the viewers can be stored in a reaction database 1305, respectively. An interactive browser 1306 comprises at least two panels including a media panel 1307, which is operable to present, play, and pause the media instance, and a reaction panel 1308, which is operable to display and compare the one or more physiological responses (e.g., Adrenaline, Liking, and Thought) corresponding to the media instance as lines (traces) in a two-dimensional line graph. A horizontal axis of the graph represents time, and a vertical axis represents the amplitude (intensity) of the one or more physiological responses. A cutting line 1309 marks the physiological responses from the viewers to the current scene (event, section, or moment in time) of the media instance, wherein the cutting line can be chosen by the user and move in coordination with the media instance being played. The interactive browser enables the user to select an event/section/scene/moment from the media instance presented in the media panel 1307 and correlate, present, and compare the viewers' physiological responses to the particular section in the reaction panel 1308. Conversely, interactive browser also enables the user to select the cutting line 1309 of physiological responses from the viewers in the reaction panel 1308 at any specific moment, and the corresponding media section or scene can be identified and presented in the media panel 1307.

The synchronization module 1303 of an embodiment synchronizes and correlates a media instance 1301 with one or more physiological responses 1302 aggregated from a plurality of viewers of the media instance by synchronizing each event of the media. The physiological response data of a person includes but is not limited to heart rate, brain waves, electroencephalogram (EEG) signals, blink rate, breathing, motion, muscle movement, galvanic skin response, skin temperature, and any other physiological response of the person. The physiological response data corresponding to each event or point in time is then retrieved from the media database 1304. The data is offset to account for cognitive delays in the human brain corresponding to the signal collected (e.g., the cognitive delay of the brain associated with human vision is different than the cognitive delay associated with auditory information) and processing delays of the system, and then synchronized with the media instance 1301. Optionally, an additional offset may be applied to the physiological response data 1302 of each individual to account for time zone differences between the view and reaction database 1305.

Figure 14:
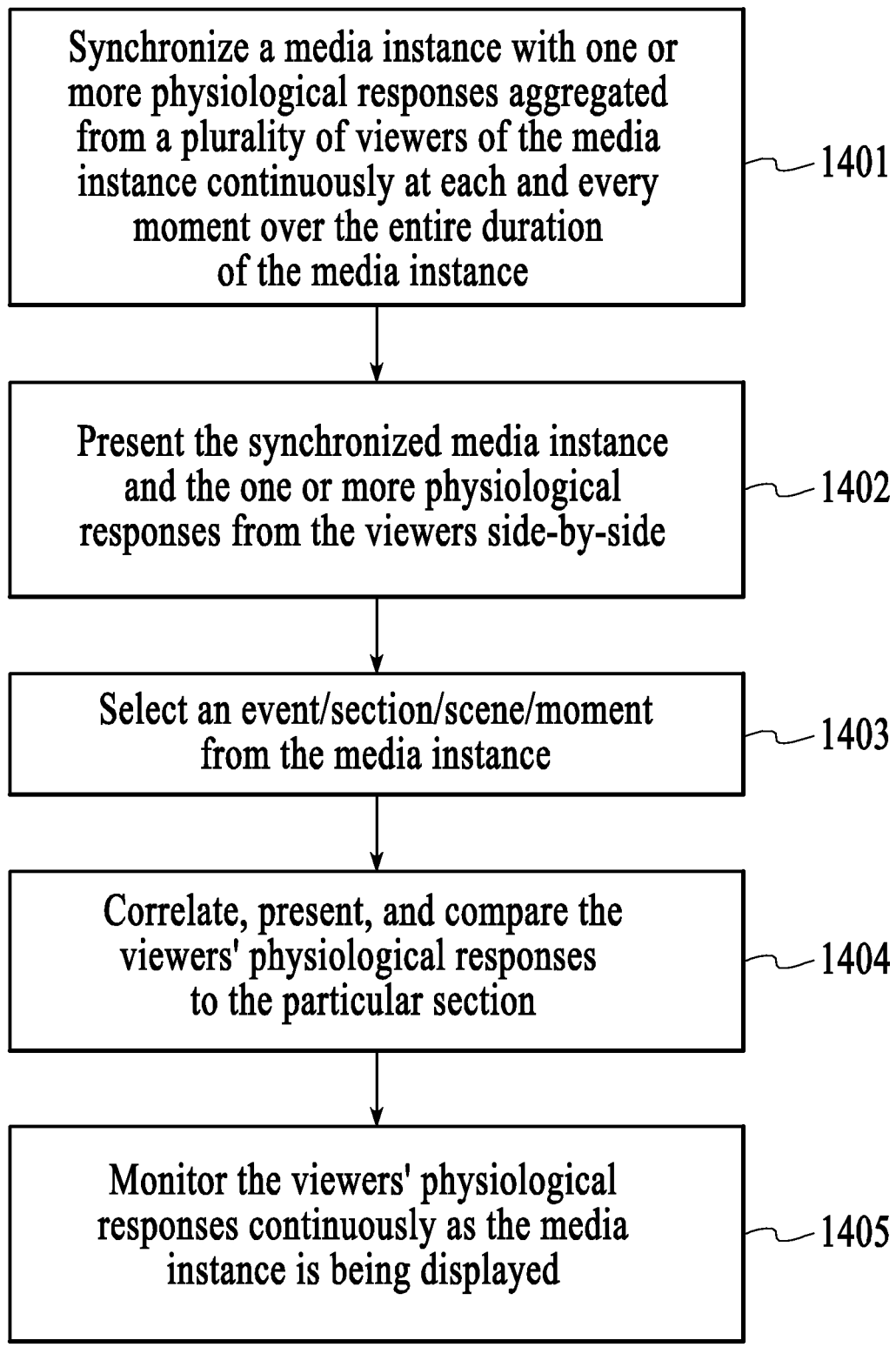
FIG. 14 is a flow chart for synchronization of media with physiological responses from viewers, under an embodiment.

FIG. 14 is a flow chart illustrating an exemplary process to support synchronization of media with physiological responses from viewers of the media. Although this figure depicts functional operations in a particular order for purposes of illustration, the process is not limited to any particular order or arrangement of operations. One skilled in the art will appreciate that the various operations portrayed in this figure could be omitted, rearranged, combined and/or adapted in various ways.

Referring to FIG. 14, a media instance is synchronized with one or more physiological responses aggregated from a plurality of viewers of the media instance continuously at each and every moment over the entire duration of the media instance at 1401. At 1402, the synchronized media instance and the one or more physiological responses from the viewers are presented side-by-side. An event/section/scene/moment from the media instance can be selected at 1403, and the viewers' physiological responses to the particular section can be correlated, presented, and compared at 1404. Alternatively, the viewers' physiological responses can be monitored continuously as the media instance is being displayed at 1405.

In some embodiments, with reference to FIG. 13, an aggregation module 1310 is operable to retrieve from the reaction database 1305 and aggregate the physiological responses to the media instance across the plurality of viewers and present each of the aggregated responses as a function over the duration of the media instance. The aggregated responses to the media instance can be calculated via one or more of: max, min, average, deviation, or a higher ordered approximation of the intensity of the physiological responses from the viewers.

In some embodiments, change (trend) in amplitude of the aggregated responses is a good measure of the quality of the media instance. If the media instance is able to change viewers emotions up and down in a strong manner (for a non-limiting example, mathematical deviation of the response is large), such strong change in amplitude corresponds to a good media instance that puts the viewers into different emotional states. In contrast, a poor performing media instance does not put the viewers into different emotional states. Such information can be used by media designers to identify if the media instance is eliciting the desired response and which key events/scenes/sections of the media instance need to be changed in order to match the desired response. A good media instance should contain multiple moments/scenes/events that are intense and produce positive amplitude of response across viewers. A media instance failed to create such responses may not achieve what the creators of the media instance have intended.

In some embodiments, the media instance can be divided up into instances of key moments/events/scenes/segments/sections in the profile, wherein such key events can be identified and/tagged according to the type of the media instance. In the case of video games, such key events include but are not limited to, elements of a video game such as levels, cut scenes, major fights, battles, conversations, etc. In the case of Web sites, such key events include but are not limited to, progression of Web pages, key parts of a Web page, advertisements shown, content, textual content, video, animations, etc. In the case of an interactive media/movie/ads, such key events can be but are not limited to, chapters, scenes, scene types, character actions, events (for non-limiting examples, car chases, explosions, kisses, deaths, jokes) and key characters in the movie.

In some embodiments, an event module 1311 can be used to quickly identify a numbers of moments/events/scenes/segments/sections in the media instance retrieved from the media database 1304 and then automatically calculate the length of each event. The event module may enable each user, or a trained administrator, to identify and tag the important events in the media instance so that, once the "location" (current event) in the media instance (relative to other pertinent events in the media instance) is selected by the user, the selected event may be better correlated with the aggregated responses from the viewers.

In some embodiments, the events in the media instance can be identified, automatically if possible, through one or more applications that parse user actions in an environment (e.g., virtual environment, real environment, online environment, etc.) either before the viewer's interaction with the media instance in the case of non-interactive media such as a movie, or afterwards by reviewing the viewer's interaction with the media instance through recorded video, a log of actions or other means. In video games, web sites and other electronic interactive media instance, the program that administers the media can create this log and thus automate the process.

An embodiment enables graphical presentation and analysis of verbatim comments and feedbacks from a plurality of viewers to a specific media instance. These verbatim comments are first collected from the viewers and stored in a database before being analyzed and categorized into various categories. Once categorized, the comments can then be presented to a user in various graphical formats, allowing the user to obtain an intuitive visual impression of the positive/negative reactions to and/or the most impressive characteristics of the specific media instance as perceived by the viewers.

An embodiment enables graphical presentation and analysis of verbatim comments and feedbacks from a plurality of viewers to a specific media instance. These verbatim comments are first collected from the viewers and stored in a database before being analyzed and categorized into various categories. Once categorized, the comments can then be presented to a user in various graphical formats, allowing the user to obtain an intuitive visual impression of the positive/negative reactions to and/or the most impressive characteristics of the specific media instance, as perceived by the viewers. Instead of parsing through and dissecting the comments and feedbacks word by word, the user is now able to visually evaluate how well the media instance is being received by the viewers at a glance.

Figure 15:
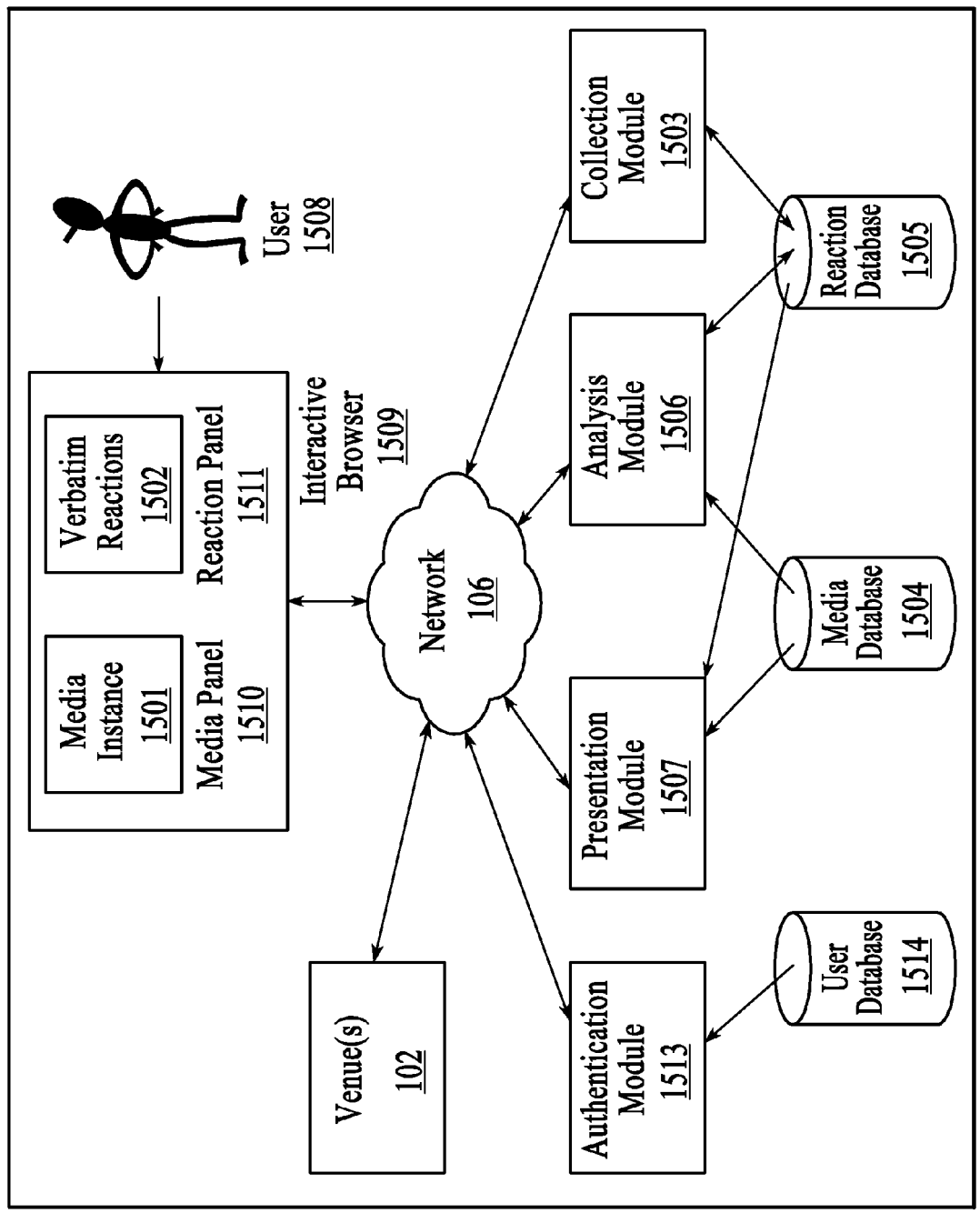
FIG. 15 is a system to support graphical presentation of verbatim comments from viewers, under an embodiment.

FIG. 15 is an illustration of an exemplary system to support graphical presentation of verbatim comments from viewers. Although this diagram depicts components as functionally separate, such depiction is merely for illustrative purposes. It will be apparent to those skilled in the art that the components portrayed in this figure can be arbitrarily combined or divided into separate software, firmware and/or hardware components. Furthermore, it will also be apparent to those skilled in the art that such components, regardless of how they are combined or divided, can execute on the same computing device or multiple computing devices, and wherein the multiple computing devices can be connected by one or more networks.

Referring to FIG. 15, a collection module 1503 is operable to collect, record, store and manage verbatim reactions 1502 (comments and feedbacks) from a plurality of viewers of a media instance 1501. Here, the media instance and its pertinent data can be stored in a media database 1504, and the verbatim reactions from the viewers can be stored in a reaction database 1505, respectively. An analysis module 1506 is operable to analyze the verbatim comments from the viewers and categorize them into the plurality of categories. A presentation module 1507 is operable to retrieve and categorize the verbatim reactions to the media instance into various categories, and then present these verbatim reactions to a user 1508 based on their categories in graphical forms via an interactive browser 1509. The interactive browser includes at least two panels: a media panel 1510, which is operable to present, play, and pause the media instance; and a comments panel 1511, which is operable to display not only the one or more reactions corresponding to the media instance, but also one or more graphical categorization and presentation of the verbatim reactions to provide the user with both a verbal and/or a visual perception and interpretation of the feedbacks from the viewers.

Figure 16:
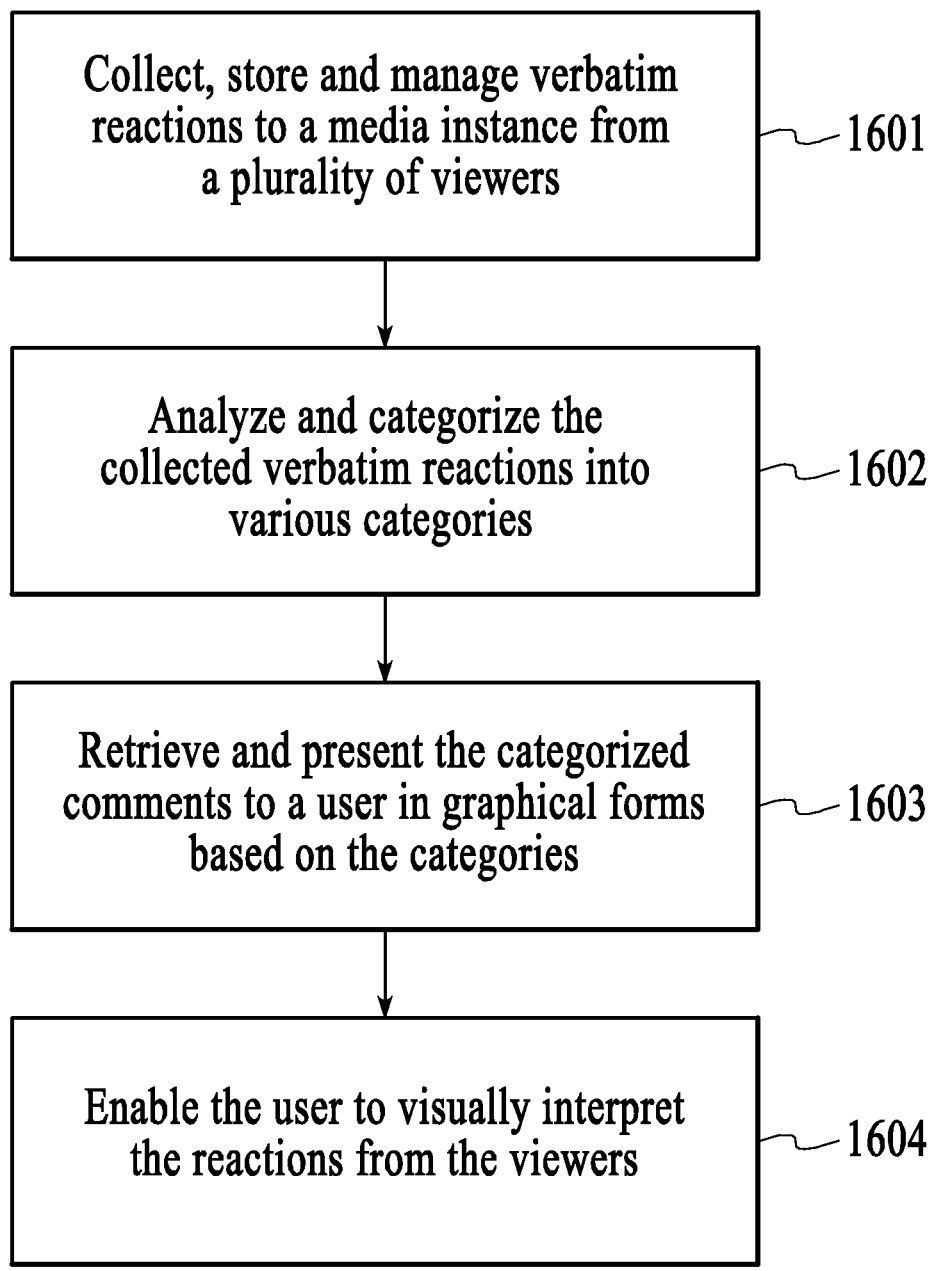
FIG. 16 is a flow chart for graphical presentation of verbatim comments from viewers, under an embodiment.

FIG. 16 is a flow chart illustrating an exemplary process to support graphical presentation of verbatim comments from viewers. Although this figure depicts functional operations in a particular order for purposes of illustration, the process is not limited to any particular order or arrangement of operations. One skilled in the art will appreciate that the various operations portrayed in this figure could be omitted, rearranged, combined and/or adapted in various ways.

Referring to FIG. 16, verbatim reactions to a media instance from a plurality of viewers are collected, stored and managed at 1601. At 1602, the collected verbatim reactions are analyzed and categorized into various categories. The categorized comments are then retrieved and presented to a user in graphical forms based on the categories at 1603, enabling the user to visually interpret the reactions from the viewers at 1604.

In some embodiments, the viewers of the media instance are free to write what they like and don't like about the media instance, and the verbatim (free flowing text) comments or feedback 501 from the viewers can be recorded and presented in the comments panel 7111 verbatim as shown in FIG. 9 described above. In some embodiments, the analysis module is operable to further characterize the comments in each of the plurality of categories are as positive or negative based on the words used in each of the comments. Once characterized, the number of positive or negative comments in each of the categories can be summed up. For a non-limiting example, comments from viewers on a certain type of events, like combat, can be characterized and summed up as being 40% positive, while 60% negative. Such an approach avoids single verbatim response from bias the responses from a group of viewers, making it easy for the user to understand how viewers would react to every aspect of the media instance.

In some embodiments, the analysis module is operable to characterize the viewers' comments about the media instance as positive or negative in a plurality of categories/topics/aspects related to the product, wherein such categories include but are not limited to, product, event, logo, song, spokesperson, jokes, narrative, key events, storyline. These categories may not be predetermined, but instead be extracted from the analysis of their comments.

In some embodiments, the presentation module is operable to present summation of the viewers' positive and negative comments to various aspects/topics/events of the media instance to the user (creator of the media instance) in a bubble graph for example. In alternative embodiments, the verbatim comments from the viewers can be analyzed, and key words and concepts (adjectives) can be extracted and presented in a word cloud, rendering meaningful information from the verbatim comments more accessible.

In some embodiments, the viewers may simply be asked to answer a specific question, for example, "What are three adjectives that best describe your response to this media." The adjectives in the viewers' responses to the question can then be collected, categorized, and summed up, and presented in a Word cloud. Alternatively, the adjectives the viewers used to describe their responses to the media instance may be extracted from collected survey data.

In some embodiments, with reference to FIG. 15, an optional authentication module 1513 is operable to authenticate identity of the user requesting access to the media instance and the verbatim reactions remotely over a network 1513. Here, the network can be but is not limited to, internet, intranet, wide area network (WAN), local area network (LAN), wireless network, Bluetooth, and mobile communication network.

In some embodiments, optional user database 1514 stores information of users who are allowed to access the media instances and the verbatim reactions from the viewers, and the specific media instances and the reactions each user is allowed to access. The access module 1510 may add or remove a user for access, and limit or expand the list of media instances and/or reactions the user can access and/or the analysis features the user can use by checking the user's login name and password. Such authorization/limitation on a user's access can be determined to based upon who the user is, e.g., different amounts of information for different types of users. For a non-limiting example, Company ABC can have access to certain ads and feedback from viewers' reactions to the ads, while Company XYZ can not have access or can only have limited access to the same ads and/or feedback.

The headset of an embodiment (also referred to herein as a sensor headset and/or integrated headset) integrates sensors into a housing which can be placed on a human head for measurement of physiological data, as described above. The device includes at least one sensor and a reference electrode connected to the housing. A processor coupled to the sensor and the reference electrode receives signals that represent electrical activity in tissue of a user. The processor generates an output signal including data of a difference between an energy level in each of a first and second frequency band of the signals. The difference between energy levels is proportional to release level present time emotional state of the user. The device includes a wireless transmitter that transmits the output signal to a remote device. The device therefore processes the physiological data to create the output signal that correspond to a person's mental and emotional state or response.

Figure 17:
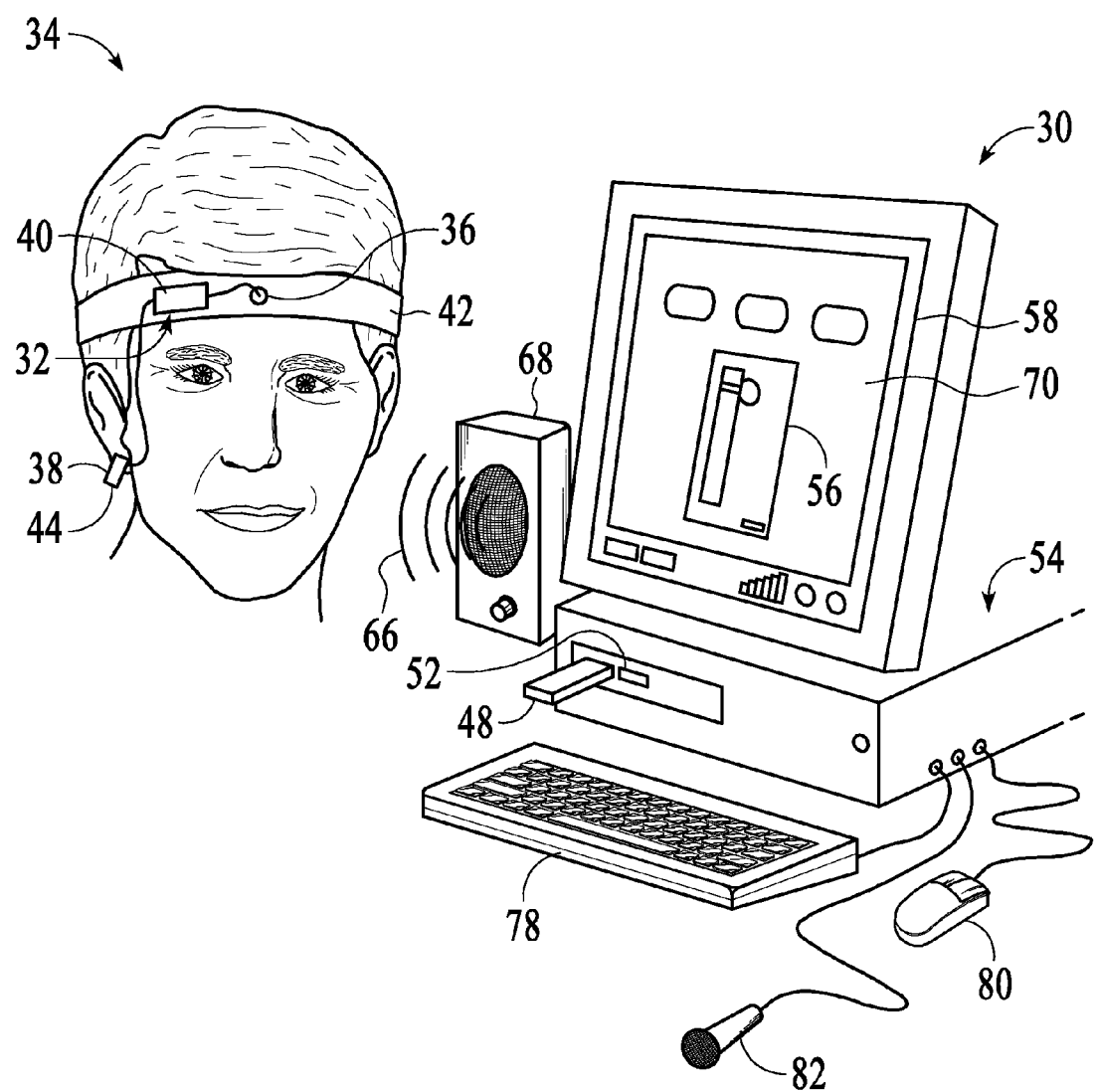
FIG. 17 is a system which uses a sensor headset which measures electrical activity to determine a present time emotional state of a user, under an embodiment.

A system 30 which includes the headset is shown in FIG. 17. Exemplary system 30 includes a sensor device 32 which is connected to a user 34 for sensing and isolating a signal of interest from electrical activity in the user's pre-frontal lobe. The signal of interest has a measurable characteristic of electrical activity, or signal of interest, which relates to a present time emotional state (PTES) of user 34. PTES relates to the emotional state of the user at a given time. For instance, if the user is thinking about something that causes the user emotional distress, then the PTES is different than when the user is thinking about something which has a calming affect on the emotions of the user. In another example, when the user feels a limiting emotion regarding thoughts, then the PTES is different than when the user feels a state of release regarding those thoughts. Because of the relationship between the signal of interest and PTES, system 30 is able to determine a level of PTES experienced by user 34 by measuring the electrical activity and isolating a signal of interest from other electrical activity in the user's brain.

In the present example, sensor device 32 includes a sensor electrode 36 which is positioned at a first point and a reference electrode 38 which is positioned at a second point. The first and second points are placed in a spaced apart relationship while remaining in close proximity to one another. The points are preferably within about 8 inches of one another, and in one instance the points are about 4 inches apart. In the present example, sensor electrode 36 is positioned on the skin of the user's forehead and reference electrode 38 is connected to the user's ear. The reference electrode can also be attached to the user's forehead, which may include positioning the reference electrode over the ear of the user.

Sensor electrode 36 and reference electrode 38 are connected to an electronics module 40 of sensor device 32, which is positioned near the reference electrode 38 to that they are located substantially in the same noise environment. The electronics module 40 may be located at or above the temple of the user or in other locations where the electronics module 40 is in close proximity to the reference electrode 38. In the present example, a head band 42 or other mounting device holds sensor electrode 36 and electronics module 40 in place near the temple while a clip 44 holds reference electrode 38 to the user's ear. In one instance, the electronics module and reference electrode are positioned relative to one another such that they are capacitively coupled.

Sensor electrode 36 senses the electrical activity in the user's pre-frontal lobe and electronics module 40 isolates the signal of interest from the other electrical activity present and detected by the sensor electrode. Electronics module 40 includes a wireless transmitter 46, which transmits the signal of interest to a wireless receiver 48 over a wireless link 50. Wireless receiver 48 receives the signal of interest from electronics module 40 and connects to a port 52 of a computer 54, or other device having a processor, with a port connector 53 to transfer the signal of interest from wireless receiver 48 to computer 54. Electronics module 40 includes an LED 55, and wireless receiver 48 includes an LED 57 which both illuminate when the wireless transmitter and the wireless receiver are powered.

Levels of PTES derived from the signal of interest can be displayed on a computer screen 58 of computer 54 (e.g., in a meter 56). In this embodiment, the display meter 56 serves as an indicator, but the embodiments are not so limited. Viewing meter 56 allows user 34 to determine their level of PTES at any particular time in a manner which is objective. The objective feedback obtained from meter 56 is used for guiding the user to improve their PTES, to determine levels of PTES related to particular memories or thoughts which can be brought up in the mind of user 34 when the user is exposed to certain stimuli, and/or to provide feedback to the user as to the quality of data received from the user's headset and, thus, the proper fit of the headset.

In system 30, media material or media instance 66 is used to expose user 34 to stimuli designed to cause user 34 to bring up particular thoughts or emotions which are related to a high level of PTES in the user. In the present example, media material 66 includes any material presented or played to the user. The particular thoughts or emotions are represented in the signal of interest captured during play of the media instance.

The signal of interest which relates to the release level PTES are brain waves or electrical activity in the pre-frontal lobe of the user's brain in the range of 4-12 Hz. These characteristic frequencies of electrical activity are in the Alpha and Theta bands. Alpha band activity is in the 8 to 12 Hz range and Theta band activity is in the 4 to 7 Hz range. A linear relationship between amplitudes of the Alpha and Theta bands is an indication of the release level. When user 34 is in a non-release state, the activity is predominantly in the Theta band and the Alpha band is diminished; and when user 34 is in a release state the activity is predominantly in the Alpha band and the energy in the Theta band is diminished.

Figure 18:
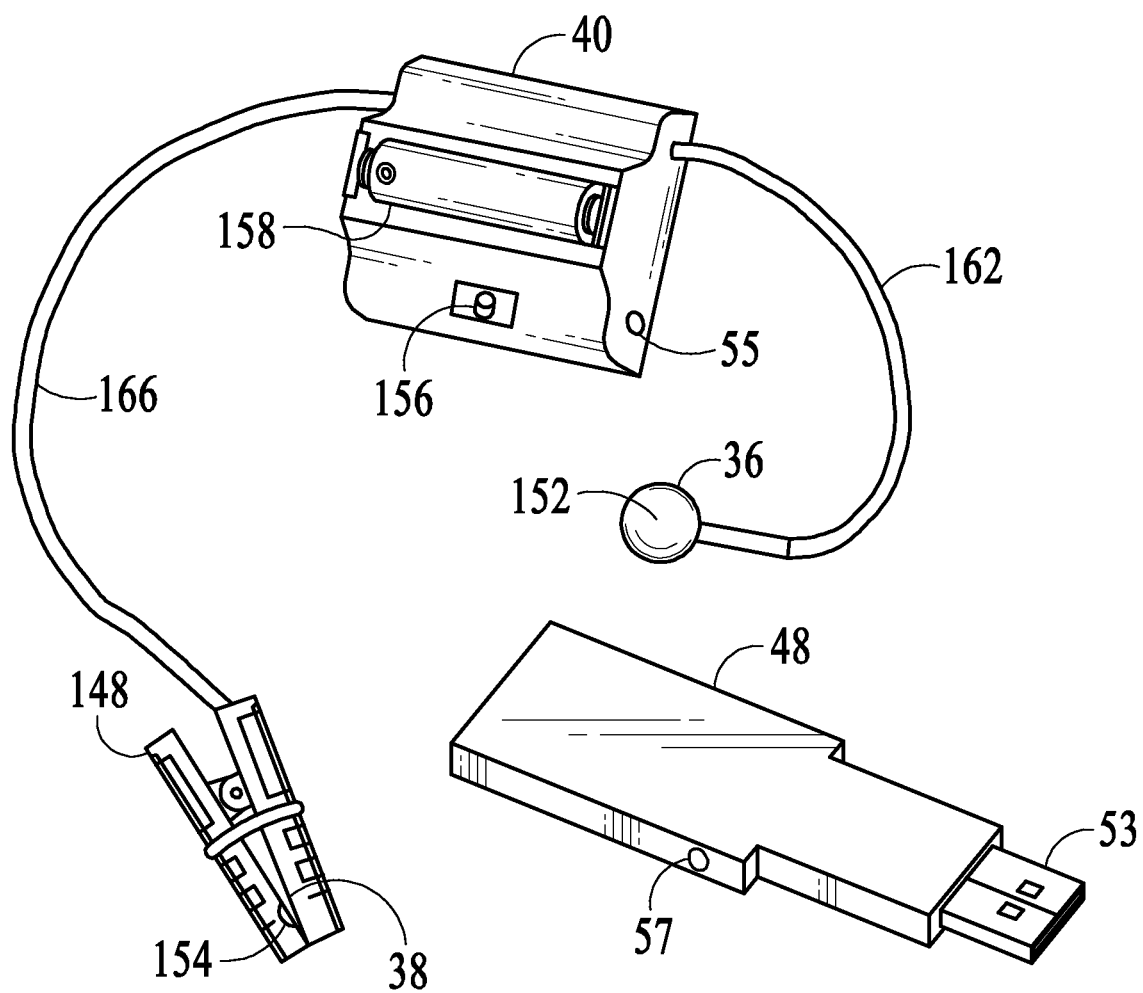
FIG. 18 is a perspective view of the sensor headset, under an embodiment.
Figure 19:
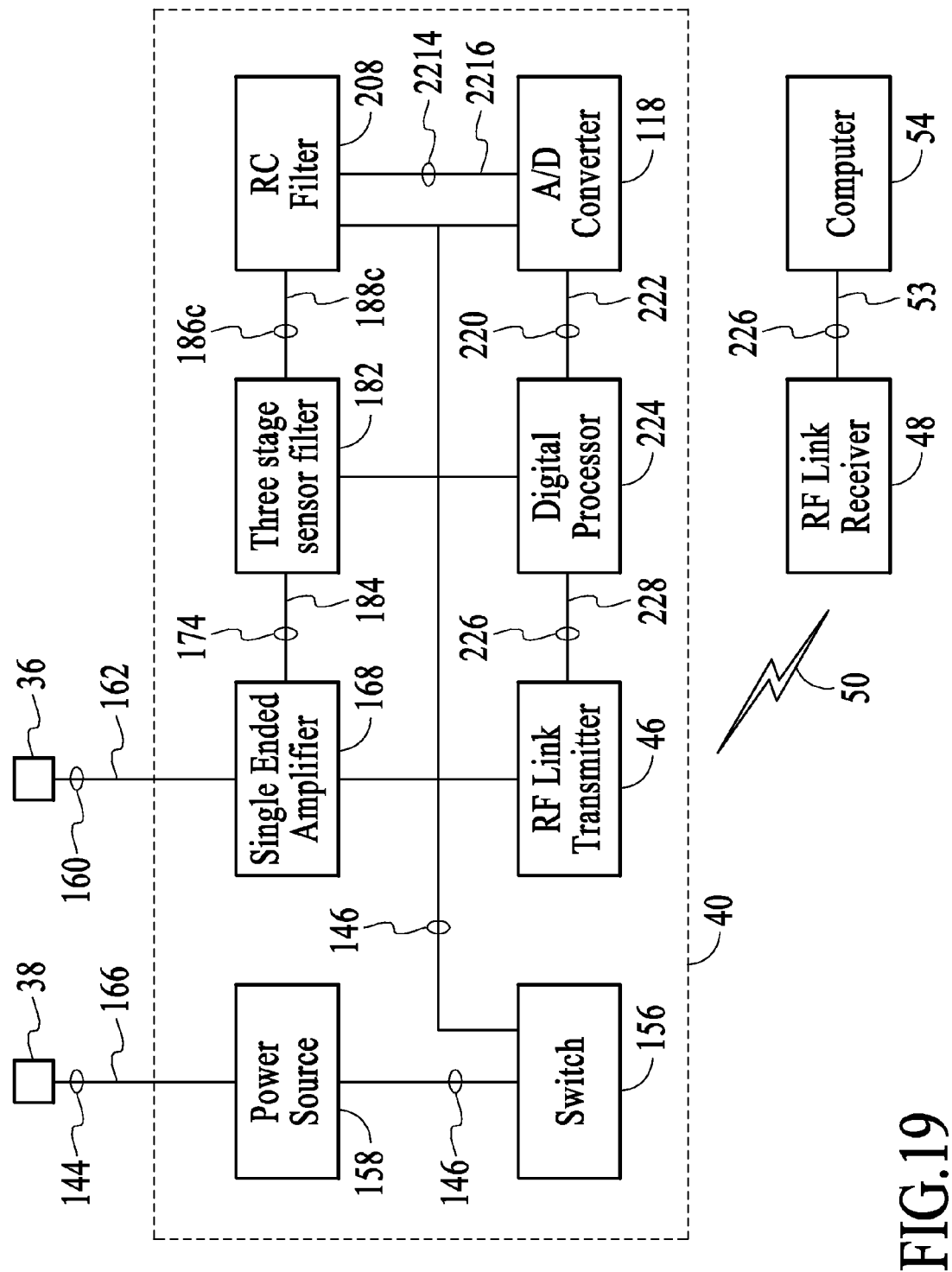
FIG. 19 is a block diagram of the sensor headset and a computer, under an embodiment.

One example of sensor device 32 that captures signals of interest is shown in FIGS. 18 and 19. Sensor device 32 includes sensor electrode 36, reference electrode 38 and electronics module 40. The electronics module 40 amplifies the signal of interest by 1,000 to 100,000 times while at the same time insuring that 60 Hz noise is not amplified at any point. Electronics module 40 isolates the signal of interest from undesired electrical activity.

Sensor device 32 in the present example also includes wireless receiver 48 which receives the signal of interest from the electronics module over wireless link 50 and communicates the signal of interest to computer 54. In the present example, wireless link 50 uses radiofrequency energy; however other wireless technologies may also be used, such as infrared. Using a wireless connection eliminates the need for wires to be connected between the sensor device 32 and computer 54 which electrically isolates sensor device 32 from computer 54.

Reference electrode 38 is connected to a clip 148 which is used for attaching reference electrode 38 to an ear 150 of user 34, in the present example. Sensor electrode 36 includes a snap or other spring loaded device for attaching sensor electrode 36 to headband 42. Headband 42 also includes a pocket for housing electronics module 40 at a position at the user's temple. Headband 42 is one example of an elastic band which is used for holding the sensor electrode and/or the electronics module 40, another types of elastic bands which provide the same function could also be used, including having the elastic band form a portion of a hat.

Other types of mounting devices, in addition to the elastic bands, can also be used for holding the sensor electrode against the skin of the user. A holding force holding the sensor electrode against the skin of the user can be in the range of 1 to 4 oz. The holding force can be, for instance, 1.5 oz.

In another example of a mounting device involves a frame that is similar to an eyeglass frame, which holds the sensor electrode against the skin of the user. The frame can also be used for supporting electronics module 40. The frame is worn by user 34 in a way which is supported by the ears and bridge of the nose of the user, where the sensor electrode 36 contacts the skin of the user.

Sensor electrode 36 and reference electrode 38 include conductive surface 152 and 154, respectively, that are used for placing in contact with the skin of the user at points where the measurements are to be made. In the present example, the conductive surfaces are composed of a non-reactive material, such as copper, gold, conductive rubber or conductive plastic. Conductive surface 152 of sensor electrode 36 may have a surface area of approximately ½ square inch. The conductive surfaces 152 are used to directly contact the skin of the user without having to specially prepare the skin and without having to use a substance to reduce a contact resistance found between the skin and the conductive surfaces.

Sensor device 32 works with contact resistances as high as 500,000 ohms which allows the device to work with conductive surfaces in direct contact with skin that is not specially prepared. In contrast, special skin preparation and conductive gels or other substances are used with prior EEG electrodes to reduce the contact resistances to around 20,000 ohms or less. One consequence of dealing with higher contact resistance is that noise may be coupled into the measurement. The noise comes from lights and other equipment connected to 60 Hz power, and also from friction of any object moving through the air which creates static electricity. The amplitude of the noise is proportional to the distance between the electronics module 40 and the reference electrode 38. In the present example, by placing the electronics module over the temple area, right above the ear and connecting the reference electrode to the ear, the sensor device 32 does not pick up the noise, or is substantially unaffected by the noise. By positioning the electronics module in the same physical space with the reference electrode and capacitively coupling the electronics module with the reference electrode ensures that a local reference potential 144 in the electronics module and the ear are practically identical in potential. Reference electrode 38 is electrically connected to local reference potential 144 used in a power source 158 for the sensor device 32.

Power source 158 provides power 146 to electronic components in the module over power conductors. Power source 158 provides the sensor device 32 with reference potential 144 at 0 volts as well as positive and negative source voltages, −VCC and +VCC. Power source 158 makes use of a charge pump for generating the source voltages at a level which is suitable for the electronics module.

Power source is connected to the other components in the module 40 though a switch 156. Power source 158 can include a timer circuit which causes electronics module 40 to be powered for a certain time before power is disconnected. This feature conserves power for instances where user 34 accidentally leaves the power to electronics module 40 turned on. The power 146 is referenced locally to measurements and does not have any reference connection to an external ground system since sensor circuit 32 uses wireless link 50.

Sensor electrode 36 is placed in contact with the skin of the user at a point where the electrical activity in the brain is to be sensed or measured. Reference electrode 38 is placed in contact with the skin at a point a small distance away from the point where the sensor electrode is placed. In the present example, this distance is 4 inches, although the distance may be as much as about 8 inches. Longer lengths may add noise to the system since the amplitude of the noise is proportional to the distance between the electronics module and the reference electrode. Electronics module 40 is placed in close proximity to the reference electrode 38. This causes the electronics module 40 to be in the same of electrical and magnetic environment is the reference electrode 38 and electronics module 40 is connected capacitively and through mutual inductance to reference electrode 38. Reference electrode 38 and amplifier 168 are coupled together into the noise environment, and sensor electrode 36 measures the signal of interest a short distance away from the reference electrode to reduce or eliminate the influence of noise on sensor device 32. Reference electrode 38 is connected to the 0V in the power source 158 with a conductor 166.

Sensor electrode 36 senses electrical activity in the user's brain and generates a voltage signal 160 related thereto which is the potential of the electrical activity at the point where the sensor electrode 36 contacts the user's skin relative to the local reference potential 144. Voltage signal 160 is communicated from the electrode 36 to electronics module 40 over conductor 162. Conductors 162 and 166 are connected to electrodes 36 and 38 in such a way that there is no solder on conductive surfaces 152 and 154. Conductor 162 is as short as practical, and in the present example is approximately 3 inches long. When sensor device 32 is used, conductor 162 is held a distance away from user 34 so that conductor 162 does not couple signals to or from user 34. In the present example, conductor 162 is held at a distance of approximately ½" from user 34. No other wires, optical fibers or other types of extensions extend from the electronics module 40, other than the conductors 162 and 166 extending between module 40 and electrodes 36 and 38, since these types of structure tend to pick up electronic noise.

Figure 20:
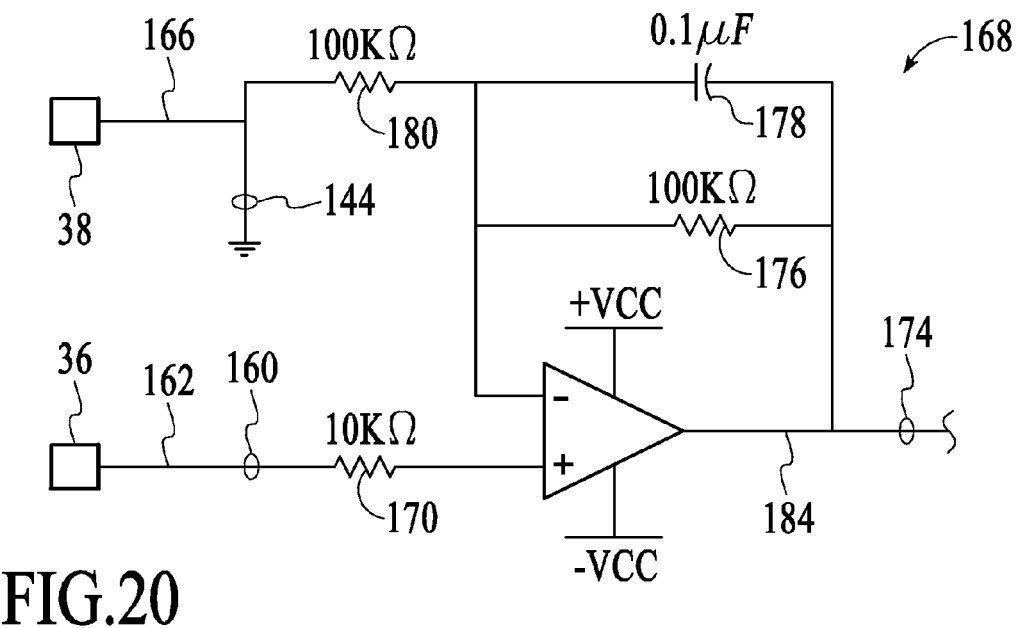
FIG. 20 is a circuit diagram of an amplifier of the sensor headset, under an embodiment.

The electronics module 40 measures or determines electrical activity, which includes the signal of interest and other electrical activity unrelated to the signal of interest which is undesired. Electronics module 40 uses a single ended amplifier 168, (FIGS. 19 and 20), which is closely coupled to noise in the environment of the measurement with the reference electrode 38. The single ended amplifier 168 provides a gain of 2 for frequencies up to 12 Hz, which includes electrical activity in the Alpha and Theta bands, and a gain of less than 1 for frequencies 60 Hz and above, including harmonics of 60 Hz.

Amplifier 168 (FIGS. 20 and 23) receives the voltage signal 160 from electrode 36 and power 146 from power source 158. Single ended amplifier 168 generates an output signal 174 which is proportional to voltage signal 160. Output signal 174 contains the signal of interest. In the present example, voltage signal 160 is supplied on conductor 162 to a resistor 170 which is connected to non-inverting input of high impedance, low power op amp 172. Output signal 174 is used as feedback to the inverting input of op amp 172 through resistor 176 and capacitor 178 which are connected in parallel. The inverting input of op amp 172 is also connected to reference voltage 144 through a resistor 180.

Amplifier 168 is connected to a three-stage sensor filter 182 with an output conductor 184 which carries output signal 174. The electrical activity or voltage signal 160 is amplified by each of the stages 168 and 182 while undesired signals, such as those 60 Hz and above, are attenuated by each of the stages. Three-stage sensor filter has three stages 2206a, 2206b and 2206c each having the same design to provide a bandpass filter function which allows signals between 1.2 and 12 Hz to pass with a gain of 5 while attenuating signal lower and higher than these frequencies. The bandpass filter function allows signals in the Alpha and Theta bands to pass while attenuating noise such as 60 Hz and harmonics of the 60 Hz. The three stage sensor filter 182 removes offsets in the signal that are due to biases and offsets in the parts. Each of the three stages is connected to source voltage 146 and reference voltage 144. Each of the three stages generates an output signal 186a, 186b and 186c on an output conductor 188a, 186b and 188c, respectively.

Figure 21:
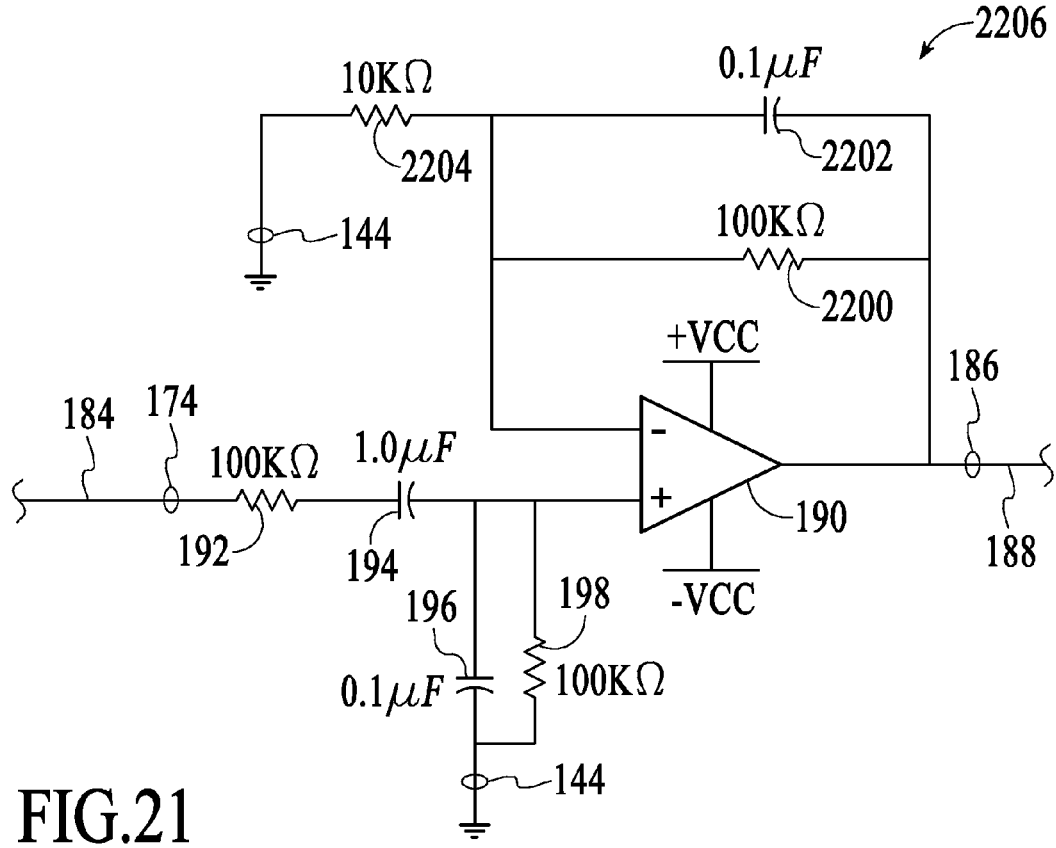
FIG. 21 is a circuit diagram of a filter stage of the sensor headset, under an embodiment.
Figure 23:
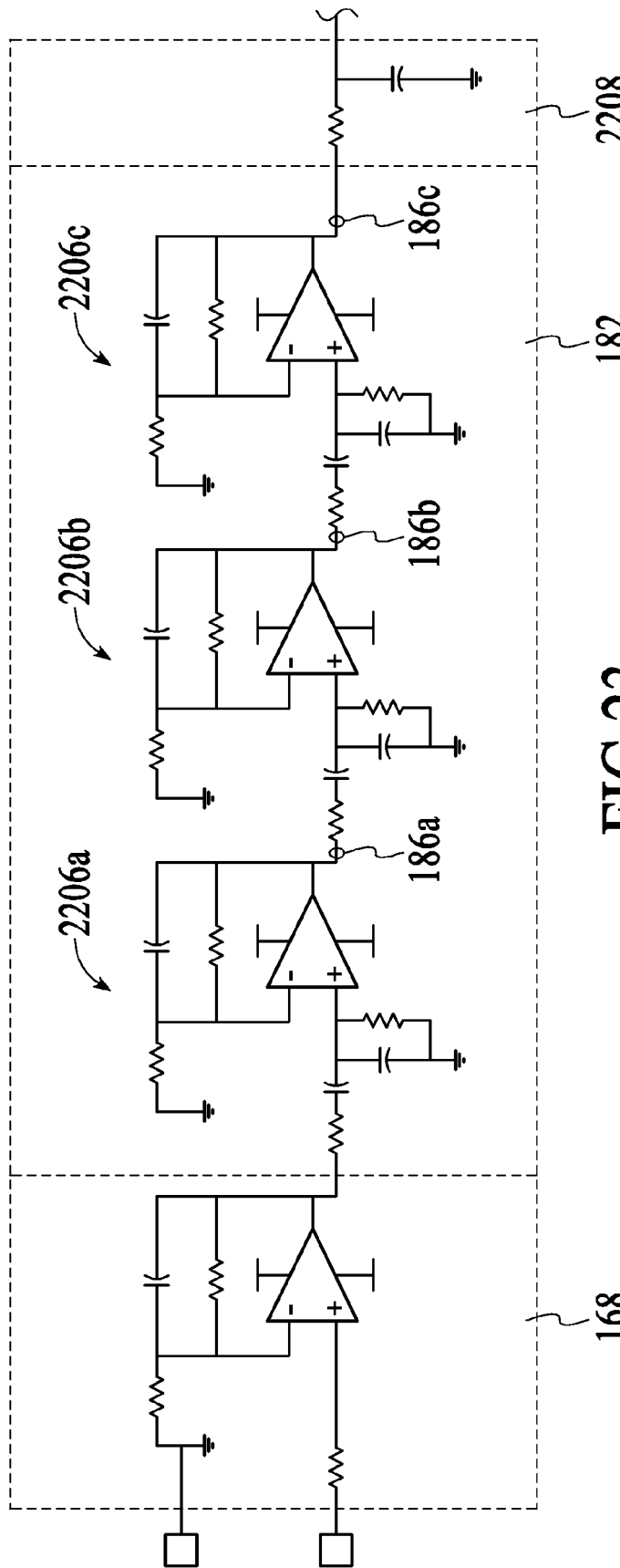
FIG. 23 is a circuit diagram of the amplifier, three filter stages and the RC filter of the sensor headset, under an embodiment.

In the first stage 2206a, FIGS. 21 and 23, of three-stage sensor filter 182, output signal 174 is supplied to a non-inverting input of a first stage op-amp 190a through a resistor 192a and capacitor 194a. A capacitor 196a and another resistor 198a are connected between the non-inverting input and reference voltage 144. Feedback of the output signal 186a from the first stage is connected to the inverting input of op amp 190a through a resistor 2200a and a capacitor 2202a which are connected in parallel. The inverting input of op amp 190a is also connected to reference voltage 144 through resistor 2204a.

Second and third stages 2206b and 2206c, respectively, are arranged in series with first stage 2206a. First stage output signal 186a is supplied to second stage 2206b through resistor 192b and capacitor 194b to the non-inverting input of op-amp 190b. Second stage output signal 186b is supplied to third stage 2206c through resistor 192c and capacitor 194c. Resistor 198b and capacitor 196b are connected between the non-inverting input of op-amp 190b and reference potential 144, and resistor 198c and capacitor 196c are connected between the non-inverting input of op-amp 190c and reference potential 144. Feedback from output conductor 188*b* to the inverting input of op-amp 190*b* is through resistor 2200*b* and capacitor 2202*b* and the inverting input of op-amp 190*b* is also connected to reference potential 144 with resistor 204*b*. Feedback from output conductor 188*c* to the inverting input of op-amp 190*c* is through resistor 2200*c* and capacitor 2202*c* and the inverting input of op-amp 190*c* is also connected to reference potential 144 with resistor 2204*c*.

Figure 22:
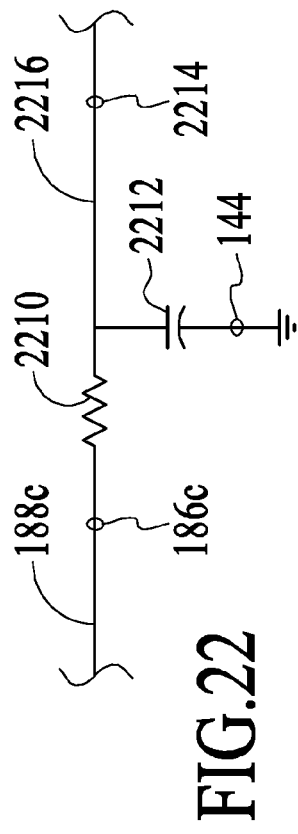
FIG. 22 is a circuit diagram of a resistor-capacitor RC filter of the sensor headset, under an embodiment.

Three stage sensor filter 182 is connected to an RC filter 2208, FIGS. 22 and 23, with the output conductor 188*c* which carries the output signal 186*c* from third stage 2206*c* of three stage sensor filter 182, FIG. 19. RC filter 2208 includes a resistor 2210 which is connected in series to an output conductor 2216, and a capacitor 2212 which connects between reference potential 144 and output conductor 2216. RC filter serves as a low pass filter to further filter out frequencies above 12 Hz. RC filter 2208 produces a filter signal 2214 on output conductor 2216. RC filter 2208 is connected to an analog to digital (A/D) converter 2218, FIG. 19.

The A/D converter 118 converts the analog filter signal 2214 from the RC filter to a digital signal 220 by sampling the analog filter signal 2214 at a sample rate that is a multiple of 60 Hz. In the present example the sample rate is 9600 samples per second. Digital signal 220 is carried to a digital processor 224 on an output conductor 222.

Figure 24:
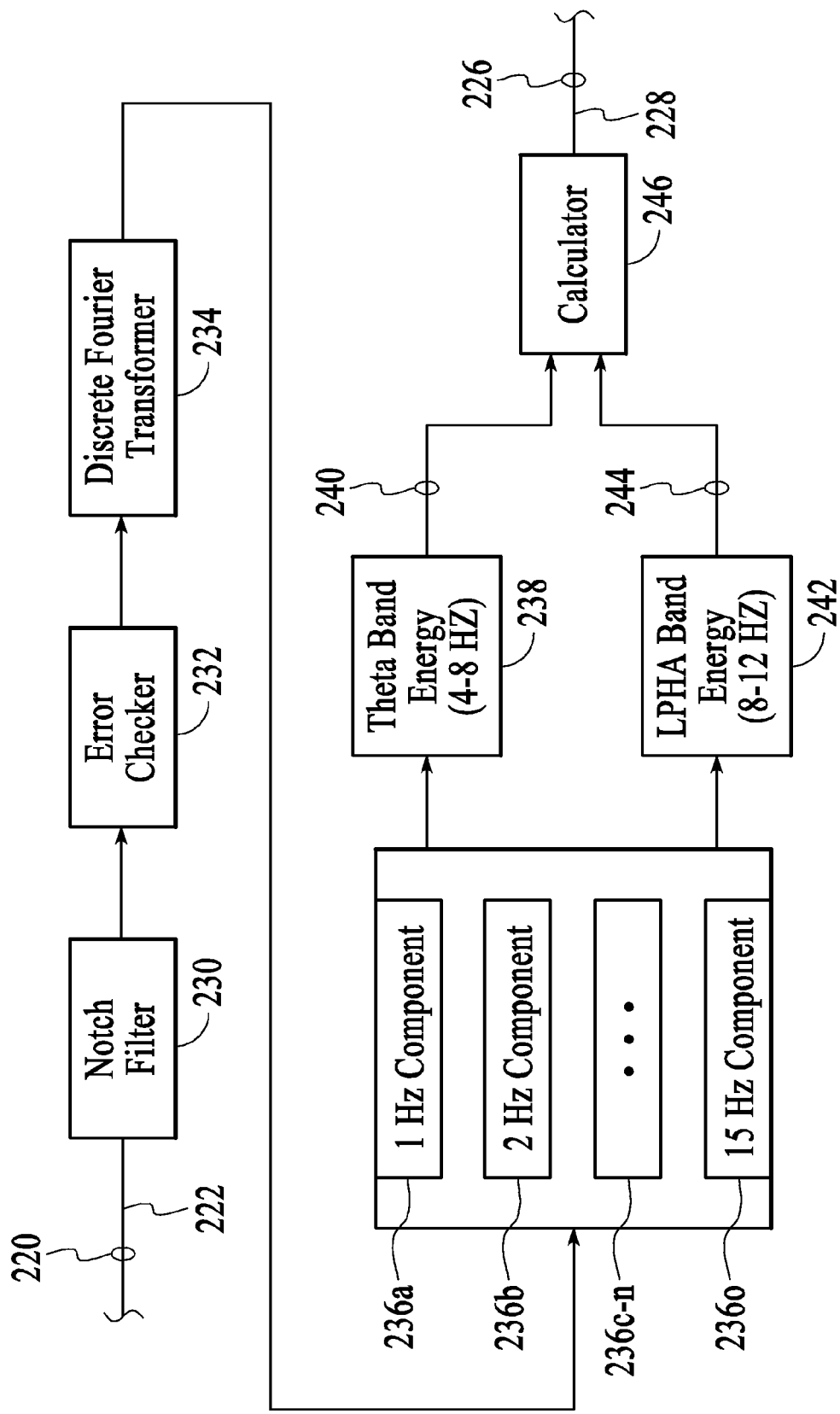
FIG. 24 is a block diagram of a digital processor of the sensor headset, under an embodiment.

Digital processor 224, FIGS. 19 and 24 provides additional gain, removal of 60 Hz noise, and attenuation of high frequency data. Digital processor 224 many be implemented in software operating on a computing device. Digital processor 224 includes a notch filter 230, FIG. 24 which sums 160 data points of digital signal 220 at a time to produce a 60 Hz data stream that is free from any information at 60 Hz. Following notch filter 230 is an error checker 232. Error checker 232 removes data points that are out of range from the 60 Hz data stream. These out of range data points are either erroneous data or they are cause by some external source other than brain activity.

After error checker 232, digital processor 224 transforms the data stream using a discreet Fourier transformer 234. While prior EEG systems use band pass filters to select out the Alpha and Theta frequencies, among others, these filters are limited to processing and selecting out continuous periodic functions. By using a Fourier transform, digital processor 224 is able to identify randomly spaced events. Each event has energy in all frequencies, but shorter events will have more energy in higher frequencies and longer events will have more energy in lower frequencies. By looking at the difference between the energy in Alpha and Theta frequencies, the system is able to identify the predominance of longer or shorter events. The difference is then scaled by the total energy in the bands. This causes the output to be based on the type of energy and removes anything tied to amount of energy.

The Fourier transformer 234 creates a spectrum signal that separates the energy into bins 236*a* to 236*o* which each have a different width of frequency. In one example, the spectrum signal has 30 samples and separates the energy spectrum into 2 Hz wide bins; in another example, the spectrum signal has 60 samples and separates the bins into 1 Hz wide bins. Bins 236 are added to create energy signals in certain bands. In the present example, bins 236 between 4 and 8 Hz are passed to a summer 238 which sums these bins to create a Theta band energy signal 240; and bins between 8 and 12 Hz are passed to a summer 242 which sums these bins to create an Alpha band energy signal 244.

In the present example, the Alpha and Theta band energy signals 240 and 244 passed to a calculator 246 which calculates (Theta−Alpha)/Theta+Alpha) and produces an output signal 226 on a conductor 228 as a result.

Output signal 226, FIG. 19, is passed to wireless transmitter 46 which transmits the output signal 226 to wireless receiver 48 over wireless link 50. In the present example, output signal 226 is the signal of interest which is passed to computer 54 through port 52 and which is used by the computer to produce the PTES for display in meter 56.

Computer 54 may provide additional processing of output signal 226 in some instances. In the example using the Release Technique, the computer 54 manipulates output signal 226 to determine relative amounts of Alpha and Theta band signals in the output signal to determine levels of release experienced by user 34.

A sensor device utilizing the above described principles and feature can be used for determining electrical activity in other tissue of the user in addition to the brain tissue just described, such as electrical activity in muscle and heart tissue. In these instances, the sensor electrode is positioned on the skin at the point where the electrical activity is to be measured and the reference electrode and electronics module are positioned nearby with the reference electrode attached to a point near the sensor electrode. The electronics module, in these instances, includes amplification and filtering to isolate the frequencies of the muscle or heart electrical activity while filtering out other frequencies.

There are many practical applications of physiological data that could be enabled with a non-intrusive sensing device (sensor) that allows a test subject to participate in normal activities with a minimal amount of interference from the device, as described above. The data quality of this device need not be as stringent as a medical device as long as the device measures data accurately enough to satisfy the needs of parties interested in such data, making it possible to greatly simplify the use and collection of physiological data when one is not concerned about treating any disease or illness. There are various types of non-intrusive sensors that are in existence. For a non-limiting example, modern three axis accelerometer can exist on a single silicon chip and can be included in many modern devices. The accelerometer allows for tracking and recording the movement of whatever subject the accelerometer is attached to. For another non-limiting example, temperature sensors have also existed for a long time in many forms, with either wired or wireless connections. All of these sensors can provide useful feedback about a test subject's responses to stimuli, but thus far, no single device has been able to incorporate all of them seamlessly. Attaching each of these sensors to an individual separately is timing consuming and difficult, requiring a trained professional to insure correct installation and use. In addition, each newly-added sensor introduces an extra level of complexity, user confusion, and bulk to the testing instrumentation.

As described above an integrated headset is introduced, which integrates a plurality of sensors into one single piece and can be placed on a person's head for measurement of his/her physiological data. Such integrated headset is adaptive, which allows adjustability to fit the specific shape and/or size of the person's head. The integrated headset minimizes data artifacts arising from at least one or more of: electronic interference among the plurality of sensors, poor contacts between the plurality of sensors and head movement of the person. In addition, combining several types of physiological sensors into one piece renders the measured physiological data more robust and accurate as a whole.

The integrated headset of an embodiment integrates a plurality of sensors into one single piece and can be placed on a person's head for measurement of his/her physiological data. Such integrated headset is easy to use, which measures the physiological data from the person accurately without requiring any conductive gel or skin preparation at contact points between the plurality of sensors and the person's skin. In addition, combining several types of physiological sensors into one piece renders the measured physiological data more robust and accurate as a whole.

The integrated headset of an embodiment integrates a plurality of sensors into one single piece and can be placed on a person's head for measurement of his/her physiological data. Such integrated headset is non-intrusive, which allows the person wearing the headset to freely conduct a plurality of functions without any substantial interference from the physiological sensors integrated in the headset. In addition, combining several types of physiological sensors into one piece renders the measured physiological data more robust and accurate as a whole.

Having a single device that incorporates numerous sensors also provides a huge value for advertisers, media producers, educators and many other parties interested in physiological data. These parties desire to understand the reactions and responses people have to their particular stimulus in order to tailor their information or media to better suit the needs of end users and/or to increase the effectiveness of the media. By sensing these exact changes instead of using focus groups, surveys, knobs or other easily biased measures of response, the integrated sensor improves both the data that is measured and recorded and the granularity of such data, as physiological data can be recorded by a computer program/device many times per second. The physiological data can also be mathematically combined from the plurality of sensors to create specific outputs that corresponds to a person's mental and emotional state (response).

As described above, FIG. 3 shows another example embodiment of the sensor headset described herein. Although the diagrams depict components as functionally separate, such depiction is merely for illustrative purposes. It will be apparent to those skilled in the art that the components portrayed in this figure can be arbitrarily combined or divided into separate software, firmware and/or hardware components. Furthermore, it will also be apparent to those skilled in the art that such components, regardless of how they are combined or divided, can execute on the same computing device or multiple computing devices, and wherein the multiple computing devices can be connected by one or more networks.

Referring to FIG. 3, the integrated headset may include at least one or more of the following components: a processing unit 301, which can be but is not limited to a microprocessor, functions as a signal collection, processing and transmitting circuitry that collects, digitizes, and processes the physiological data measured from a person who wears the headset and transmits such data to a separate/remote location. A motion detection unit 302, which can be but is not limited to a three axis accelerometer, senses movement of the head of the person. A stabilizing component 303, which can be but is not limited to a silicon stabilization strip, stabilizes and connects the various components of the headset together. Such stabilizing component provides adhesion to the head by surface tension created by a sweat layer under the strip to stabilize the headset for more robust sensing through stabilization of the headset that minimizes responses to head movement of the person.

The headset includes a set of EEG electrodes, which can be but is not limited to a right EEG electrode 304 and a left EEG electrode 306 positioned symmetrically about the centerline of the forehead of the person, can be utilized to sense/measure EEG signals from the person. The electrodes may also have another contact on one ear of the person for a ground reference. These EEG electrodes can be prefrontal dry electrodes that do not need conductive gel or skin preparation to be used, where contacts are needed between the electrodes and the skin of the person but without excessive pressure applied.

The headset includes a heart rate sensor 305, which is a robust blood volume pulse sensor that can measure the person's heart rate and the sensor can be positioned directly in the center of the forehead of the person between the set of EEG electrodes. Power handling and transmission circuitry 307, which includes a rechargeable or replaceable battery module, provides operating power to the components of the headset and can be located over an ear of a wearer. An adjustable strap 308 positioned in the rear of the person's head can be used to adjust the headset to a comfortable tension setting for the shape and size of the person so that the pressure applied to the plurality of sensors is adequate for robust sensing without causing discomfort. Note that although motion detection unit, EEG electrodes, and heart rate sensor are used here as non-limiting examples of sensors, other types of sensors can also be integrated into the headset, wherein these types of sensors can be but are not limited to, electroencephalograms, blood oxygen sensors, galvanometers, electromygraphs, skin temperature sensors, breathing sensors, and any other types of physiological sensors.

In some embodiments, the integrated headset can be turned on with a push button and the test subject's physiological data can be measured and recorded instantly. Data transmission from the headset can be handled wirelessly through a computer interface to which the headset links. No skin preparation or conductive gels are needed on the tester to obtain an accurate measurement, and the headset can be removed from the tester easily and be instantly used by another person. No degradation of the headset occurs during use and the headset can be reused thousands of times, allowing measurement to be done on many participants in a short amount of time and at low cost.

In some embodiments, the accelerometer 302 can be incorporated into an electronic package in a manner that allows its three axes to align closely to the regularly accepted axes directions in a three-dimensional space. Such requirement is necessary for the accelerometer to output data that can be easily interpreted without the need for complex mathematical operations to normalize the data to fit the standard three-axis system. Other sensors such as temperature sensors have less stringent location requirements and are more robust, which can be placed at various locations on the headset.

The physiological signals emanating from a human being are extremely small, especially in comparison to the general environmental background noise that is always present. This presents a challenge for creating an integrated headset that is very stable and minimizes data artifacts, wherein the artifacts may arise from at least one or more of: electronic interference, poor contact points, head movement that creates static electricity.

One of the major problems in recording human physiological signals is the issue of electrical interference, which may come from either external environmental sources or the various sensors that are incorporated into the single headset, or both. Combining multiple sensors into a single integrated headset may cause electrical interference to leak from one component (sensor) over into another due to the very weak signals that are being detected. For a non-limiting example, an EEG electrode is very sensitive to interference and signals from other sensors can create artifacts in the EEG reading.

In some embodiments, data transmission from the headset can be handled wirelessly through a computer interface that the headset links to. Since wireless communication happens at high frequencies, the typical 50/60 Hz electrical noise that may, for a non-limiting example, be coupled to a signal wire and interfere with the measured data transferred by the wire can be minimized.

In some embodiments, power levels of one or more of the sensors integrated in the integrated headset may be tuned as low as possible to minimize the electrical interference. In addition, specific distance between signal-carrying wires of the sensors can also be set and enforced to reduce the (electronic) crosstalk between the wires.

In some embodiments, with reference to FIG. 3, the power handling and transmission circuitry 307 of the integrated headset can be separated from the signal collection and processing circuitry 301. Being a wireless device, the integrated headset uses a battery and the noise generated by the battery may ruin the measurement as the battery noise is far larger than the electrical signals being measured. By physically separating the circuits and only delivering power by means of minimum number of wires needed, the integrated headset can cut down electrical interference significantly.

In some embodiments, the power and signal processing circuitry can be placed over opposite ears of the tester, respectively. A flat cable can be used to transmit the power from the battery module 307 over the left ear to the signal processing circuitry 301 over the right ear. The data from the heart rate sensor 305 can also be carried using a similar flat cable, which allows greater control over wire placement and restricts the wires from moving around during use as in the case with conventional stranded wires. In addition, the EEG electrodes 304 and 306 can be wired using conventional stranded copper wire to carry the signal to the signal processing circuit 301. The wires from the EEG electrodes can be placed at the extents of the plastic housing of the headset at least 0.1" away from the heart sensor cable, which helps to reduce the possible electrical interference to an acceptable level.

In some embodiments, the plurality of sensors in the integrated headset can have different types of contacts with the test subject. Here, the contacts can be made of an electrically conductive material, which for non-limiting examples can be but are not limited to, nickel-coated copper or a conductive plastic material. The integrated headset can minimize the noise entering the measuring contact points of the sensors by adopting dry EEG electrodes that work at acceptable noise levels without the use of conductive gels or skin abrasion.

In some embodiments, a non-adhesive or rubber-like substance can be applied against the skin to create a sweat layer between the two that increases the friction between the skin and the headset, normally in less than a minute. This sweating liquid provides better conductivity between the skin and the contacts of the plurality of sensors. In addition, this liquid creates a surface tension that increases the friction and holding strength between the skin and the headset, creating a natural stabilizer for the headset without the use of gels, adhesives or extraneous attachment mechanisms. The holding force increases significantly only in parallel to the plane of the skin, keeping the headset from sliding around on the skin, which is the major problem area in noise generation. Such non-adhesive substance does not, however, significantly increase the holding strength perpendicular to the plane of the skin, so it is not uncomfortable to remove the headset from the tester as it would be the case if an adhesive were applied to hold the headset in place as with many medical sensing devices.

In some embodiments, the headset is operable to promote approximately even pressure distribution at front and back of the person's head to improve comfort and/or produce better signals of the measured physiological data. A foam pad can be used to create a large contact area around the sensors (such as the heart rate sensor 305) and to create a consistent height for the inside of the headset. This result is increased user comfort since the foam reduces pressure at contact points that would otherwise exist at the raised EEG contacts. It also helps to create the correct amount of pressure at the contact points on the forehead.

Human heads exist in many different shapes and sizes and any headset that is easy to use must accommodate various shapes and sizes of the testers' heads. It is impractical, however, to create numerous different shapes and sizes for the integrated headset as it would require a trained fitter to choose the correct one for each different tester. In addition, the fitting process would be so time-consuming that it defeats the main goal of making the headset easy to use.

In some embodiments, the integrated headset is designed to be adaptive, flexible and compliant, which can automatically adjust to different head shapes and sizes of tester's heads. Since poor contact or movement relative to the skin has the potential to generate a greater amount of noise than the headset can handle, the headset is designed in such a way to minimize movement and to create compliance and fitting to varying head shapes and sizes. The tester should be able to simply put on the headset, tighten the adjustable strap 308 that allows the headset to be worn comfortably, and be ready to work.

In some embodiments, the compliance in the adjustable strap 308 of the headset must be tuned so that it is not overly soft and can support weight of the headset; otherwise the headset may result in a situation where the noise from the moving headset would override the measured signal from the sensors. On the other hand, the compliance cannot be so little that it would necessitate over-tightening of the headset, because the human head does not cope well with high amount of pressure being applied directly to the head, which may cause headaches and a sense of claustrophobia on the test subject who wears a headset that is too tight.

In some embodiments, the headset itself surrounds and holds these components on the brow of the head and passes over both ears and around the back of the head. The body of the headset is made of a thin, lightweight material such as plastic or fabric that allows flexing for the headset to match different head shapes but is stiff in the minor plane to not allow twisting, which may cause the electrodes to move and create noise.

In some embodiments, the EEG electrodes and the heart rate sensor both need contacts with the skin of the tester's head that are near the center of the forehead and do not slide around. However, too much contact pressure may create an uncomfortable situation for the tester and is thus not acceptable. Therefore, the integrated headset applies consistent pressure at multiple contact points on different head shapes and sizes of testers, wherein such pressure is both compliant enough to match different head geometries and to create stickiness to the skin and help to stabilize the headset. Here, the headset is operable to achieve such pre-defined pressure by using various thicknesses, materials, and/or geometries at the desired locations of the contact points.

In some embodiments, one or more processing units (301) that deal with data collection, signal processing, and information transmission are located above the ears to give the unit, the largest component on the headset, a stable base, as allowing the units to hang unsupported would cause them to oscillate with any type of head movement. A silicon stabilization strip 303 allows for more robust sensing through stabilization of the headset by minimizing movement.

In some embodiments, electronic wiring and/or circuitry (electronic components) of the headset can be placed inside the plastic housing of the headset with another layer of 0.015" thick ABS plastics in between the electronic components and the skin to provide protection to the components and/or an aesthetic cover for the headset. The inside plastic can be retained by a series of clips and tabs to allow the plastic to slide relative to the outer housing, which precludes the creation of a composite beam if the two were attached together using glue or any other rigid attachment mechanism, as a composite beam is much stiffer than two independent pieces of material and would thus decrease the compliance of the headset.

In some embodiments, the adjustable rubber strip 308 can be attached to the inside plastic at the very bottom along the entire length of the headset, which creates a large surface area over which an increased friction force may keep the headset from moving. Having consistent and repeatable contact is crucial to the quality of the EEG data and friction increase from the rubber strip facilitates that process. The strip also provides some cushioning which increases user comfort.

Embodiments described herein include a system comprising: a plurality of headsets, wherein each headset is worn by a viewer of a plurality of viewers located at a venue, each headset including at least one sensor and a transmitter, wherein the plurality of viewers is watching a media instance, wherein each headset receives physiological data from the corresponding viewer; a signal collection device located at the venue, the signal collection device receiving the physiological data transmitted by the plurality of headsets via a wireless coupling; and a processing module that receives the physiological data from the signal collection device, wherein the processing module derives from the physiological data a plurality of physiological responses of the plurality of viewers to the media instance.

The processing module of an embodiment synchronizes the physiological data from the plurality of viewers.

The processing module of an embodiment synchronizes the media instance and the physiological data from the plurality of viewers.

The signal collection device of an embodiment synchronizes the physiological data from the plurality of viewers.

The signal collection device of an embodiment synchronizes the media instance and the physiological data from the plurality of viewers.

The signal collection device of an embodiment removes data from the corresponding physiological data for a time period during which a viewer of the plurality of viewers is not paying attention to the media instance before transferring the data to the processing module.

The processing module of an embodiment interpolates physiological data from the time period when a viewer of the plurality of viewers is paying attention to cover the data that has been removed.

The physiological data of an embodiment is at least one of heart rate, brain waves, EEG signals, blink rate, breathing, motion, muscle movement, galvanic skin response, and a response correlated with change in emotion.

The processing module of an embodiment removes artifacts of the physiological data.

The anomaly of an embodiment is detected using at least one of heart rate, brain waves, EEG signals, blink rate, breathing, motion, muscle movement, and galvanic skin response.

The physiological data of an embodiment is heart rate.

The physiological data of an embodiment is brain waves.

The physiological data of an embodiment is EEG signals.

The physiological data of an embodiment is blink rate.

The physiological data of an embodiment is breathing.

The physiological data of an embodiment is motion.

The physiological data of an embodiment is muscle movement.

The physiological data of an embodiment is galvanic skin response.

The physiological data of an embodiment is a response correlated with change in emotion.

The at least one sensor of an embodiment includes a physiological sensor.

The at least one sensor of an embodiment includes an electroencephalogram.

The at least one sensor of an embodiment includes an accelerometer.

The at least one sensor of an embodiment includes a blood oxygen sensor.

The at least one sensor of an embodiment includes a galvanometer.

The at least one sensor of an embodiment includes a electromygraph.

The headset of an embodiment includes at least one dry EEG electrode.

The headset of an embodiment includes at least one heart rate sensor.

The headset of an embodiment includes at least one accelerometer.

The headset of an embodiment includes at least one processor.

The headset of an embodiment includes at least one wireless communication device.

The plurality of physiological responses of an embodiment includes liking.

The plurality of physiological responses of an embodiment includes thought.

The plurality of physiological responses of an embodiment includes adrenaline.

The plurality of physiological responses of an embodiment includes engagement.

The plurality of physiological responses of an embodiment includes immersion in the media instance.

The system of an embodiment comprises a rating module that rates the media instance based on the plurality of physiological responses from the plurality of viewers.

The system of an embodiment comprises a reaction database that stores at least one of the physiological data, the plurality of physiological responses, and analysis results of the physiological responses.

The reaction database of an embodiment stores at least one of data of the media instance, and results of surveys presented to the plurality of viewers and corresponding to the media instance.

The media instance of an embodiment is at least one of a television program, an advertisement, a movie, printed media, a website, a computer application, a video game, and a live performance.

The media instance of an embodiment is representative of a product.

The media instance of an embodiment is at least one of product information and product content.

The plurality of viewers of an embodiment includes a plurality of sets of viewers, wherein a first set of viewers is located in a first region of the venue and a second set of viewers is located in a second region of the venue, wherein the first region is different from the second region.

The system of an embodiment comprises a tutorial, wherein a computer coupled to the processing module automatically receives and installs the tutorial, wherein the tutorial comprises information relating to watching of the media instance and data collection during the watching.

The tutorial of an embodiment automatically instructs the plurality of viewers in use of the headsets.

The tutorial of an embodiment automatically determines a data quality of the physiological data received from the plurality of headsets.

Embodiments described herein include a system comprising: a plurality of headsets, wherein each headset is worn by a viewer of a plurality of viewers located at a venue, each headset including at least one sensor and a transmitter, wherein the plurality of viewers is watching a media instance, wherein each headset receives physiological data from the corresponding viewer; a signal collection device located at the venue, the signal collection device receiving the physiological data transmitted by the plurality of headsets via a wireless coupling, wherein the signal collection device generates aggregated data by aggregating the physiological data of the plurality of viewers; and a processing module that receives the physiological data from the signal collection device, wherein the processing module derives from the physiological data a plurality of physiological responses of the plurality of viewers to the media instance.

Embodiments described herein include a system comprising: a plurality of headsets, wherein each headset is worn by a viewer of a plurality of viewers located at a venue, each headset including at least one sensor and a transmitter, wherein the plurality of viewers is watching a media instance, wherein each headset receives physiological data from the corresponding viewer; a signal collection device coupled to the plurality of headsets, the signal collection device receiving the physiological data transmitted by the plurality of headsets via a plurality of wireless couplings, wherein the signal collection device controls data quality of the physiological data; and a processing module that receives the physiological data from the signal collection device, wherein the processing module generates aggregated data by aggregating the physiological data of the plurality of viewers, wherein the processing module provides controlled access to the aggregated data and the media instance.

Embodiments described herein include a system comprising: a plurality of headsets, wherein each headset is worn by a viewer of a plurality of viewers located at a venue, each headset including at least one sensor and a transmitter, wherein the plurality of viewers is watching a media instance, wherein each headset receives physiological data from the corresponding viewer; a signal collection device located at the venue, the signal collection device receiving the physiological data transmitted by the plurality of headsets and generating aggregated data by aggregating the data from the plurality of viewers and synchronizing the physiological data received from each viewer with the physiological data received from every other viewer; and a processing module that receives the physiological data from the signal collection device, wherein the processing module generates synchronized data by synchronizing the aggregated data with the media instance.

Embodiments described herein include a system comprising: a plurality of headsets, wherein each headset is worn by a viewer of a plurality of viewers located at a venue, each headset including at least one sensor and a transmitter, wherein the plurality of viewers is watching a media instance, wherein each headset receives physiological data from the corresponding viewer; a signal collection device coupled to the plurality of headsets; and a processing module that receives the physiological data from the signal collection device, wherein the processing module generates synchronized data by synchronizing the physiological data from the plurality of viewers, and synchronizing the synchronized data with the media instance.

Embodiments described herein include a system comprising: a plurality of headsets, wherein each headset is worn by a viewer of a plurality of viewers located at a venue, each headset including at least one sensor and a transmitter, wherein the plurality of viewers is watching a media instance, wherein each headset receives physiological data from the corresponding viewer; a signal collection device located at the venue and receiving the physiological data transmitted by the plurality of headsets via a wireless coupling, wherein the signal collection device removes data from the corresponding physiological data for a time period during which the corresponding viewer is not paying attention to the media instance; and a processing module that receives the physiological data from the signal collection device, wherein the processing module generates synchronized data by synchronizing the physiological data from the plurality of viewers with the media instance.

Embodiments described herein include a system comprising: a plurality of headsets, wherein each headset is worn by a viewer of a plurality of viewers located at a venue, each headset including at least one sensor and a transmitter, wherein the plurality of viewers is watching a media instance, wherein each headset receives physiological data from the corresponding viewer; a signal collection device located at the venue and receiving the physiological data transmitted by the plurality of headsets via a wireless coupling; and a processing module that receives the physiological data from the signal collection device, wherein the processing module removes data from the corresponding physiological data for a time period during which the corresponding viewer is not paying attention to the media instance, wherein the processing module generates synchronized data by synchronizing the physiological data from the plurality of viewers with the media instance.

Embodiments described herein include a method comprising: receiving physiological data from a plurality of viewers via a plurality of headsets worn by each of the plurality of viewers, the plurality of viewers watching a media instance; receiving the physiological data from the plurality of headsets at a signal collection device, wherein the signal collection device receives the physiological data transmitted by the plurality of headsets; and receiving the physiological data from the signal collection device at a processing module and deriving from the physiological data a plurality of physiological responses of the plurality of viewers to the media instance.

The method of an embodiment comprises synchronizing the physiological data from the plurality of viewers.

The method of an embodiment comprises synchronizing the media instance and the physiological data from the plurality of viewers.

The method of an embodiment comprises removing data from the corresponding physiological data for a time period during which the corresponding viewer is not paying attention to the media instance.

The method of an embodiment comprises interpolating physiological data from the time period when the viewer is paying attention to cover the data that has been removed.

The method of an embodiment comprises detecting an anomaly in the physiological data of a viewer using at least one of heart rate, brain waves, EEG signals, blink rate, breathing, motion, muscle movement, and galvanic skin response.

The method of an embodiment comprises removing artifacts of the physiological data.

The method of an embodiment comprises rating the media instance based on the plurality of physiological responses from the plurality of viewers.

The method of an embodiment comprises storing at least one of the physiological data, the plurality of physiological responses, and analysis results of the physiological responses.

The method of an embodiment comprises storing at least one of data of the media instance, and results of surveys presented to the plurality of viewers and corresponding to the media instance.

The physiological data of an embodiment is at least one of heart rate, brain waves, electroencephalogram (EEG) signals, blink rate, breathing, motion, muscle movement, galvanic skin response, and a response correlated with change in emotion.

Receiving physiological data of an embodiment comprises sensing the physiological data using at least one of a physiological sensor, an electroencephalogram (EEG), an accelerometer, a blood oxygen sensor, a galvanometer, an electromygraph, a dry EEG electrode, and a heart rate sensor.

The plurality of physiological responses of an embodiment includes at least one of liking, thought, adrenaline, engagement, and immersion in the media instance.

The media instance of an embodiment is at least one of a television program, an advertisement, a movie, printed media, a website, computer application, a video game, live performance, product information, and product content.

The method of an embodiment comprises automatically providing a tutorial to the plurality of viewers via a computer, wherein the computer automatically receives and installs the tutorial, wherein the tutorial comprises information relating to watching of the media instance and data collection during the watching.

The method of an embodiment comprises automatically instructing the plurality of viewers in use of the headsets.

The method of an embodiment comprises automatically determining a data quality of the physiological data.

The systems and methods described herein include and/or run under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, mobile telephones, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc. The processor and memory can be monolithically integrated onto a single chip, distributed among a number of chips or components, and/or provided by some combination of algorithms. The methods described herein can be implemented in one or more of software algorithm(s), programs, firmware, hardware, components, circuitry, in any combination.

Components of the systems and methods described herein can be located together or in separate locations. Communication paths couple the components and include any medium for communicating or transferring files among the components. The communication paths include wireless connections, wired connections, and hybrid wireless/wired connections. The communication paths also include couplings or connections to networks including local area networks (LANs), metropolitan area networks (MANs), WiMax networks, wide area networks (WANs), proprietary networks, interoffice or backend networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

One embodiment may be implemented using a conventional general purpose or a specialized digital computer or microprocessor(s) programmed according to the teachings of the present disclosure, as will be apparent to those skilled in the computer art. Appropriate software coding can readily be prepared by skilled programmers based on the teachings of the present disclosure, as will be apparent to those skilled in the software art. The invention may also be implemented by the preparation of integrated circuits or by interconnecting an appropriate network of conventional component circuits, as will be readily apparent to those skilled in the art.

One embodiment includes a computer program product which is a machine readable medium (media) having instructions stored thereon/in which can be used to program one or more computing devices to perform any of the features presented herein. The machine readable medium can include, but is not limited to, one or more types of disks including floppy disks, optical discs, DVD, CD-ROMs, micro drive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data. Stored on any one of the computer readable medium (media), the present invention includes software for controlling both the hardware of the general purpose/specialized computer or microprocessor, and for enabling the computer or microprocessor to interact with a human viewer or other mechanism utilizing the results of the present invention. Such software may include, but is not limited to, device drivers, operating systems, execution environments/containers, and applications.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the systems and methods described herein is not intended to be exhaustive or to limit the systems and methods described to the precise form disclosed. While specific embodiments of, and examples for, the systems and methods described herein are described herein for illustrative purposes, various equivalent modifications are possible within the scope of other systems and methods, as those skilled in the relevant art will recognize. The teachings of the systems and methods described herein provided herein can be applied to other processing systems and methods, not only for the systems and methods described above.

The elements and acts of the various embodiments described above can be combined to provide further embodiments. These and other changes can be made to the systems and methods described herein in light of the above detailed description.

In general, in the following claims, the terms used should not be construed to limit the embodiments to the specific embodiments disclosed in the specification and the claims, but should be construed to include all systems that operate under the claims. Accordingly, the embodiments are not limited by the disclosure, but instead the scope of the embodiments is to be determined entirely by the claims.

While certain aspects of the embodiments are presented below in certain claim forms, the inventors contemplate the various aspects of the embodiments in any number of claim forms. Accordingly, the inventors reserve the right to add additional claims after filing the application to pursue such additional claim forms for other aspects of the embodiments described herein.

What is claimed is:

1. A method comprising:
   a first processor analyzing first physiological data gathered by a first sensor coupled to a first headset worn by a first subject when the first subject is exposed to media, the first headset including the first processor;
   the first processor generating first data indicative of an emotional response of the first subject based on the first physiological data;
   a first transmitter associated with the first headset transmitting the first data indicative of the emotional response to a second headset worn by a second subject, the second headset including a transceiver to receive the first data;
   a second processor analyzing second physiological data gathered by a second sensor coupled to the second headset worn by the second subject when the second subject is exposed to the media, the second headset carrying the second processor;
   the second processor generating second data indicative of an emotional response of the second subject based on the second physiological data; and
   the second processor synchronizing the first data with the second data indicative of the emotional response of the second subject for the media to generate synchronized response data; and
   a second transmitter associated with the second headset transmitting the synchronized response data to a central unit.

2. The method as defined in claim 1, wherein the first headset further includes:
   signal processing circuitry to process the first physiological data, the signal processing circuitry disposed at a first end of the first headset above a first ear of the first subject when the first headset is worn by the first subject; and
   power circuitry to power the first headset, the power circuitry disposed at a second end of the first headset, opposite the first end and above a second ear of the first subject when the first headset is worn by the first subject.

3. The method as defined in claim 1, the first processor providing a tutorial to the subject to inform the first subject how to fit and wear the first headset.

4. The method as defined in claim 1, the first processor analyzing a heart rate of the first subject; and
   determining if the heart rate is below a threshold.

5. The method as defined in claim 4, the first processor disqualifying the first subject if the heart rate is not below the threshold.

6. The method as defined in claim 1, the first processor analyzing an energy of an electroencephalographic signal of the first subject; and
   determining a mental state based on the energy.

7. The method as defined in claim 6, the first processor disqualifying the first subject based on the mental state.

8. The method as defined in claim 1, the first processor analyzing a blink rate of the first subject; and
   determining if the blink rate is below a threshold.

9. The method as defined in claim 8, the first processor disqualifying the first subject if the blink rate is not below the threshold.

10. The method as defined in claim 1, the first processor testing a quality of a connection of the first sensor.

11. The method as defined in claim 1, the first processor transmitting the first physiological data to a set-top box.

12. The method as defined in claim 1, the first processor removing data from the first physiological data for a time period during which the first subject was not paying attention to the media.

13. The method as defined in claim 12, the first processor interpolating third physiological data based on the first physiological data from a time period when the first subject is paying attention to the media to replace the removed data.

14. The method as defined in claim 1, the first processor calculating a score based on the first physiological data, the score representative of an effectiveness of the media.

15. The method as defined in claim 1, wherein the first subject is located at a first venue and the second subject is located at a second venue, the second venue different than the first venue, and wherein synchronizing the first data and the second data further includes:
   aggregating the first physiological data and the second physiological data to generate aggregated physiological data; and
   synchronizing the aggregated physiological data with the media to generate the synchronized response data; and
   further including analyzing the synchronized response data to determine the effectiveness of the media.

16. The method as defined in claim 1, wherein the first physiological data includes electroencephalographic data, the electroencephalographic data including a first frequency band and a second frequency band and the method further includes the first processor determining a difference between an energy level in the first frequency band and the energy level of the second frequency band; and identifying an emotional state of the first subject based on the difference.

17. A computer readable medium carried by a first headset worn by a first subject when the first subject is exposed to media, the computer readable medium comprising instructions, which when executed by a processor of the first headset, cause the processor to at least:

analyze first physiological data gathered by a sensor coupled to the first headset;

generate first data indicative of an emotional response of the first subject based on the physiological data;

synchronize the first data indicative of the emotional response of the first subject with second data indicative of the emotional response of the second subject received from a second headset worn by the second subject to generate synchronized response data; and transmit the synchronized response data to a central unit via a transmitter of the first headset.

18. The computer readable medium as defined in claim 17, wherein the instructions further cause the processor of the first headset to:

analyze a heart rate of the first subject; and
determine if the heart rate is below a threshold.

19. The computer readable medium as defined in claim 18, wherein the instructions further cause the processor of the first headset to disqualify the first subject if the heart rate is not below the threshold.

20. The computer readable medium as defined in claim 17, wherein the instructions further cause the processor of the first headset to:

analyze an energy of an electroencephalographic signal of the first subject; and
determine a mental state based on the energy.

21. The computer readable medium as defined in claim 20, wherein the instructions further cause the processor of the first headset to disqualify the first subject based on the mental state.

22. The computer readable medium as defined in claim 17, wherein the instructions further cause the processor of the first headset to:

analyze a blink rate of the first subject; and
determine if the blink rate is below a threshold.

23. The computer readable medium as defined in claim 22, wherein the instructions further cause the processor of the first headset to disqualify the first subject if the blink rate is not below the threshold.

24. The computer readable medium as defined in claim 17, wherein the instructions further cause the processor of the first headset to test a quality of a connection of the sensor.

25. The computer readable medium as defined in claim 17, wherein the instructions further cause the processor of the first headset to transmit the first physiological data to a set-top box via the transmitter.

26. The computer readable medium as defined in claim 17, wherein the instructions further cause the processor of the first headset to remove data from the first physiological data for a time period during which the first subject was not paying attention to the media.

27. The computer readable medium as defined in claim 26, wherein the instructions further cause the processor of the first headset to interpolate second physiological data based on the first physiological data from a time period when the first subject is paying attention to the media to replace the removed data.

28. The computer readable medium as defined in claim 17, wherein the instructions further cause the processor of the first headset to calculate a score based on the first physiological data, the score representative of an effectiveness of the media.

29. The computer readable medium as defined in claim 17, wherein the instructions cause the processor of the first headset to synchronize the first data and the second data by:

obtaining second physiological data transmitted by the second headset, the second headset including a second sensor to gather second physiological data from the second subject when the second subject is exposed to the media, wherein the first subject is located at a first venue and the second subject is located at a second venue, the second venue different than the first venue;

aggregating the first physiological data and the second physiological data to generate aggregated physiological data;

synchronizing the aggregated physiological data with the media to generate the synchronized response data; and analyzing the synchronized response data to determine the effectiveness of the media.

30. The computer readable medium as defined in claim 17, wherein the physiological data includes electroencephalographic data including a first frequency band and a second frequency band, and wherein the instructions further cause the processor of the first headset to:

determine a difference between an energy level of the first frequency band and an energy level of the second frequency band; and identify an emotional state of the first subject based on the difference.

31. A system comprising:

a first headset to be worn by a first subject, the first headset including:

a first sensor carried by the first headset and positioned to gather first physiological data from the first subject when the first subject is exposed to media;

a first processor carried by the first headset to:
analyze the first physiological data; and
generate first data indicative of an emotional response of the first subject based on the first physiological data;

a first transmitter carried by the first headset to transmit the first data;

a second headset worn by a second subject, the second headset including:

a first transceiver carried by the second headset to receive the first data;

a second sensor carried by the second headset, the second sensor to gather second physiological data from the second subject when the second subject is exposed to the media;

a second processor carried by the second headset to:
process the first data received from the first transmitter; and
synchronize the first data with second data indicative of an emotional response of the second subject for the media to generate synchronized response data; and a second transmitter carried by the second headset to transmit the synchronized response data to a central unit.

32. The system as defined in claim 31, wherein the first headset further includes:
   signal processing circuitry to process the first physiological data, the signal processing circuitry disposed at a first end of the first headset to be positioned adjacent a first ear of the first subject; and
   power circuitry to power the headset, the power circuitry disposed at a second end of the first headset, opposite the first end, to be positioned adjacent a second ear of the first subject.

33. The system of claim 31, wherein the first processor is to:
   generates the first data indicative of a first emotional response of the first subject at a first time relative to the media based on the first physiological data;
   generates third data indicative of a second emotional response of the first subject at a second time relative to the media based on the first physiological data;
   aggregates the first data and the third data to obtain a comprehensive emotional response for the first subject, the comprehensive emotional response representative of an emotional response of the first subject for a duration of the media; and
   the first transmitter transmits the comprehensive emotional response.

34. The system of claim 33, wherein the first processor is to:
   removes a portion from at least one of the first data indicative of the first emotional response at the first time or the third data indicative of the second response at the second time, the portion corresponding to a variance in the first physiological data during at least one of the first time or the second time that is below a threshold; and
   aggregates a remainder of the respective first data or the third data to obtain the comprehensive emotional response.

35. The system of claim 34, wherein the threshold the portion is removed if the variance is flat without much variation during at least one of the first time or the second time.

36. The system of claim 31, further including a stabilizer carried by the first headset to support the first headset on a head of the first subject.

37. The system of claim 36 further including a support strap, the stabilizer disposed between the first processor and the first transmitter on a first side of the first headset, and the support strap disposed between the first processor and the first transmitter on a second side of the first headset.

38. The system as defined in claim 36, wherein the stabilizer includes a silicon strip.

39. The system as defined in claim 36, wherein the stabilizer provides adhesion to the head of the first subject.

40. The system as defined in claim 39, wherein the adhesion is created by a sweat layer caused by the stabilizer.

41. The system as defined in claim 31, wherein the first headset includes a foam pad proximate to the first sensor, the foam pad to apply an even pressure distribution at a front and a back of a head of the first subject.

42. The system as defined in claim 31, wherein the first headset further includes a headband to hold the first sensor near a brow of a head of the first subject.

43. The system as defined in claim 31, wherein the first processor provides a tutorial to the first subject to inform the first subject how to fit and wear the first headset.

44. The system as defined in claim 43, wherein the first processor analyzes a heart rate of the first subject to determine if the heart rate is below a threshold.

45. The system as defined in claim 44, wherein if the heart rate is not below the threshold, the first processor disqualifies the first subject.

46. The system as defined in claim 43, wherein the first processor analyzes a blink rate of the first subject to determine if the blink rate is below a threshold.

47. The system as defined in claim 46, wherein if the blink rate is not below the threshold, the first processor disqualifies the first subject.

48. The system as defined in claim 31, wherein the first processor analyzes an energy of an electroencephalographic signal of the first subject to determine a mental state based on the energy.

49. The system as defined in claim 48, wherein the first processor disqualifies the first subject based on the mental state.

50. The system of claim 31, wherein the first processor tests a quality of a connection of the first sensor.

51. The system as defined in claim 31, wherein the first sensor includes a dry electrode.

52. The system as defined in claim 31, wherein the first transmitter includes a wireless communication device.

53. The system as defined in claim 31, further including a set-top box to receive the first physiological data from the first transmitter.

54. The system as defined in claim 31, wherein the first processor removes data from the first physiological data for a time period during which the first subject was not paying attention to the media.

55. The system as defined in claim 54, wherein the first processor interpolates second physiological data based on the first physiological data from a time period when the first subject is paying attention to the media to replace the removed data.

56. The system as defined in claim 54, wherein the removed physiological data corresponds to data gathered during a time in which an action of the first subject was one or more of talking, nodding off, sleeping, or turning his or her head.

57. The system as defined in claim 31, wherein the first processor includes a rating module to calculate a score based on the first physiological data, the score representative of an effectiveness of the media.

58. The system as defined in claim 31, wherein the first physiological data includes one or more of a heart rate, a brain wave, an electroencephalographic signal, a blink rate, a breathing pattern, a motion, a muscle movement or a galvanic skin response.

59. The system as defined in claim 31, wherein the first sensor includes one or more of a physiological sensor, an electrode, an accelerometer, a blood oxygen sensor, a galvanometer or a heart rate sensor.

60. The system as defined in claim 31, wherein the first physiological data is analyzed to determine one or more of a liking, a thought, an adrenaline response, an engagement, a stress response, a response of frustration or an immersion.

61. The system as defined in claim 31, wherein the media includes as least one of entertainment, a logo, a song, a joke, a spokesperson, a storyline, a television program, an advertisement, a movie, printed media, a website, a computer application, a video game, a live performance, a product, product information, product content or media related to a product development.

62. The system as defined in claim 31, wherein the first subject is located at a first venue and the second subject is located at a second venue, the second venue different than, and geographically separate from, the first venue.

63. The system as defined in claim 31, wherein the second data includes second physiological data and the second processor aggregates the first physiological data and the second physiological data to generate aggregated physiological data.

64. The system as defined in claim 63, wherein the second processor synchronizes the aggregated physiological data with the media to generate the synchronized response data.

65. The system as defined in claim 64, wherein the second processor analyzes the synchronized response data to determine the effectiveness of the media.

66. The system as defined in claim 31, wherein the first physiological data includes electroencephalographic data, the electroencephalographic data including a first frequency band and a second frequency band, the first processor:
    determines a difference between an energy level in the first frequency band and an energy level the second frequency band; and
    identifies an emotional state of the first subject based on the difference.

\* \* \* \* \*

UNITED STATES PATENT AND TRADEMARK OFFICE
CERTIFICATE OF CORRECTION

PATENT NO. : 9,521,960 B2
APPLICATION NO. : 12/263331
DATED : December 20, 2016
INVENTOR(S) : Hans C. Lee, Timmie T. Hong and Juan C. Munoz It is certified that error appears in the above-identified patent and that said Letters Patent is hereby corrected as shown below:

Column 47, Lines 15 and 16 (Claim 33): Delete the words "is" and "to" after "processor"

Column 47, Lines 31 and 32 (Claim 34): Delete the words "is" and "to" after "processor"

Signed and Sealed this
Twenty-eighth Day of February, 2017

Michelle K. Lee
*Director of the United States Patent and Trademark Office*